United States Patent
Annabi et al.

(10) Patent No.: US 10,723,783 B2
(45) Date of Patent: Jul. 28, 2020

(54) POLYPEPTIDE COMPOSITIONS AND METHODS OF USING THE SAME

(71) Applicant: THE BRIGHAM AND WOMEN'S HOSPITAL, INC., Boston, MA (US)

(72) Inventors: Nasim Annabi, Cambridge, MA (US); Ali Khademhosseini, Cambridge, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/559,481

(22) PCT Filed: Mar. 18, 2016

(86) PCT No.: PCT/US2016/023121
§ 371 (c)(1),
(2) Date: Sep. 19, 2017

(87) PCT Pub. No.: WO2016/149615
PCT Pub. Date: Sep. 22, 2016

(65) Prior Publication Data
US 2018/0111978 A1    Apr. 26, 2018

Related U.S. Application Data

(60) Provisional application No. 62/135,405, filed on Mar. 19, 2015, provisional application No. 62/173,653, filed on Jun. 10, 2015.

(51) Int. Cl.
| | | |
|---|---|---|
| *A61K 38/16* | (2006.01) | |
| *C07K 14/78* | (2006.01) | |
| *A61L 24/10* | (2006.01) | |
| *A61L 26/00* | (2006.01) | |
| *A61L 24/00* | (2006.01) | |
| *A61L 27/22* | (2006.01) | |
| *A61L 27/52* | (2006.01) | |
| *A61L 27/54* | (2006.01) | |

(52) U.S. Cl.
CPC .......... *C07K 14/78* (2013.01); *A61L 24/0015* (2013.01); *A61L 24/0031* (2013.01); *A61L 24/108* (2013.01); *A61L 26/008* (2013.01); *A61L 26/0047* (2013.01); *A61L 26/0066* (2013.01); *A61L 27/227* (2013.01); *A61L 27/52* (2013.01); *A61L 27/54* (2013.01); *A61L 2300/404* (2013.01); *A61L 2300/418* (2013.01); *A61L 2300/64* (2013.01); *A61L 2400/04* (2013.01)

(58) Field of Classification Search
None
See application file for complete search history.

(56) References Cited

U.S. PATENT DOCUMENTS

| | | |
|---|---|---|
| 5,064,430 A | 11/1991 | Urry |
| 5,674,623 A | 10/1997 | Haddon et al. |
| 6,458,386 B1 | 10/2002 | Schacht et al. |
| 6,585,873 B1 | 7/2003 | Solomon et al. |
| 6,608,040 B1 | 8/2003 | Lin et al. |
| 7,435,425 B2 | 10/2008 | Qian et al. |
| 7,547,446 B2 | 6/2009 | Qian et al. |
| 7,854,923 B2 | 12/2010 | Chen et al. |
| 7,871,637 B2 | 1/2011 | Qian et al. |
| 7,871,639 B2 | 1/2011 | Schankereli et al. |
| 8,092,820 B2 | 1/2012 | Qian et al. |
| 8,314,211 B2 | 11/2012 | Falus |
| 8,383,141 B2 | 2/2013 | Qian et al. |
| 8,513,217 B2 | 8/2013 | Chen et al. |
| 9,066,991 B2 | 6/2015 | Preiss-Bloom et al. |
| 9,084,728 B2 | 7/2015 | Goessl et al. |
| 10,301,597 B2* | 5/2019 | Lipke .................. C12N 5/0696 |
| 2004/0110439 A1 | 6/2004 | Chaikof et al. |
| 2005/0112182 A1 | 5/2005 | Minami et al. |
| 2008/0312156 A1 | 12/2008 | Setton et al. |
| 2009/0175946 A1 | 7/2009 | Gaissmaier et al. |
| 2012/0128653 A1 | 5/2012 | Goessl et al. |
| 2013/0172985 A1 | 7/2013 | Prestwich et al. |
| 2014/0107065 A1 | 4/2014 | Chen et al. |
| 2014/0377326 A1 | 12/2014 | Niu et al. |
| 2015/0037314 A1 | 2/2015 | Larsen |
| 2015/0209109 A1 | 7/2015 | Rege et al. |
| 2015/0291939 A1 | 10/2015 | Tomer et al. |
| 2017/0049923 A1* | 2/2017 | Olsen ....................... A61K 8/64 |

OTHER PUBLICATIONS

Annabi et al. "25th Anniversary Article: Rational Design and Applications of Hydrogels in Regenerative Medicine" Adv. Mater. 26:85-124 (Year: 2014).*
Glassman M and Olsen B "End Block Design Modulates the Assembly and Mechanics of Thermoresponsive, Dual-Associative Protein Hydrogels" Macromolecules 48:1832-1842. (Year: 2015).*
Meddahi-Pelle et al. "Organ Repair, Hemostasis, and In Vivo Bonding of Medical Devices by Aqueous Solutions of Nanoparticles" Angewandte Chemie Intl. Ed. 53:6369-6373. (Year: 2014).*
Glassman et al., "End block design modulates the Assembly and Mechanics of Thermoresponsive, Dual-Associative Protein Hydrogels", Macromolecules 48(6): 1832-1842 (2015).

(Continued)

*Primary Examiner* — James H Alstrum-Acevedo
*Assistant Examiner* — Zachary J Miknis
(74) *Attorney, Agent, or Firm* — Nixon Peabody LLP; David S. Resnick; Mark J. FitzGerald

(57) ABSTRACT

Disclosed herein are polypeptides comprising an amino acid sequence of $\{[VPGVG]_4 IPGVG\}_n$, wherein n is an integer greater than 1. The polypeptides can be crosslinked to from biocompatible hydrogels with tunable and desirable mechanical properties. The polypeptides and hydrogels can be used in a variety of biomedical applications including treatment of bleeding, treatment of soft tissue injury, injectable filler, and tissue adhesives.

17 Claims, 7 Drawing Sheets

Specification includes a Sequence Listing.

(56) References Cited

OTHER PUBLICATIONS

Zhang et al., "A Highly Elastic and Rapidly Crosslinkable Elastin-Like Polypeptide-Based Hydrogel for Biomedical Applications", Advanced Functional Material 25(30): 4814-4826 (2015).
Jun et al., "Comparison of Bursting Pressure after Scleral Tunnel Incision Sealed with Sutures or an Adherent Ocular Bandage in Human Globes", The Journal of International Medical Research 40:756-760 (2012).
Katagiri et al., "All Six Modules of the Gelatin-binding Domain of Fibronectin Are Required for Full Affinity", The Journal of Biological Chemistry 278(14):11897-11902 (2003).
Kharazifia et al., "Tough and Flexible CNT—Polymeric Hybrid Scaffolds for Engineering Cardiac Constructs", Biomaterials 35(26):7346-7354 (2014).
Kim et al., "Self-Assembly of Thermally Responsive Amphiphilic Diblock Copolypeptides into Spherical Micellar Nanoparticles", Angewandte Chemie International Edition 49:4257-4260 (2010).
Kim et al., "Biomimetic Scaffolds for Tissue Engineering", Advanced Functional Materials 22:2446-2468 (2012).
Kobayashi et al., "In Vivo Evaluation of a New Sealant Material on a Rat Lung Air Leak Model", Journal of Biomedical Materials Research (Applied Biomaterials) 58:658-665 (2001).
Lai et al., "Gelatin methacrylatelcarboxybetaine methacrylate hydrogels with tunable crosslinking for controlled drug release", Journal of Materials Chemistry B 4:2304-2313 (2016).
Leahey et al., "Clinical Experience with N-butyl Cyanoacryiate (Nexacryl) Tissue Adhesive", Ophthalmology 100 (2):173-180 (1993).
Lee et al., "Hydrogels for Tissue Engineering", Chemical Reviews 101(7):1869-1879 (2001).
Li et al., "Toward a Stretchable, Elastic, and Electrically Conductive Nanocomposite: Morphology and Properties of Poly[styrene-b-(ethylene-co-butylene)-b-styrene]/Multiwalled Carbon Nanotube Composites Fabricated by High-Shear Processing", Macromolecules 42(7):2587-2593 (2009).
Lim et al., "Rapid Crosslinking of Elastin-like Polypeptides with Hydroxymethylphosphines in Aqueous Solution", Biomacromolecules 8(5):1463-1470 (2007).
Lynn et al., "Antigenicity and Immunogenicity of Collagen", Journal of Biomedical Materials Research Part B: Applied Biomaterials 716:343-354 (2004).
MacEwan et al., "Elastin-Like Polypeptides: Biomedical Applications of Tunable Biopolymers", Peptide Science 94 (1):60-77 (2010).
MacEwan et al., "Applications of elastin-like polypeptides in drug delivery", Journal of Controlled Release 190:314-330 (2014).
McHale et al., "Synthesis and in Vitro Evaluation of Enzymatically Cross-Linked Elastin-Like Polypeptide Gels for Cartilaginous Tissue Repair", Tissue Engineering 11(11/12):1768-1779 (2005).
Mehdizadeh et al., "Injectable citrate-based mussel-inspired tissue bioadhesives with high wet strength for sutureless wound closure", Biomaterials 33:7972-7983 (2012).
Meyer et al., "Purification of recombinant proteins by fusion with thermally-responsive polypeptides", Nature Biotechnology 17:1112-1115 (1999).
Montanaro et al., "Cytotoxicity, blood compatibility and antimicrobial activity of two cyanoacrylate glues for surgical use", Biomaterials 22:59-66 (2001).
Munoz et al., "Gelatin hydrogels formed by orthogonal thiol-norbornene photochemistry for cell encapsulation", Biomaterials Science 2:1063-1072 (2014).
Nagapudi et al., "Photomediated Solid-State Cross-Linking of an Elastin-Mimetic Recombinant Protein Polymer", Macromolecules 35(5):1730-1737 (2002).
Nakayama et al., "Enhancement of visible light-induced gelation of photocurable gelatin by addition of polymeric amine", Journal of Photochemistry and Photobiology A: Chemistry 177:205-211 (2006).
Nan et al., "Nosocomial Infection After Lung Surgery: Incidence and Risk Factors", Chest 128(4):2647-2652 (2005).
Nettles et al., "In Situ Crosslinking Elastin-Like Polypeptide Gels for Application to Articular Cartilage Repair in a Goat Osteochondral Defect Model", Tissue Engineering Part A 14(7):1133-1140 (2008).
Nettles et al., "Applications of Elastin-like Polypeptides in Tissue Engineering", Advanced Drug Delivery Reviews 62 (15):1479-1485 (2010).
Nichol et al., "Cell-laden microengineered gelatin methacrylate hydrogels", Biomaterials 31:5536-5544 (2010).
Nikkhah et al., "Directed endothelial cell morphogenesis in micropatterned gelatin methacrylate hydrogels", Biomaterials 33:9009-9018 (2012).
Okajima et al., "Kinetics of volume phase transition in poly(N-isopropylacrylamide) gels", Journal of Chemical Physics 116(20):9068-9077 (2002).
Omidian et al., "Elastic, Superporous Hydrogel Hybrids of Polyacrylamide and Sodium Alginate", Macromolecular Bioscience 6:703-710 (2006).
Papatheofanis F., "Prothrombotic Cytotoxicity of Cyanoacrylate Tissue Adhesive", Journal of Surgical Research 17(4):309-312 (1989).
Park et al., "Evaluation of Polyethylene Glycol Based Hydrogel for Tissue Sealing After Laparoscopic Partial Nephrectomy in a Porcine Model", The Journal of Urology 172:2446-2450 (2004).
Paul et al., "Injectable Graphene Oxide/Hydrogel-Based Angiogenic Gene Delivery System for Vasculogenesis and Cardiac Repair", ACS Nano 8(8):8050-8062 (2014).
Qerimi et al., "Collagen hemostat significantly reduces time to hemostasis compared with cellulose: COBBANA, a single-center, randomized trial", The American Journal of Surgery 205(6):636-641 (2013).
Raphel et al., "Photoreactive elastin-like proteins for use as versatile bioactive materials and surface coatings", Journal of Materials Chemistry 22(37):19429-19437 (2012).
Rogers et al., "Materials and Mechanics for Stretchable Electronics", Science 327:1603-1607 (2010).
Shazly et al., "Viscoelastic adhesive mechanics of aldehyde-mediated soft tissue sealants", Biomaterials 29:4584-4591 (2008).
Shin et al., "Carbon Nanotube Reinforced Hybrid Microgels as Scaffold Materials for Cell Encapsulation", ACS Nano 6 (1):362-372 (2012).
Shin et al., "Carbon-Nanotube-Embedded Hydrogel Sheets for Engineering Cardiac Constructs and Bioactuators", ACS Nano 7(3):2369-2380 (2013).
Siegal et al., "Surgical Removal of Cyanoacrylate Adhesive After Accidental Instillation in the Anterior Chamber", Ophthalmic Surgery 20(3):179-181 (1989).
Spotnitz et al., "Hemostats, sealants, and adhesives III: a new update as well as cost and regulatory considerations for components of the surgical toolbox", Transfusion 52:2243-2255 (2012).
Sun et al., "Highly stretchable and tough hydrogels", Nature 489(7414):133-136 (2012).
Tang et al., "Oxidatively Responsive Chain Extension to Entangle Engineered Protein Hydrogels", Macromolecules 47(2):791-799 (2014).
Teng et al., "Morphological analysis of leucocyte transmigration in the pleural cavity", Journal of Anatomy 203:391-404 (2003).
Tessmar et al., "Customized PEG-Derived Copolymers for Tissue-Engineering Applications", Macromolecular Bioscience 7:23-39 (2007).
Than et al., "Polyethylene Glycol Hydrogel Dural Sealant May Reduce Incisional Cerebrospinal Fluid Leak After Posterior Fossa Surgery", Operative Neurosurgery 63(ONS Suppl 1):ONS182-ONS187 (2008).
Trabbic-Carlson et al., "Swelling and Mechanical Behaviors of Chemically Cross-Linked Hydrogels of Elastin-like Polypeptides", Biomacromolecules 4(3):572-580 (2003).
Urry et al., "Biocompatibility of the Bioelastic Materials, Poly(GVGVP) and Its γ-Irradiation Cross-Linked Matrix: Summary of Generic Biological Test Results", Journal of Bioactive and Compatible Polymers 6:263-282 (1991).
Visser et al., "Endochondral bone formation in gelatin methacrylamide hydrogel with embedded cartilage-derived matrix particles", Biomaterials 1-9 (2014).
Wang et al., "A tough biodegradable elastomer", Nature Biotechnology 20:602-606 (2002).

(56) References Cited

OTHER PUBLICATIONS

Weiss et al., "The Use of Tissue Adhesive in Corneal Perforations", Ophthalmology 90(6):610-615 (1983).
Welsh et al., "Engineering the Extracellular Matrix: A Novel Approach to Polymeric Biomaterials. I. Control of the Physical Properties of Artificial Protein Matrices Designed to Support Adhesion of Vascular Endothelial Cells", Biomacromolecules 1(1)23-30 (2000).
Allen et al., "Prospective Randomized Study Evaluating a Biodegradable Polymeric Sealant for Sealing Intraoperative Air Leaks That Occur During Pulmonary Resection", The Annals of Thoracic Surgery 77:1792-1801 (2004).
Alleyne et al., "Efficacy and biocompatibility of a photopolymerized, synthetic, absorbable hydrogel as a dural sealant in a canine craniotomy model", Journal of Neurosurgery 88:308-313 (1998).
Anegg et al., "Efficiency of fleece-bound sealing (TachoSil®) of air leaks in lung surgery: a prospective randomised trial", European Journal of Cardio-thoracic Surgery 31:198-202 (2007).
Annabi et al., "The fabrication of elastin-based hydrogels using high pressure $CO_2$", Biomaterials 30:1-7 (2009).
Annabi et al., "Synthesis of highly porous crosslinked elastin hydrogels and their interaction with fibroblasts in vitro", Biomaterials 30:4550-4557 (2009).
Annabi et al., "Cross-linked open-pore elastic hydrogels based on tropoelastin, elastin and high pressure $CO_2$", Biomaterials 31:1655-1665 (2010).
Annabi et al., "Highly Elastic Micropatterned Hydrogel for Engineering Functional Cardiac Tissue", Advanced Functional Materials 23:4950-4959 (2013).
Annabi et al., "Engineered cell-laden human protein-based elastomer", Biomaterials 34(22):5496-5505 (2013).
Annabi et al., "25th Anniversary Article: Rational Design and Applications of Hydrogels in Regenerative Medicine", Advanced Materials 26(1):85-124 (2014).
Annabi et al., "Surgical Materials: Current Challenges and Nano-enabled Solutions", Nano Today 9(5):574-589 (2014).
Anselmo et al., "Platelet-like Nanoparticles: Mimicking Shape, Flexibility, and Surface Biology of Platelets To Target Vascular Injuries", ACS Nano 8(11):11243-11253 (2014).
Assmann et al., "The degeneration of biological cardiovascular prostheses under pro-calcific metabolic conditions in a small animal model", Biomaterials 1-13 (2014).
Baldock et al., "Shape of tropoelastin, the highly extensible protein that controls human tissue elasticity", Proceedings of the National Academy of Sciences 108(11):4322-4327 (2011).
Baranoski S., "Choosing a wound dressing, part 1", Nursing2008 60-61 (2008).
Bertassoni et al., "Hydrogel Bioprinted Microchannel Networks for Vascularization of Tissue Engineering Constructs", Lab on a Chip 14(13):2202-2211 (2014).
Betre et al., "Chondrocytic differentiation of human adipose-derived adult stem cells in elastin-like polypeptide", Biomaterials 27:91-99 (2006).
Bitton et al., "Phloroglucinol-based biomimetic adhesives for medical applications", Acta Biomaterialia 5:1582-1587 (2009).
Bottcher-Haberzeth et al., "Tissue engineering of skin", Burns 36:450-460 (2010).
Buckley et al., "Silver carbonate nanoparticles stabilised over alumina nanoneedles exhibiting potent antibacterial properties", Chemical Communications 4013-4015 (2008).
Buskens et al., "The use of a surgical sealant (CoSeal®) in cardiac and vascular reconstructive surgery: an economic analysis", The Journal of Cardiovascular Surgery 47(2):161-170 (2006).
Camci-Unal et al., "Synthesis and Characterization of Hybrid Hyaluronic Acid-Gelatin Hydrogels", Biomacromolecules 14(4):1085-1092 (2013).
Carlson et al., "Giant Papillary Conjunctivitis Associated With Cyanoacrylate Glue", American Journal of Ophthalmology 104(4):437-438 (1987).
Carrico et al., "Lithographic Patterning of Photoreactive Cell-Adhesive Proteins", Journal of the American Chemical Society 129(16):4874-4875 (2007).
Cavanaugh et al., "Infectious Keratitis and Cyanoacrylate Adhesive", American Journal of Ophthalmology 111 (4):466-472 (1991).
Cha et al., "Controlling Mechanical Properties of Cell-Laden Hydrogels by Covalent Incorporation of Graphene Oxide", Small 10(3):514-523 (2014).
Charati et al., "Hydrophilic elastomeric biomaterials based on resilin-like polypeptides", Soft Matter 5(18):3412-3416 (2009).
Chen et al., "Functional Human Vascular Network Generated in Photocrosslinkable Gelatin Methacrylate Hydrogels", Advanced Functional Materials 22(10):2027-2039 (2012).
Chen et al., "Layer-by-Layer Bioprinting of Stem Cells for Retinal Tissue Regeneration", University of California, San Diego (2016). (22 pages).
Chou et al., "Genetically encoding an aliphatic diazirine for protein photocrosslinking", Chemical Science 2:480-483 (2011).
Costa et al., "Stimuli-Responsive Thin Coatings Using Elastin-Like Polymers for Biomedical Applications", Advanced Functional Materials 19:3210-3218 (2009).
Deacon et al., "Antimicrobial efficacy of tobramycin polymeric nanoparticles for Pseudomonas aeruginosa infections in cystic fibrosis: formulation, characterisation and functionalisation with domase alfa (DNase)", Journal of Controlled Release (2015). (16 pages).
Debelle et al., "Elastin: molecular description and function", The International Journal of Biochemistry & Cell Biology 31:261-272 (1999).
Di Zio et al., "Mechanical Properties of Artificial Protein Matrices Engineered for Control of Cell and Tissue Behavior", Macromolecules 36(5):1553-1558 (2003).
Elvin et al., "A highly elastic tissue sealant based on photopolymerised gelatin", Biomaterials 31:8323-8331 (2010).
Elzoghby A., "Gelatin-based nanoparticles as drug and gene delivery systems: Reviewing three decades of research", Journal of Controlled Release 172:1075-1091 (2013).
Fogle et al., "Tissue Adhesive Arrests Stromal Melting in the Human Cornea", American Journal of Ophthalmology 89(6):795-802 (1980).
Foo et al., "Two-component protein-engineered physical hydrogels for cell encapsulation", Proceedings of the National Academy of Sciences 106(52):22067-22072 (2009).
Gaharwar et al., "Shear-Thinning Nanocomposite Hydrogels for the Treatment of Hemorrhage", ACS Nano 8 (10):9833-9842 (2014).
Galler et al., "Self-assembling Multidomain Peptide Hydrogels: Designed Susceptibility to Enzymatic Cleavage Allows Enhanced Cell Migration and Spreading", Journal of the American Chemical Society 132(9):3217-3223 (2010).
Giannandrea et al., "Diverse functions of matrix metalloproteinases during fibrosis", Disease Models & Mechanisms 7:193-203 (2014).
Glickman et al., "A Polymeric Sealant Inhibits Anastomotic Suture Hole Bleeding More Rapidly Than Gelfoam/Thrombin: Results of a Randomized Controlled Trial", Archives of Surgery 137:326-331 (2002).
Gorgieva et al., "Collagen- vs. Gelatine-Based Biomaterials and Their Biocompatibility: Review and Perspectives", Biomaterials Applications for Nanomedicine, InTech (2011). (38 pages).
Hassan et al., "Smart copper oxide nanocrystals: Synthesis, characterization, electrochemical and potent antibacterial activity", Colloids Surfaces B: Biointerfaces 97:201-206 (2012).
He et al., "Polymorphisms in the Human Tropoelastin Gene Modify In Vitro Self-Assembly and Mechanical Properties of Elastin-Like Polypeptides", PLOS One 7(9):e46130 (2012). (12 pages).
Hida et al., "Retinal Toxicity of Cyanoacrylate Tissue Adhesive in the Rabbit", Retina 8:148-153 (1988).
Hjortnaes et al., "Directing Valvular Interstitial Cell Myofibroblast-Like Differentiation in a Hybrid Hydrogel Platform", Advanced Healthcare Materials 4:121-130 (2015).
Hrabchak et al., "Assessment of biocompatibility and initial evaluation of genipin cross-linked elastin-like polypeptides in the treatment of an osteochondral knee defect in rabbits", Acta Biomaterialia 6:2108-2115 (2010).

(56) References Cited

OTHER PUBLICATIONS

Huang et al., "Generation of Synthetic Elastin-Mimetic Small Diameter Fibers and Fiber Networks", Macromolecules 33(8):2989-2997 (2000).

Ifkovits et al., "Review: Photopolymerizable and Degradable Biomaterials for Tissue Engineering Applications", Tissue Engineering 13(10):2369-2385 (2007).

Itano H., "The optimal technique for combined application of fibrin sealant and bioabsorbable felt against alveolar air leakage", European Journal of Cardio-thoracic Surgery 33:457-460 (2008).

Wissink et al., "Immobilization of heparin to EDC/NHS-crosslinked collagen. Characterization and in vitro evaluation", Biomaterials 22:151-163 (2001).

Wolbank et al., "Non-invasive in vivo tracking of fibrin degradation by fluorescence imaging", Journal of Tissue Engineering and Regenerative Medicine 9:973-976 (2015).

Xia et al., "Tunable Self-Assembly of Genetically Engineered Silk-Elastin-Like Protein Polymers", Biomacromolecules 12(11):3844-3850 (2011).

Xia et al., "Nano-structured smart hydrogels with rapid response and high elasticity", Nature Communications 4:2226 (2013). (11 pages).

Xu et al., "Rheological Properties of Cysteine-Containing Elastin-Like Polypeptide Solutions and Hydrogels", Biomacromolecules 13(8):2315-2321 (2012).

Yue et al., "Synthesis, properties, and biomedical applications of gelatin methacryloyl (GelMA) hydrogels", Biomaterials 73:254-271 (2015).

Zhang et al., "Artificial Polypeptide Scaffold for Protein Immobilization", Journal of the American Chemical Society 127(29):10136-10137 (2005).

Zhao et al. "Photocrosslinkable Gelatin Hydrogel for Epidermal Tissue Engineering", Advanced Healthcare Materials 5(1):108-118 (2016).

Zhou et al., "Biomimetic mineralization of anionic gelatin hydrogels: effect of degree of methacrylation", RSC Advances 4:21997-22008 (2014).

Zhu et al., "Design properties of hydrogel tissue-engineering scaffolds", Expert Review of Medical Devices 8(5):607-626 (2011).

* cited by examiner

POLYPEPTIDE COMPOSITIONS AND METHODS OF USING THE SAME

CROSS-REFERENCE TO RELATED APPLICATIONS

This application is a 35 U.S.C. § 371 National Phase Entry Application of International Application No. PCT/US2016/023121 filed Mar. 18, 2016, which designated the U.S., and which claims benefit under 35 U.S.C. 119(e) of U.S. Provisional Patent Application Ser. No. 62/135,405 filed on Mar. 19, 2015 and U.S. Provisional Patent Application Ser. No. 62/173,653 filed Jun. 10, 2015, the contents of each of which are incorporated herein in their entireties by reference.

SEQUENCE LISTING

The application contains a Sequence Listing which has been submitted in ASCII format via EFS-Web and is hereby incorporated by reference in its entirety. Said ASCII copy, is named 043214-084732-PCT_SL and is 78,282 bytes in size

TECHNICAL FIELD

The present invention relates to elastin like polypeptides (ELPs), hydrogels based ELPs, and their use in tissue engineering, wound healing, and other biomedical applications.

BACKGROUND

Elastic biomaterials have been developed by using both natural and synthetic polymers for a wide range of biomedical applications where elasticity plays a critical role. For example, elastic hydrogels are ideal for tissue engineering applications that require stretchable biomaterials (Shin S R, et al., *ACS Nano* 7, 2369-2380 (2013); Kharaziha M, et al., *Biomaterials* 35, 7346-7354 (2014); Paul A, et al., *ACS Nano* 8, 8050-8062 (2014); Annabi N, et al., *Adv Funct Mater* 23, 4950-4959 (2013)) such as engineering soft and elastic tissues, like skin and blood vessels (Böttcher-Haberzeth S, et al., *Burns* 36, 450-460 (2010); Kim T G, et al., *Adv Funct Mater* 22, 2446-2468 (2012)). Other biomedical applications including tissue adhesives (Annabi N, et al., *Nano Today* 9, 574-589 (2014); Elvin C M, et al., *Biomaterials* 31, 8323-8331 (2010)), smart hydrogels (Xia L-W, et al., *Nat Commun* 4, (2013)), and flexible electronics (Rogers J A, et al., *Science* 327, 1603-1607 (2010)) also demand materials with high elasticity and rapid response to applied mechanical forces. Synthetic elastomers (Wang Y, et al., *Nat Biotech* 20, 602-606 (2002)), interpenetrating networks (Omidian H, et al., *Macromol Biosci* 6, 703-710 (2006)), and nanocomposite hydrogels (Li Y, et al., *Macromolecules* 42, 2587-2593 (2009)) have been investigated for generating elastic substrates but properties such as cell adhesion, degradability, and overall biocompatibility must be artificially incorporated into these polymeric systems (Zhu J, et al., *Expert review of medical devices* 8, 607-626 (2011)).

Alternatively, recombinant protein-based polymers such as elastin-like polypeptides (ELPs) are biocompatible (MacEwan S R, et al., *Biopolymers* 94, 60-77 (2010); Nettles D L, et al., *Adv Drug Delivery Rev* 62, 1479-1485 (2010)) and have been widely investigated for biomedical applications (Nettles D L, et al., *Adv Drug Delivery Rev* 62, 1479-1485 (2010); Nettles D L, et al., *Tissue engineering Part A* 14, 1133-1140 (2008); McHale M K, et al., *Tissue Eng* 11, 1768-1779 (2005)). They recapitulate the extensibility of natural elastin using a pentapeptide repeat, VPGXG, where X is any amino acid besides proline (SEQ ID NO: 1) (MacEwan S R, et al., *Biopolymers* 94, 60-77 (2010); Baldock C, et al., *Proc Natl Acad Sci* 108, 4322-4327 (2011)). The unique properties of ELPs include their reversible thermoresponsive nature (Meyer D E, et al., *Nat Biotech* 17, 1112-1115 (1999)), modular design (Raphel J, et al., *J Mater Chem* 22, 19429-19437 (2012); Betre H, et al., *Biomacromolecules* 3, 910-916 (2002)), and mechanical properties (McHale M K, et al., *Tissue Eng* 11, 1768-1779 (2005)), making them suitable candidates for various applications such as thermoresponsive drug carriers, thermal purification components, self-assembly building blocks, and hydrogels for tissue regeneration (Nettles D L, et al., *Adv Drug Delivery Rev* 62, 1479-1485 (2010); McHale M K, et al., *Tissue Eng* 11, 1768-1779 (2005); Xia X X, et al., *Biomacromolecules* 12, 3844-3850 (2011)). However, many ELP-based biomaterials have lower elasticity and mechanical properties compared to synthetic polymeric scaffolds (Trabbic-Carlson K, et al., *Biomacromolecules* 4, 572-580 (2003)). They also require chemical modification and long crosslinking time to form three dimensional (3D) scaffolds, limiting their capability for 3D cell encapsulation (Raphel J, et al., *J Mater Chem* 22, 19429-19437 (2012)).

To alter the mechanical properties of ELPs, various crosslinking approaches such as physical (through temperature changes), chemical, and enzymatic crosslinking have been applied (Chou C, et al., *Chemical Science* 2, 480-483 (2011)). Above an ELP's lower critical solution temperature (LCST), ELP agglomeration occurs, forming coacervates (viscous liquids), which can be used as a cell carrier or injectable delivery system (MacEwan S R, et al., *Biopolymers* 94, 60-77 (2010)). However, these viscous liquids are not capable of providing the mechanics necessary for many tissue engineering applications. For the formation of more stable gels, chemical crosslinking of ELPs has been performed. ELPs can be crosslinked through chemical functionalization of the protein sequence (e.g. addition of vinyl groups) using N-hydroxysuccinimide (NHS) reactions, glutaraldehyde (Ifkovits J L, et al., *Tissue Eng* 10, 2369-2385 (2007); Wissink M J B, et al., *Biomaterials* 22, 151-163 (2001)), or through reacting amines or carboxyl groups in the biopolymer (Nettles D L, et al., *Adv Drug Delivery Rev* 62, 1479-1485 (2010); Nettles D L, et al., *Tissue engineering Part A* 14, 1133-1140 (2008); Raphel J, et al., *J Mater Chem* 22, 19429-19437 (2012); Chou C, et al., *Chemical Science* 2, 480-483 (2011)). Chemical modifications can introduce well-defined concentrations of crosslinkers per molecule, providing control over both the location and amount of added crosslinkable groups. However, long reaction times and generation of toxic byproducts in chemical crosslinking methods may limit the applications of resulting ELP biomaterials in situations where rapid gelation in biological conditions is required. For example, NETS-based coupling reactions commonly require minutes to hours to react generating toxic byproducts (Huang L, et al., *Macromolecules* 33, 2989-2997 (2000); Zhang K, et al., *J Am Chem Soc* 127, 10136-10137 (2005)), which is not ideal for clinical applications. Enzymatic crosslinking of proteins also suffers from similar restrictions (McHale M K, et al., *Tissue Eng* 11, 1768-1779 (2005)).

To address these limitations, photocrosslinkable ELP-based scaffolds have been developed. For example, non-canonical amino acids have been recombinantly incorporated to provide photocrosslinkable sites within the protein but the protein yield using this technology was very low, limiting the scalability and widespread applications of this approach (Nagapudi K, et al., *Macromolecules* 35, 1730-1737 (2002)). Photocrosslinking of ELPs has also been performed by functionalizing lysine groups with acrylate moieties (K. Nagapudi, W. T. Brinkman, J. E. Leisen, L. Huang, R. A. McMillan, R. P. Apkarian, V. P. Conticello, E. L. Chaikof, *Macromolecules* 2002, 35, 1730) or NETS ester-diazirine crosslinker (Raphel J, et al., *J Mater Chem* 22, 19429-19437 (2012)) to produce stable biomaterials. These approaches have been utilized to design dried films or fibers with high modulus (40-60 MPa) and low fracture strain (2%) but rarely for the formation of bulk hydrogels, which are necessary for any 3D applications, including cell encapsulation (Bertassoni L E, et al., *Lab on a Chip* 14, 2202-2211 (2014)), micropatterning (Annabi N, et al., *Biomaterials* 34, 5496-5505 (2013)), or molding (Nettles D L, et al., *Adv Drug Delivery Rev* 62, 1479-1485 (2010); Foo CTWP, et al., *Proc Natl Acad Sci* 106, 22067-22072 (2009); Tang S, et al., *Macromolecules* 47, 791-799 (2014)) by soft lithography. The functionalized ELP polymers also required long UV exposure times (1-2 h) to be crosslinked (Raphel J, et al., *J Mater Chem* 22, 19429-19437 (2012); Nichol J W, et al., *Biomaterials* 31, 5536-5544 (2010)), limiting their capability for 3D cell encapsulation and fast polymerizable materials for surgical application or injectable fillers.

SUMMARY

The technology described herein relates to engineered polypeptides that can crosslink to form biocompatible hydrogels with tunable and desirable mechanical properties. The polypeptides can further comprise a pair of cysteine residues to allow disulfide bond formation, leading to the formation of an elastic hydrogel. The physical properties of the resulting hydrogel such as mechanical properties and swelling behavior can be tuned, e.g., by controlling the polypeptide concentrations.

In one aspect, the technology described herein relates to a polypeptide comprising an amino acid sequence of $\{[VPGVG]_4IPGVG\}_n$, wherein n is an integer greater than 1 (SEQ ID NO: 2).

In one aspect, the technology described herein relates to a composition comprising a polypeptide described herein and a photoinitiator.

In one aspect, the technology described herein relates to a kit comprising a polypeptide described herein and a photoinitiator.

In one aspect, the technology described herein relates to a hydrogel comprising a polypeptide comprising an amino acid sequence of $\{[VPGVG]_4IPGVG\}_n$, wherein n is an integer greater than 1 (SEQ ID NO: 2).

In some embodiments of any one of the above aspects, n is in the range of 10-28.

In some embodiments of any one of the above aspects, n is in the range of 10-14.

In some embodiments of any one of the above aspects, n is 14.

In some embodiments of any one of the above aspects, the polypeptide further comprises a first cysteine-containing peptide linked to a first side of the amino acid sequence of $\{[VPGVG]_4IPGVG\}_n$ (SEQ ID NO: 2).

In some embodiments of any one of the above aspects, the polypeptide further comprises a second cysteine-containing peptide linked to a second side of the amino acid sequence of $\{[VPGVG]_4IPGVG\}_n$ (SEQ ID NO: 2).

In some embodiments of any one of the above aspects, the first cysteine-containing peptide comprises an amino acid sequence of KCTS (SEQ ID NO: 6).

In some embodiments of any one of the above aspects, the second cysteine-containing peptide comprises an amino acid sequence of KCTS (SEQ ID NO: 6).

In some embodiments of any one of the above aspects, the polypeptide further comprises an amino acid sequence of RGD.

In some embodiments of any one of the above aspects, the photoinitiator is selected from the group consisting of 1-[4-(2-Hydroxyethoxy)-phenyl]-2-hydroxy-2-methyl-1-propane-1-one, 1-hydroxycyclohexyl phenyl ketone, 2-benzyl-2,N,N-dimethylamino-1-(4-morpholinophenyl)-1-butanone, 2-hydroxy-2-methyl-1-phenyl propane-1-one, 2,2-dimethoxy-2-phenylacetophenone, and Eosin Y.

In some embodiments of the hydrogels described herein, the polypeptide is present at a concentration between 5% and 30% (w/v). In some embodiments of the hydrogels described herein, the polypeptide is present at a concentration between 10% and 30% (w/v). In some embodiments of the hydrogels described herein, the polypeptide is present at a concentration between 10% and 20% (w/v).

In some embodiments of the hydrogels described herein, the hydrogel has extensibility up to 500%. In some embodiments of the hydrogels described herein, the hydrogel has extensibility up to 450%. In some embodiments of the hydrogels described herein, the hydrogel has extensibility up to 400%.

In some embodiments of the hydrogels described herein, the hydrogel has an elastic modulus in the range of 0.5-10 kPa. In some embodiments of the hydrogels described herein, the hydrogel has an elastic modulus in the range of 1-5 kPa. In some embodiments of the hydrogels described herein, the hydrogel has an elastic modulus in the range of 1-2.5 kPa.

In some embodiments of the hydrogels described herein, the hydrogel has a tensile strength in the range of 4 to 20 kPa. In some embodiments of the hydrogels described herein, the hydrogel has a tensile strength in the range of 5 to 15 kPa. In some embodiments of the hydrogels described herein, the hydrogel has a tensile strength in the range of 6 to 12 kPa.

In some embodiments of the hydrogels described herein, the hydrogel has a compressive modulus of 1 to 20 kPa. In some embodiments of the hydrogels described herein, the hydrogel has a compressive modulus of 2 to 18 kPa. In some embodiments of the hydrogels described herein, the hydrogel has a compressive modulus of 3 to 15 kPa.

In some embodiments of the hydrogels described herein, the hydrogel further comprises a hemostatic agent selected from the group consisting of silica nanoparticles, blood coagulation factors, prothrombin, thrombin, fibrinogen, fibrin, gelatin, collagen, polysaccharide, and cellulose.

In some embodiments of the hydrogels described herein, the hydrogel further comprises an antibacterial agent selected from the group consisting of silver nanoparticles, copper oxide nanoparticles, nanoparticle-carried antibiotic drugs, penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, and sulfamethoxazole.

In some embodiments of the hydrogels described herein, the hydrogel further comprises one or more biological cells.

In some embodiments of the hydrogels described herein, the hydrogel is biocompatible.

In some embodiments of the hydrogels described herein, the hydrogel is produced by crosslinking the polypeptide in the presence of a photoinitiator under light irradiation (e.g., ultraviolet or visible light).

A variety of methods can be applied to polymerize the polypeptides described herein. These methods include, but are not limited to, photoinitiation, Michael addition, and other thiol reactions.

The polypeptides and hydrogels described herein can have a variety of biomedical applications. One aspect of the technology described herein also relates to a tissue scaffold comprising the hydrogel described herein and one or more biological cells. The tissue scaffold can be used to promote tissue ingrowth or deliver growth factors.

The hydrogels described herein can also be used to treat bleeding, wherein the hydrogel comprising a hemostatic agent. Other uses include treatment of an injury in a soft and elastic tissue such as a blood vessel, skin, lung, cartilage, nucleus pulposus, bladder, and a cardiac tissue.

BRIEF DESCRIPTION OF THE DRAWINGS

The patent or application file contains at least one drawing executed in color. Copies of this patent or patent application publication with color drawings will be provided by the Office upon request and payment of the necessary fee.

(FIG. 1A) Sequences of expressed ELPs (SEQ ID NOS 24 and 25, respectively, in order of appearance) to test photocrosslinking. (FIG. 1B) Proposed photocrosslinking mechanism for cysteine-containing ELP (KCTS-$E_{31}$-KCTS (i.e., KCTS-$\{[VPGVG]_4IPGVG\}_{14}$-KCTS)) (SEQ ID NO: 7), involving chain extension via disulfide bond formation (red bonds) and interchain crosslinking among ELP residues (green bonds). (FIG. 1C) Representative images of 10% (w/v) aqueous ELP solutions after UV exposure in the presence of a photoinitiator and after incubation with a reducing agent (tris (2-carboxyethyl) phosphine hydrochloride). KCTS-$E_{31}$-KCTS (SEQ ID NO: 7) forms a gel after photocrosslinking while $E_{22}$, an ELP lacking cysteine, remains a liquid. After reduction, KCTS-$E_{31}$-KCTS (SEQ ID NO: 7) is much smaller in size suggesting a mass loss after reduction. (FIG. 1D) Protein electrophoresis gels of reduced hydrogels show bands (circled on gel), at double and triple the protein molecular weight when compared to non-reduced gels, indicating high molar mass proteins and some bonds other than disulfide bonds are formed during photocrosslinking.

(FIG. 2D) Effect of protein concentrations on the average apparent pore sizes of ELP gels, derived from SEM images (n=90). The apparent pore size decreases by increasing the protein concentration. (FIG. 2E) Time course of the swelling ratio depending on different ELP concentrations at 37° C. (FIG. 2F) Swelling ratio after 24 hours depending on temperature and ELP concentrations ($*p<0.05$, $p<0.01$, $*p<0.001$, $****p<0.0001$).

(FIG. 3A) Images of a 10% (w/v) ELP hydrogel during stretching. The engineered ELP hydrogel stretched more than 4 times of its initial length before break. (FIG. 3B) Representative tensile stress-strain curves and (FIG. 3C) elastic modulus of hydrogels produced with different ELP concentrations. (FIG. 3D) Images of a 10% (w/v) ELP hydrogel during compression test. (FIG. 3E) Representative compressive cyclic loading and unloading curves for ELP hydrogels with different ELP concentrations. (FIG. 3F) Compressive modulus of hydrogels produced with different ELP concentrations. (FIG. 3G) Energy loss calculated from the area between the loading and unloading curves depending on the ELP concentrations ($*p<0.05$, $p<0.01$, $**p<0.0001$).

(FIGS. 4A-4B) Calcein-AM (green)/ethidium homodimer (red) LIVE/DEAD assay on ELP hydrogels seeding with MSCs (FIG. 4A) or HUVECs (FIG. 4B) at day 7 of culture (scale bar=200 μm). (FIG. 4C) Viability results 1, 4 and 7 after cell seeding calculated based on live/dead images. (FIG. 4D) Quantification of metabolic activity by PrestoBlue™ at day 1, 4 and 7 after cell seeding ($*p<0.05$, $****p<0.0001$).

(FIG. 5A) Macroscopic view on explanted ELP hydrogels 0, 7, 14, 28 and 56 days after implantation (scale bars=5 mm). (FIG. 5B) The in vivo degradation profile of ELP hydrogels (n=5) over time based on dry weight measurements shows a significant gain in weight at day 56. (FIG. 5C) Hematoxylin/eosin staining of subcutaneously implanted ELP hydrogels at postoperative days 7 (i), 14 (ii), 28 (iii) and 56 (iv) revealed progressive growth of host tissue onto the implants, shown by the arrows (scale bars=200 μm). (FIG. 5D) Immunostaining of subcutaneously implanted ELP hydrogels at days 7 and 28 resulted in no local lymphocyte infiltration (CD3), and relevant macrophage detection (CD68) only at day 7 having disappeared by day 28 (scale bars=100 μm). Green color in (FIG. 5D) represents the autofluorescent ELP, red color the immune cells, and blue color all cell nuclei (DAPI) ($***p<0.001$).

(FIG. 6A) A schematic of combining silica nanoparticle (NP; Ludox®) solutions with the photocrosslinked ELPs. FIG. 6A discloses "KCTS-$E_{31}$-KCTS" in reference to SEQ ID NO: 7. (FIG. 6B) A 96 well plate clotting time assay shows decreased clotting times when NP solutions are combined with the photocrosslinked ELPs. (FIG. 6C) Clotting times measured from the 96 well plate clotting time assay. (FIG. 6D) A schematic of placement of NP-coated ELP hydrogels on an otherwise lethal liver wound. (FIG. 6E) In vivo blood loss after application of ELP versus ELP with NP coating ($p<0.01$, $*p<0.001$).

DETAILED DESCRIPTION

Figures 1A, 1B, 1C, 1D:
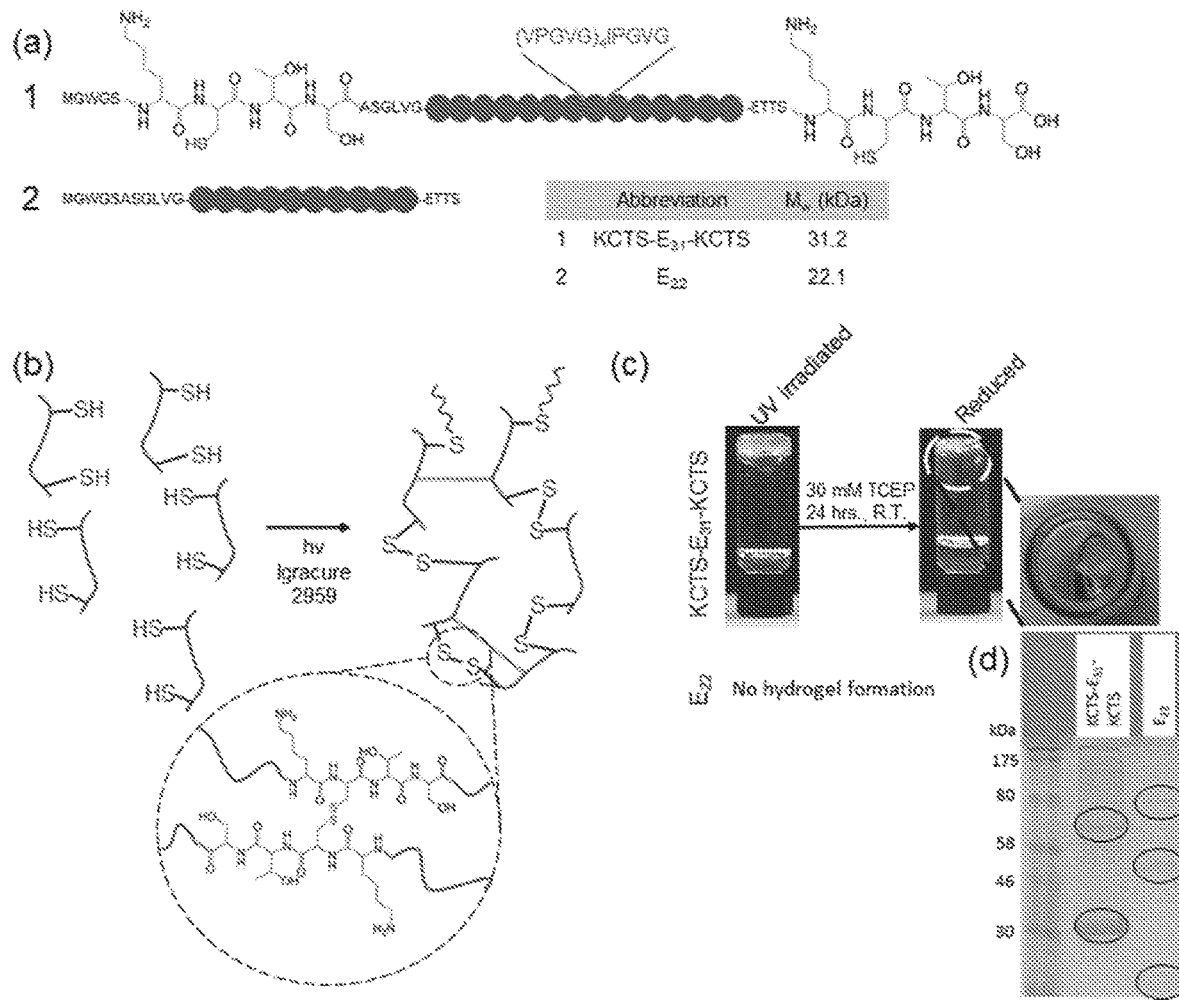
FIGS. 1A-1D show design and photocrosslinking of elastin-like polypeptides (ELPs).

The technology described herein is based, at least in part, on the discovery of certain engineered elastin-like polypeptides (ELPs) that can crosslink to form biocompatible hydrogels with desirable mechanical properties. Specifically, the ELPs comprise a plurality of repeats of $[VPGVG]_m IPGVG$ (SEQ ID NO: 8), where m is an integer greater than 1. In some embodiments, the ELPs can undergo rapid polymerization, e.g., no more than a few minutes. The mechanical properties of the hydrogels can be tuned by changing the number of the repeats of [VPGVG]$_m$IPGVG (SEQ ID NO: 8), the concentration of the polypeptide, the degree of crosslinking, concentration of the photoinitiator, among others. In particular, the hydrogels described herein exhibit high extensibility, for example, up to 450% for some hydrogels tested. The extensibility can be at least 2-3 fold higher than that of other hydrogels based on ELPs, such as those described in E. R. Welsh and D. A. Tirrell, *Biomacromolecules*, vol. 1, pp. 23-30, 2000, and K. Di Zio and D. A. Tirrell, *Macromolecules*, vol. 36, pp. 1553-1558, 2003.

The polypeptides and hydrogels described herein can be used in a variety of biomedical applications. In some embodiments, the polypeptides and hydrogels described herein can be used in tissue engineering. For example, the hydrogels can be utilized as tissue scaffolds. The high extensibility makes these hydrogels especially useful as implants in soft and elastic tissues such as blood vessels, skin, lung, cartilage, nucleus pulposus, bladder, muscle tissues and cardiac tissues. The hydrogels described herein can also be utilized as sealants to manage or stop uncontrolled bleeding. Due to the ability of the polypeptides to rapidly polymerize, solutions comprising the polypeptides can be injected in a defect tissue site and then be polymerized locally to function as a filler. The polypeptides and hydrogels described herein can also be used as tissue adhesives, implant coatings, growth factor delivery vehicles, and fillers for cosmetic applications.

In one aspect, the technology described herein relates to a polypeptide comprising an amino acid sequence of {[VPGVG]$_m$IPGVG}$_n$ (SEQ ID NO: 9), where m and n are integers greater than 1. In some embodiments, m is in the range of 1 to 10. In some embodiments, m is in the range of 2 to 8. In some embodiments, m is in the range of 3 to 6. In some embodiments, m is 3. In some embodiments, m is 4. In some embodiments, m is 5.

In some embodiments, n is in the range of 2 to 50. In some embodiments, n is in the range of 2 to 30. In some embodiments, n is in the range of 2 to 20. In some embodiments, n is in the range of 5 to 50. In some embodiments, n is in the range of 5 to 30. In some embodiments, n is in the range of 5 to 20. In some embodiments, n is in the range of 10 to 50. In some embodiments, n is in the range of 10 to 30. In some embodiments, n is in the range of 10 to 20. In some embodiments, n is in the range of 10 to 14. In some embodiments, n is about 14. Without wishing to be bound by theory, as the molar mass of the polypeptide increases, the transition temperature decreases until it plateaus and the modulus increases.

In some embodiments, m is 4 and n is 14.

In some embodiments, the polypeptide further comprises a first cysteine-containing peptide linked to a first side of the amino acid sequence of {[VPGVG]$_m$IPGVG}$_n$ (SEQ ID NO: 9). Without wishing to be bound by theory, the first cysteine-containing peptide can promote crosslinking of the polypeptides. The first cysteine-containing peptide can have no more than 10 amino acids, e.g., 9, 8, 7, 6, 5, 4, 3, or 2 amino acids. In some embodiments, the first cysteine-containing peptide comprises an amino acid sequence of KCTS (SEQ ID NO: 6). KCTS (SEQ ID NO: 6) can be linked to the first side of the amino acid sequence of {[VPGVG]$_m$IPGVG}$_n$ (SEQ ID NO: 9) through either the amino acid K or S.

In some embodiments, the polypeptide further comprises a second cysteine-containing peptide linked to a second side of the amino acid sequence of {[VPGVG]$_m$IPGVG}$_n$ (SEQ ID NO: 9). The second cysteine-containing peptide can have no more than 20 amino acids, e.g., 20, 19, 18, 17, 16, 15, 14, 13, 12, 11, 10, 9, 8, 7, 6, 5, 4, 3, or 2 amino acids. In some embodiments, the second cysteine-containing peptide comprises an amino acid sequence of KCTS (SEQ ID NO: 6). KCTS (SEQ ID NO: 6) can be linked to the second side of the amino acid sequence of {[VPGVG]$_m$IPGVG}$_n$ (SEQ ID NO: 9) through either the amino acid K or S.

In some embodiments, the polypeptide comprises an amino acid sequence of KCTS{[VPGVG]$_4$IPGVG}$_{14}$KCTS (SEQ ID NO: 7). In some embodiments, the polypeptide comprises an amino acid sequence of STCK{[VPGVG]$_4$IPGVG}$_{14}$KCTS (SEQ ID NO: 10).

In some embodiments, the polypeptide can further comprise a cell-recognition peptide to promote cell adhesion and/or spreading. In some embodiments, the cell adhesion peptide has a length of 40 amino acids or less, 35 amino acids or less, 30 amino acids or less, 25 amino acids or less, or 20, 19, 18, 17, 16, 15, 14, 13, 12, 11, 10, 9, 8, 7, 6, or 5 amino acids or less. Cell-recognition peptides are known in the art include, but are not limited to, RGD, CGGNGEPRGDTYRAY (SEQ ID NO: 11), KGD, amyloid peptide, PECAM, NGR, KQAGDV (SEQ ID NO: 12), LDV, IDS, RLD/KRLDGS (SEQ ID NO: 13), L/IET, YYGDLR (SEQ ID NO: 14), FYFDLR (SEQ ID NO: 15), CRRETAWAC (SEQ ID NO: 16), ACDCRGDCFCG (SEQ ID NO: 17), and YGYYGDALR (SEQ ID NO: 18). More examples of cell-recognition peptides can be found, e.g., in E. Ruoslahti Annu. Rev. Cell Dev. Biol. 1996, 12:697-715. The polypeptides comprising cell-recognition peptides are useful to form hydrogels as tissue scaffolds.

The polypeptides disclosed herein can be produced by any suitable methods such as recombinant genetic engineering, chemical synthesis, and cell-free translation.

For example, the polypeptides can be produced using conventional recombinant nucleic acid technology. Generally, the nucleic acid molecule (DNA or RNA, preferably DNA) is incorporated into a vector-expression system of choice to prepare a nucleic acid construct using standard cloning procedures known in the art, such as those described by Joseph Sambrook & David W. Russell, Molecular Cloning: a Laboratory Manual (3d ed. 2001), Cold Spring Harbor Press; Ausubel et al. (eds.), 1994, Current Protocols in Molecular Biology, John Wiley & Sons, Inc.; Innis et al. (eds.), 1990 PCR Protocols, Academic Press. The nucleic acid molecule may be inserted into a vector in the sense (i.e., 5' to 3') direction, such that the open reading frame is properly oriented for the expression of the encoded protein under the control of a promoter of choice. Single or multiple nucleic acids may be ligated into an appropriate vector in this way, under the control of a suitable promoter, to prepare a nucleic acid construct for expressing a polypeptide of the present invention. Alternatively, the nucleic acid molecule may be inserted into the expression system or vector in the antisense (i.e., 3' to 5') orientation. The vector should also contain the necessary elements for the transcription and translation of the inserted polypeptide-coding sequences.

Once the isolated nucleic acid molecule encoding the polypeptide has been cloned into an expression system, it is ready to be incorporated into a host cell. Recombinant molecules can be introduced into cells using any approach suitable for the selected host cells, including, but not limited to, transduction, conjugation, lipofection, protoplast fusion, mobilization, particle bombardment, electroporation, polyethylene glycol-mediated DNA uptake, or fusion of protoplasts with other entities (e.g., minicells, cells, lysosomes, or other fusible lipid-surfaced bodies that contain the chimeric gene). Suitable hosts include, but are not limited to bacteria, virus, yeast, fungi, mammalian cells, insect cells, plant cells, and the like.

The host cell is then cultured in a suitable medium, and under conditions suitable for expression of the polypeptide of interest. After cultivation, the cell is disrupted by physical or chemical means, and the polypeptide purified from the resultant crude extract. Alternatively, cultivation may include conditions in which the polypeptide is secreted into the growth medium of the recombinant host cell, and the polypeptide is isolated from the growth medium. Alternative methods may be used as suitable.

The polypeptides can also be synthesized in a cell-free protein synthesis system. The above expression vector DNA can be transcribed in vitro, and the resultant mRNA is added to a cell-free translation system to synthesize the protein. Specifically, the cell-free translation system can be prepared from an extract of a eukaryotic cell or a bacterial cell, or a portion thereof. Such cell-free translation systems include, but are not limited to those prepared from rabbit reticulocytes, wheat germ, and E. coli S30 extract.

Alternatively, the polypeptides can be obtained directly by chemical synthesis, e.g., using a commercial peptide synthesizer according to the vendor's instructions. Such a synthesis is carried out using known amino acid sequences for the polypeptides of the present invention. These polypeptides can then be separated by conventional procedures (e.g., chromatography, SDS-PAGE). Methods and materials for chemical synthesis of polypeptides are well known in the art. See, e.g., Merrifield, 1963, "Solid Phase Synthesis," J. Am. Chem. Soc. 83:2149-2154.

The polypeptides described herein can also be produced by a commercial producer such as GeneScript, Life Technologies, and Neo Scientific.

Once produced, the polypeptides of the present invention may be purified by methods that will be apparent to one of skill in the art including, but not limited to, liquid chromatography such as normal or reversed phase, HPLC, FPLC and the like; affinity chromatography (such as with inorganic ligands or monoclonal antibodies); ion exchange chromatography, size exclusion chromatography; immobilized metal chelate chromatography; and gel electrophoresis. Polypeptide purification can be enhanced by adding a group to the carboxyl or amino terminus to facilitate purification. Examples of groups that can be used to facilitate purification include polypeptides providing affinity tags. Examples of affinity tags include a six-histidine-tag, trpE, glutathione S-transferase, and maltose-binding protein. To maintain the properties of the polypeptide composition, it can be advantageous to provide cleavage sites that permit removal of affinity tags, particularly if larger tags such as glutathione S-transferase or maltose-binding protein are used.

A variety of methods can be applied to polymerize the polypeptides described herein. These methods include, but are not limited to, photoinitiation, Michael addition, and other thiol reactions.

In some embodiments, to initiate polymerization of the polypeptides described herein, light can be applied to the polypeptides in the presence of a photoinitiator for a period of seconds to several minutes or hours. For example, the light can be applied for about 10 seconds to about 5 minutes. In certain embodiments, light is applied for about 1 minute to about 5 minutes. The light source can allow variation of the wavelength of light and/or the intensity of the light.

In some embodiments, the wavelength of the light irradiating the polypeptides is ultraviolet (i.e., in the range of 400 nm to 10 nm). A UV photoinitiator is a reactive material that is configured to produce a polymerizing radical when exposed to a specific UV wavelength of light. The free radical is then configured to polymerize the polypeptides. Exemplary UV photoinitiators include, but are not limited to, alpha-hydroxy ketones, alpha-amino ketones, bis-acylphosphine oxide (BAPO) initiators, benzophenone, acrylated amine synergists, and alpha-hydroxy propanones. In one embodiment, the UV photoinitiator is 1-[4-(2-Hydroxyethoxy)-phenyl]-2-hydroxy-2-methyl-1-propane-1-one. The UV photoinitiator can be commercially manufactured by Ciba® under the trade name IRGACURE® or DAROCUR®, specifically "IRGACURE" 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl) phosphine oxide and 2-hydroxy-2-methyl-1-phenyl-propan-1-one), and "DAROCUR" 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one). In addition, alkyl pyruvates, such as methyl, ethyl, propyl, and butyl pyruvates, and aryl pyruvates, such as phenyl, benzyl, and appropriately substituted derivatives thereof may be used as well. Combinations of these materials may also be employed herein.

In some embodiments, the wavelength of the light irradiating the polypeptides is visible (i.e., in the range of 401 nm to 700 nm). Exemplary photoinitiators that work in the visible range include, but are not limited to, Eosin Y, bis(2,4,6-trimethyl benzoyl) phenyl phosphine oxide, bis ($\eta^5$-2,4-cyclopentadien-1-yl)-bis-[2,6-difluoro-3-(1H-pyrrol-1-yl)phenyl]titanium, quinones such as camphorquinone and fluorones.

The photoinitiator may be used in an amount of from about 0.5 to about 10% by weight of the total composition, such as about 2 to about 6% by weight.

Because cysteine comprises a thiol group, in some embodiments, Michael addition can be used to polymerize the polypeptides described herein. In these embodiments, a Michael acceptor can be used to crosslink the polypeptides. In some embodiments, a 4-arm polyethylene glycol (PEG) can be used in a Michael addition reaction (e.g., Michael-type addition reaction between vinyl sulfone groups of 4-arm PEG and cysteine residues). In some embodiments, other thiol reactions can be used. For example, thiol-reactive homobifunctional crosslinkers (e.g., bis-((N-iodoacetyl)piperazinyl)sulfonerhodamine) can be used to crosslink the polypeptides.

A hydrogel can be formed after the polymerization of the polypeptides described herein. In some embodiments, the polypeptide is present at a concentration between 5% and 50% (w/v), e.g., between 5% and 40% (w/v), between 5% and 35% (w/v), between 5% and 30% (w/v), between 5% and 20% (w/v), between 10% and 30% (w/v), between 10% and 25% (w/v), or between 10% and 20% (w/v).

The degree of cross-linking in the hydrogel can also affect its properties. Accordingly, the degree of cross-linking can range from 0% (i.e., no cross-linking) to 100% (i.e. all groups available for cross-linking are used). In some embodiments, the degree of cross-linking is in the range of from about 5% to about 95%, from about 10% to about 90%, from about 15% to about 80%, from about 20% to about 75%, or from about 25% to about 50%. In some embodiments, the degree of cross-linking is 5% or less. In some embodiments, the degree of cross-linking can range from about 0.1% to about 20%. In some embodiments, the degree of cross-linking can range from about 1% to about 5%.

The hydrogels described herein exhibit tunable physical properties including pore size, swelling ratio, and mechanical properties. The physical properties can be tuned by changing the concentration of the polypeptide and/or the degree of cross-linking.

The mechanical properties of the hydrogels can be characterized by any one or more of properties including, e.g., extensibility, strain at fracture, elastic modulus, shear modulus, tensile strength, compressive modulus, energy loss, and stiffness. Energy loss is proportional to hysteresis, this mean that material with higher elasticity have lower energy loss, it is calculated based on the area between loading and unloading curve after performing cyclic test using the below formula: energy loss=(area under loading curve−area under unloading curve)/(area under loading curve)×100%.

While optimal properties will vary for any given application of the hydrogels described herein, the elastic hydrogels will generally have an extensibility of at least 100%. In some embodiments, the extensibility of the hydrogels is up to 600%. In some embodiments, the extensibility of the hydrogels is up to 550%. In some embodiments, the extensibility of the hydrogels is up to 500%. In some embodiments, the extensibility of the hydrogels is up to 450%. As used herein, the terms "extensibility" and "strain at failure" are used interchangeably. The extensibility of the hydrogels can be tuned, for example, by changing the photoinitiator concentration and/or ELP concentration. Generally stiffer hydrogel has less extensibility. Lowering the concentration of ELP can provide softer but more elastic gel.

In some embodiments, the elastic modulus of the hydrogels is in the range of 0.5-15 kPa. In some embodiments, the elastic modulus of the hydrogels is in the range of 0.5-10 kPa. In some embodiments, the elastic modulus of the hydrogels is in the range of 0.5-8 kPa. In some embodiments, the elastic modulus of the hydrogels is in the range of 0.5-6 kPa. In some embodiments, the elastic modulus of the hydrogels is in the range of 0.5-4 kPa. In some embodiments, the elastic modulus of the hydrogels is in the range of 0.5-3 kPa. In some embodiments, the elastic modulus of the hydrogels is in the range of 0.5-2.5 kPa. In some embodiments, the elastic modulus of the hydrogels is in the range of 1-3 kPa. In some embodiments, the elastic modulus of the hydrogels is in the range of 1-2.5 kPa. At least in some concentration range (e.g., 5-30% w/v), the elastic modulus can be increased by increasing the concentration of the polypeptide in the hydrogel.

In some embodiments, the tensile strength of the hydrogel is in the range of 4-20 kPa. In some embodiments, the tensile strength of the hydrogel is in the range of 4-15 kPa. In some embodiments, the tensile strength of the hydrogel is in the range of 5-15 kPa. In some embodiments, the tensile strength of the hydrogel is in the range of 6-12 kPa. At least in some concentration range (e.g., 5-30% w/v), the tensile strength can be increased by increasing the concentration of the polypeptide in the hydrogel.

In some embodiments, the compressive modulus of the hydrogel is in the range of 1-20 kPa. In some embodiments, the compressive modulus of the hydrogel is in the range of 2-18 kPa. In some embodiments, the compressive modulus of the hydrogel is in the range of 3-15 kPa. In some embodiments, the compressive modulus of the hydrogel is in the range of 3-12 kPa. At least in some concentration range (e.g., 5-30% w/v), the compressive modulus can be increased by increasing the concentration of the polypeptide in the hydrogel.

In some embodiments, the hydrogels described herein comprise a plurality of pores. In some embodiments, the hydrogel has a porosity of at least about 10%, at least about 20%, at least about 30%, at least about 40%, at least about 50%, at least about 60%, at least about 70%, at least about 80%, at least about 90%, or higher. The term "porosity" as used herein is a measure of void spaces in a material, e.g., a matrix such as a hydrogel described herein, and is a fraction of volume of voids over the total volume, as a percentage between 0 and 100% (or between 0 and 1). Determination of porosity is well known to a skilled artisan, e.g., using standardized techniques, such as mercury porosimetry and gas adsorption, e.g., nitrogen adsorption.

The porous hydrogel can have a wide range of pore size. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. In some embodiments, the porous hydrogel has an average pore size in the range of 100 nm to 100 μm, 100 nm to 50 μm, 100 nm to 20 μm, 100 nm to 10 μm, or 500 nm to 5 μm.

In some embodiments, the hydrogels described herein can absorb water and increase in volume. This swelling property can be characterized by the swelling ratio. The swelling ratio can be calculated via the following equation: $S_r = (W_w - W_d)/W_d$, where $S_r$ is the equilibrium swelling ratio, $W_w$ is the swollen weight of the hydrogel after equilibrium in PBS and $W_d$ is the dry weight of the hydrogel dried by lyophilization. The swelling ratio for the same material can be different at different temperatures, so the swelling ratio is typically specified at a specific temperature. In some embodiments, the hydrogel can have a swelling ratio at 37° C. of at least 50%, at least 60%, at least 70%, at least 80%, at least 90%, at least 100%, at least 150%, or at least 200%. In some embodiments, the hydrogel can have a swelling ratio at 37° C. of no more than 500%.

In some embodiments, the hydrogels described herein are minimally degraded after a period of time (e.g., at least 7 days, at least 14 days, at least 28 days, or at least 56 days) when implanted in a subject. Stated another way, the hydrogels described herein show slow degradation rate. Generally, hydrogels with lower ELP concentration have higher degradation rates.

In some embodiments, the hydrogels described herein can comprise a bioactive agent. Without limitations, a bioactive agent can be selected from small organic or inorganic molecules; saccharides; oligosaccharides; polysaccharides; biological macromolecules, e.g., peptides, proteins, and peptide analogs and derivatives, polyclonal antibodies and antigen binding fragments thereof, monoclonal antibodies and antigen binding fragments thereof; peptidomimetics; nucleic acids and nucleic acid analogs and derivatives (including but not limited to siRNAs, shRNAs, antisense oligonucleotides, ribozymes, and aptamers); an extract made from biological materials such as bacteria, plants, fungi, or animal cells; animal tissues; naturally occurring or synthetic compositions; and any combinations thereof.

Exemplary bioactive agents include, but are not limited to, vitamins, anti-cancer substances, antibiotics, immunosuppressants, anti-viral substances, enzyme inhibitors, opioids, hypnotics, lubricants, tranquilizers, anti-convulsants, muscle relaxants, anti-spasmodics and muscle contractants, anti-glaucoma compounds, modulators of cell-extracellular matrix interactions including cell growth inhibitors and anti-adhesion molecules, vasodilating agents, analgesics, anti-pyretics, steroidal and non-steroidal anti-inflammatory agents, anti-angiogenic factors, anti-secretory factors, anti-coagulants and/or antithrombotic agents, local anesthetics, ophthalmics, prostaglandins, anti-depressants, anti-psychotic substances, anti-emetics, imaging agents. A more complete, although not exhaustive, listing of classes and specific drugs suitable for use in the present invention can be found in "Pharmaceutical Substances: Synthesis, Patents, Applications" by A. Kleeman and J. Engel, Thieme Medical Publishing, 1999; Harrison's Principles of Internal Medicine, 13th Edition, Eds. T. R. Harrison et al. McGraw-Hill N.Y., NY; Physicians' Desk Reference, 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's The Pharmacological Basis of Therapeutics; and the current edition of "Merck Index: An Encyclopedia of Chemicals, Drugs, and Biologicals", S. Budavari et al. (Eds), CRC Press, contents of all of which are incorporated herein by reference in their entireties.

The bioactive agent can be dispersed homogeneously or heterogeneously within the hydrogel, or dispersed in a gradient. Bioactive agent can be present in the hydrogel in a range of amounts or concentrations. For example, in some embodiments, an bioactive agent can be present in the hydrogel at a concentration of about 0.001 wt % to about 50 wt %, about 0.005 wt % to about 40 wt %, about 0.01 wt % to about 30 wt %, about 0.05 wt % to about 20 wt %, about 0.1 wt % to about 10 wt %, or about 0.5 wt % to about 5 wt %.

A hydrogel comprising a bioactive agent can be produced by polymerizing the polypeptides described herein in the presence of the bioactive agent. Alternatively, a hydrogel comprising a bioactive agent can be produced by immersing a hydrogel in a solution comprising the bioactive agent.

In some embodiments, the bioactive agent is a hemostatic agent. Hemostatic agents are used in surgical, emergency, and combat situations to manage uncontrolled bleeding by one or more hemostatic mechanisms. Exemplary hemostatic mechanisms include, but are not limited to, release of clotting factors, absorption of fluid, and sealing. Examples of hemostatic agents include, but are not limited to, silica nanoparticles (e.g., Ludox® TM-50), blood coagulation factors, prothrombin, thrombin, fibrinogen, fibrin, gelatin, collagen, polysaccharide, aminocaproic acid, tranexamic acid, aprotinin, desmopressin, ferric sulfate, fibrin sealant, and cellulose. The use of silica nanoparticles (e.g., Ludox® TM-50) as hemostatic agents can be found, e.g., in A. Meddahi-Pelle, et al., Angew. Chem. Int. Ed., 53, 6369 (2014).

In some embodiments, the bioactive agent is an antibacterial agent. Examples of antibacterial agents include, but are not limited to, silver nanoparticles, copper oxide nanoparticles, nanoparticle-carried antibiotic drugs, penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, and sulfamethoxazole.

In some embodiments, the hydrogel can comprise one or more cells.

The hydrogel can be used in a range of forms, shapes or sizes, such as a film, a sheet, a gel or hydrogel, a mesh, a mat, a non-woven mat, a fabric, a scaffold, a tube, a slab or block, a fiber, a particle, powder, a 3-dimensional construct, an implant, a foam or a sponge, a needle, a high density material, a lyophilized material, and any combinations thereof. In some embodiments, the hydrogel can be further processed into a variety of desired shapes. Examples of such processing methods include, but are not limited to, machining, turning (lathe), rolling, thread rolling, drilling, milling, sanding, punching, die cutting, blanking, broaching, and any combinations thereof.

In some embodiments, the polypeptide compositions and hydrogels described herein can be sterilized. Sterilization methods for biomaterials are well known in the art, including, but not limited to, gamma or ultraviolet radiation; alcohol sterilization (e.g., ethanol and methanol); and gas sterilization (e.g., ethylene oxide sterilization).

Depending on the particular application, the polypeptides described herein can be present in a range of concentrations in the hydrogel to achieve desired structural, mechanical and/or degradation properties.

The hydrogels described herein can be used as tissue scaffolds. The high extensibility makes the hydrogels particularly useful for treating soft tissue injuries. In some embodiments, the tissue scaffold is engineered to have similar mechanical properties as the soft tissue in which the scaffold is implanted. Soft tissues include, but are not limited to, blood vessels, skin, lung, cartilage, nucleus pulposus, bladder, muscle tissues, and cardiac tissues.

The hydrogels described herein can also be used as sealants to treat uncontrolled bleeding.

Other applications include, but are not limited to, injectable filler, tissue adhesive, implant coating, growth factor delivery, and filler for cosmetic applications. Exemplary growth factors include TGF-β, Wnt, EGF, VEGF, HGF, and FGF.

Additionally, the hydrogels described herein can be in the form of a substrate for flexible electronics. Electronic or photonic devices can be disposed on the hydrogel substrate for interfacing with a soft tissue.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although any known methods, devices, and materials may be used in the practice or testing of the invention, the methods, devices, and materials in this regard are described herein.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein, the term "comprising" or "comprises" is used in reference to compositions, methods, and respective component(s) thereof, that are useful to an embodiment, yet open to the inclusion of unspecified elements, whether useful or not.

As used herein, the term "consisting essentially of" refers to those elements required for a given embodiment. The term permits the presence of elements that do not materially affect the basic and novel or functional characteristic(s) of that embodiment of the invention.

As used herein, the terms "proteins" and "polypeptides" are used interchangeably to designate a series of amino acid residues connected to each other by peptide bonds between the alpha-amino and carboxy groups of adjacent residues. The terms "protein" and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "hydrogel" refers to a three-dimensional polymeric structure that is insoluble or minimally soluble in water or some other liquid but which is capable of absorbing and retaining large quantities of water or some other liquid to form a stable, often soft and pliable, structure.

As used herein, the term "biodegradable" describes a material which can decompose partially or fully under physiological conditions into breakdown products. The material under physiological conditions can undergo reactions or interactions such as hydrolysis (decomposition via hydrolytic cleavage), enzymatic catalysis (enzymatic degradation), and mechanical interactions. As used herein, the term "biodegradable" also encompasses the term "bioresorbable," which describes a substance that decomposes under physiological conditions, breaking down to products that undergo bioresorption into the host-organism, namely, become metabolites of the biochemical systems of the host organism. For example, a material is biodegradable if at least 10%, at least 20%, at least 30%, at least 40%, or more preferably, at least 50%, at least 60%, at least 70%, at least 80%, at least 90% of the material can decompose under physiological conditions within a desired period of time, such as on the order of minutes, hours, days, weeks, or months, depending on the exact material.

As used herein, the term "physiological conditions" refer to conditions of temperature, pH, osmotic pressure, osmolality, oxidation and electrolyte concentration in vivo in a human patient or mammalian subject at the site of administration, or the site of action. For example, physiological conditions generally mean pH at about 6 to 8 and temperature of about 37° C. in the presence of serum or other body fluids.

As used herein, the term "biocompatible" denotes being biologically compatible by not producing a toxic, injurious, or immunological response in living tissue.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, rabbits, deer, bison, buffalo, goats, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "individual," "patient," "subject," and the like are used interchangeably herein. The terms do not denote a particular age, and thus encompass adults, children, and newborns. A subject can be a male or female.

Preferably, the subject is a mammal. The mammal can be a human, non-human primate, mouse, rat, dog, cat, horse, or cow, but is not limited to these examples. Mammals other than humans can be advantageously used as subjects in animal models of human treatment or disease. In addition, the methods and compositions described herein can be used for treatment of domesticated animals and/or pets. A human subject can be of any age, gender, race or ethnic group. In some embodiments, the subject can be a patient or other subject in a clinical setting. In some embodiments, the subject can already be undergoing treatment.

As used herein, the terms "treat," "treatment," "treating," or "amelioration" are used herein to characterize a method or process that is aimed at (1) delaying or preventing the onset of a disease or condition; (2) slowing down or stopping the progression, aggravation, or deterioration of the symptoms of the disease or condition; or (3) bringing about ameliorations of the symptoms of the disease or condition. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also slowing of progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased morbidity or mortality. The term "treatment" of a disease also includes providing relief from the symptoms or side-effects of the disease (including palliative treatment). A treatment can be administered prior to the onset of the disease, for a prophylactic or preventive action. Alternatively or additionally, the treatment can be administered after initiation of the disease or condition, for a therapeutic action.

As used herein, the term "soft tissue" includes all tissue of the body except bone. Examples of soft tissue include, but are not limited to, muscles, tendons, fibrous tissues, fat, blood vessels, nerves, and synovial tissues.

As used herein, the term "wound" is used to describe skin wounds as well as tissue wounds. A skin wound is defined herein as a break in the continuity of skin tissue that is caused by direct injury to the skin. Several classes including punctures, incisions, excisions, lacerations, abrasions, atrophic skin, or necrotic wounds and burns generally characterize skin wounds. In some embodiments, the compositions and methods of the invention are useful for enhancing the healing of wounds of the skin.

The terms "bioactive agent" and "biologically active agent" are used herein interchangeably. They refer to compounds or entities that alter, inhibit, activate or otherwise affect biological events.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology described herein is further illustrated by the following examples which in no way should be construed as being further limiting.

Example 1: A Highly Elastic and Rapidly Crosslinkable Elastin-Like Polypeptide-Based Hydrogel for Biomedical Applications Methods Protein Synthesis.

A modified ELP was engineered by inserting a designed ELP sequence into a modified pET-28 plasmid containing NheI and SpeI restriction enzyme sites as well the amino acid sequence Lys-Cys-Thr-Ser (SEQ ID NO: 6) flanking the ELP. First, oligomers encoding for these residues were acquired (Sigma), which had the following nucleotide sequences,

```
                                               (SEQ ID NO: 20)
5' to 3'
gatccaaatgtaccagcgctagcagtgtctaacgactagtaaatgcacg
tcttaaa
and (SEQ ID NO: 21)
3' to 5'
agatttaagacgtgcatttactagtcgttagacactgctagcgctggta
catttg.
```

This sequence contained BamHI, HindIII, SpeI, and NheI restriction sites. The oligomers were annealed together and ligated into a modified pET vector, cut with BamHI and HindIII. After confirming correct ligation by sequencing, a digest with NheI and SpeI was performed to allow for the insertion of the ELP sequence, $E_{14}$, also cut from a pET vector with NheI and SpeI. Following ligation, the sequence-confirmed plasmid was transformed into TurnerDE3 expression cells (New England Biolabs). A 50 mL starter culture of the expression E. coli cells in LB media was incubated overnight at 37° C., followed by inoculation of a 5 L fermentation in Terrific Broth. Fermentation was allowed to proceed for 14 h at 30° C. in a fermenter. Filtered air was delivered to the culture for appropriate aeration, and propellers used for agitation. Cell pellets were initially centrifuged and frozen at −80° C. overnight. The cell pellets were suspended at a concentration of 100 mL buffer per 30 g cell pellet mass, on ice, in buffer (100 mM Tris, 100 mM NaCl, 5 mM $MgCl_2$, 1 mM EDTA, 14.3 mM BME) adjusted to pH=7.5. Lysozyme (1 mg/mL buffer) was added for 30 min followed by sonication. The solution was then purified by inverse transition cycling (ITC). The solution was centrifuged at 4° C. and the supernatant was decanted from the pelleted cell debris. DNase and RNase was added to the supernatant and the solution was incubated at 37° C. for 1 h. The solution was centrifuged for 1 h at 37° C. and the supernatant was decanted from the pelleted ELPs, which were suspended in cold buffer and allowed to dissolve at 4° C. overnight. The process was continued, with aliquots taken of each supernatant after spinning at hot (37° C.) and cold (4° C.) temperatures for analysis by denaturing SDS-PAGE, stained with Coomassie Blue dye. After ITC, the buffered solution was dialyzed against 4 L of water for 21 h, exchanging the water every 3 h. Dialyzed solutions were then freeze dried and stored in sealed centrifuge tubes until use.

Hydrogel Fabrication.

Lyophilized ELP was dissolved in phosphate-buffered saline (PBS) containing 0.5% (w/v) 2-hydroxy-1-(4-(hydroxyethoxy) phenyl)-2-methyl-1-propanone (Irgacure® 2959, CIBA Chemicals). To avoid coacervation and precipitation of ELP prior to crosslinking, ELP solutions at defined concentrations were mixed and stored on ice. 90 μL of ELP solution was placed in pre-manufactured polydimethylsiloxane (PDMS) molds (15 mm×6 mm×1 mm). Solutions were photocrosslinked with UV light (80 mm sample-source distance, OmniCure S2000, 360-480 nm wavelength, 850 mW) for 3 min. Samples were then collected from the molds and detached after soaking in PBS for 2 min to ensure easy removal from the mold.

Reduced Protein Gel.

A 10% (w/v) photocrosslinked ELP gel was incubated in a 30 mM tris (2-carboxyethyl) phosphine hydrochloride (TCEP) solution overnight at room temperature to reduce all disulfide bonds. The TCEP concentration was a 5-fold molar excess relative to the concentration of cysteine residues. A small solid portion remained after this reduction but the rest of the gel was completely dissolved into the TCEP solution. The resulting solution containing the dissolved gel proteins and TCEP was then dialyzed against pure water, lyophilized, and mixed with a Coomassie Blue loading dye containing 30 mM TCEP. Samples were loaded and run on a 12% SDS-polyacrylamide gel at 200 V for 40 min. The polyacrylamide gel was stained in Coomassie Blue R-250 staining dye and destained in destaining solution (50 vol % double distilled water, 40 vol % ethanol, and 10 vol % acetic acid).

Scanning Electron Microscopy (SEM).

Photocrosslinked ELP hydrogel samples were lyophilized and mounted on aluminum holders. A 30 nm thick gold layer was sputter coated on all samples prior to imaging. Secondary electron imaging was obtained by using a FEI/Philips XL30 FEG SEM at 15 kV. ImageJ software was used to calculate the apparent pore size of the ELP hydrogels after lyophilization. Triplicates of 10, 15 and 20% (w/v) ELP samples were imaged and 30 pores were measured per image for pore size measurement (n=90).

Swelling Ratio.

The swelling ratios of 10, 15 and 20% (w/v) ELP hydrogels were evaluated in PBS at 4° C. and 37° C. Swelling tests were performed as previously reported (Foo CTWP, et al., *Proc Natl Acad Sci* 106, 22067-22072 (2009); Assmann A, et al., *Biomaterials* 35, 7416-7428 (2014)). Briefly, 90 μl of ELP solution was injected into a PDMS mold with a 7 mm diameter and 5 mm depth. The prepolymer solution was exposed to UV light for 3 min. Hydrogels were lyophilized and dry weights were recorded. Next, samples were placed in PBS for different time points (4, 12, 24, 48 h) at 4° C. or 37° C. At each time point, samples were removed from PBS and weighed. The swelling ratio was calculated following the equation: Swelling ratio: $(W_{wet}-W_{dry})/W_{dry} \times 100\%$, where $W_{dry}$ is the weight after lyophilizing and $W_{wet}$ is after removal from PBS. Tests were performed at least in triplicate for each condition.

Mechanical Characterization.

Tensile and compressive cyclic testing of ELP hydrogels were performed using a mechanical tester (Instron model 5542) with a 10 N load cell.

Tensile Test.

For tensile tests, gels were photocrosslinked as described above (dimensions 15 mm×5 mm×1 mm) for tensile tests. The samples were then incubated in PBS for 4 h at 37° C. prior to mechanical testing. The dimensions of the samples were measured with a digital caliper. To minimize dehydration during testing, a humidifier was used surrounding the testing apparatus. The strain rate was 10 mm/min and performed until sample failure. Ultimate tensile stress (stress obtained at the failure point), maximum strain (strain obtained at the failure point), and elastic modulus (the tangent slope of the stress-strain curve, taken from the 0.1-0.3 mm/mm of the strain) were determined.

Compression Test.

ELP samples were prepared using the same molds utilized for swelling tests (7 mm in diameter and 5 mm in depth). Prior to the test, hydrogels were incubated in PBS for 4 h. The compressive strain rate was 10 mm/min and strain level was up to ~70% of the original height. The compression and load were recorded for 10 cycles, after which there was no significant change in the curve shape. The compressive modulus was obtained from the slope during loading on the $8^{th}$ cycle (the tangent slope of the stress-strain curve). The energy loss was calculated for the $8^{th}$ cycle based on the area between the loading and unloading curves, based on the following equation:

$$\text{Energy Loss} = [(\text{Area below loading} - \text{Area below unloading}) \times 100]/(\text{Area below loading})$$

Samples were tested in triplicate for each condition.

Cell Culture.

Mesenchymal stem cells (MSC, from Lonza) and human umbilical vein endothelial cells (HUVECs, from American Type Culture Collection (ATCC)) were used for the in vitro studies. MSCs were cultured in mesenchymal stem cell growth medium (MSC-GM, Lonza) with 10% fetal bovine serum (FBS, Invitrogen), glutamine-penicillin-streptomycin (GPS, Invitrogen). HUVECs were cultured in endothelial basal medium (EBM-2, Lonza) enriched with endothelial growth factors (BulletKit, Lonza) and 100 units/ml penicillin-streptomycin (Gibco, USA). MSCs and HUVECs were cultured in a 5% $CO_2$ humidified incubator at 37° C. Cells were passaged every 3 days and medium changed every other day.

In Vitro 2D Cell Studies.

10 μL of 10% ELP solutions were photocrosslinked for 30 s on 3-(trimethoxysilyl)propyl methacrylate (TMSPMA) coated glass slides using 150 μm spacers. Cells were then seeded on the top of the ELP gels placed in a 24 well plate. The cell seeding density was $1 \times 10^4$ cell/well. Cell viability and proliferation were studied on day 1, 4, and 7 of culture. Medium was changed every other day.

Cell Viability.

Cell viability assays were performed using a Live/Dead kit (Invitrogen, USA) following instructions from the manufacturer. Briefly, ethidium homodimer-1 (2 μl/ml) and calcein AM (0.5 µl/ml) were mixed in PBS and added on cell-seeded ELP scaffolds. The samples were then incubated for 15 min at 37° C. and imaged with an inverted fluorescence microscope (Nikon TE 2000-U, Nikon instruments Inc., USA). ImageJ was used to count the live and dead cells by using at least 4 images from different areas of 3 samples for each ELP condition. Cell viability was calculated by division of the number of live cells by the total number of stained cells.

Metabolic Activity.

Cell activity was measured with PrestoBlue™ reagents (Life Technologies) following the manufacturer's protocol. Each construct was incubated with 400 µl of a solution containing 10% PrestoBlue™ reagent and 90% respective cell media (MSC-GM media for MSCs and EBM-2 for HUVECs) for 2 h at 37° C. The resulting fluorescence was measured at a wavelength of 560 nm (excitation) and 590 nm (emission) with a fluorescence reader (Synergy HT-Reader, BioTek, Winooski, Vt.). By subtracting the fluorescence values from the control (wells without cells), the relative fluorescence values were calculated and plotted for each day, where higher fluorescence values correlate to greater total metabolic activity. Samples were tested in triplicate for each condition.

In Vitro Clotting Tests.

Citrated human blood was mixed with 0.1 M CaCl2 at a ratio of 9:1 to reverse anticoagulation. Following vigorous mixing by vortexing for 1-2 s, 100 µL were aliquoted into 96 well plates with bottoms coated in either Ludox® TM-50 (Sigma) colloidal nanoparticle suspension (labelled Ludox®), 50 µL of 10% photocrosslinked ELP (labelled KCTS-$E_{31}$-KCTS) (SEQ ID NO: 7), 50 µL of 10% photocrosslinked ELP with 10 µL Ludox® TM-50 pipetted on the surface (labelled KCTS-$E_{31}$-KCTS (SEQ ID NO: 7)+Ludox®), or uncoated well plates (labelled Control). At selected time points, individual wells were rinsed with 9 mg/mL saline solution and the liquid aspirated until the solution remained clear, indicating removal of all soluble blood components, and leaving behind only clotted blood. The clotting time was marked as the time in which a uniform clot covered the entire bottom of the well plate.

Animal Experiments.

For all animal experiments, male Wistar rats weighing 200-250 g were obtained from Charles River (Wilmington, Mass., USA) and housed in the local animal care facility of the Partners Research Building (Cambridge, Mass., USA) under conditions of circadian day-night rhythm and feeding ad libitum. Anesthesia was achieved by isoflurane inhalation (2.0-2.5%). All experiments were conducted according to the NIH "Guide for the Care and Use of Laboratory Animals", and approved by the local animal care committee (HMA Standing Committee on Animals; protocol number 05055).

Subcutaneous Implants.

The medio-dorsal skin of rats was incised by 1 cm in length and a small lateral subcutaneous pocket was bluntly prepared. ELP samples (n=20; 1×5 mm disks) were thoroughly implanted under sterile conditions before anatomical wound closure and recovery from anesthesia. At days 3, 14, 28 and 56, euthanasia by $CO_2$ inhalation was followed by explanation of the ELP samples including the adjacent tissue. Afterwards, the samples were processed for histological analyses and degradation studies.

Histology and Immunohistology.

Histological analyses were performed on 6 µm cryosections of the explanted ELP samples. After fixation with paraformaldehyde, hematoxylin and eosin staining was conducted as previously reported (Assmann A, et al., *Biomaterials* 34, 6015-6026 (2013)). Immunohistological staining was performed. As primary antibodies, anti-CD3 and anti-CD68 (Abcam, Cambridge, Mass., USA) were used, and all secondary antibodies were Alexa Fluor®-conjugated (Invitrogen, Carlsbad, USA). Sections were covered with DAPI-enriched Vectashield mounting medium (Vector Labs, Peterborough, United Kingdom) and visualized on an Axio Observer microscope (Zeiss, Jena, Germany).

In Vivo Liver Bleeding.

A median laparotomy was performed and the central liver lobe was visualized by retraction of skin. A 0.5 cm cut was made through the edge of the lobe with straight operating scissors. After removing hemorrhaged blood with dry filter paper, photocrosslinked KCTS-$E_{31}$-KCTS (SEQ ID NO: 7) samples (n=3 animals; 90 µL of 10 wt % KCTS-$E_{31}$-KCTS (SEQ ID NO: 7), 0.5% photoinitiator crosslinked for 180 s) were deposited on the wound with a spatula. Additional samples had Ludox® TM-50 solution (20 µL) added to the top and bottom of KCTS-$E_{31}$-KCTS (SEQ ID NO: 7) photocrosslinked samples (n=3 animals). These were added to the wounds in the same way as KCTS-$E_{31}$-KCTS (SEQ ID NO: 7) samples. After application of the hydrogel, lost blood was absorbed on filter papers for later mass quantification until bleeding ceased. Following this observation, the time was marked and the crosslinked sample was removed to test for subsequent bleeding. Rats were then sacrificed by severing of the aorta.

Statistical Analysis.

Data were compared using one-way or two-way ANOVA methods, depending on the variables in the data set, in GraphPad Prism 6. Data are expressed as means±standard deviation (SD) of measurements (*$p<0.05$, $p<0.01$ and *$p<0.001$).

Results

Expression and Fabrication of ELP Hydrogels.

Figure 7A:
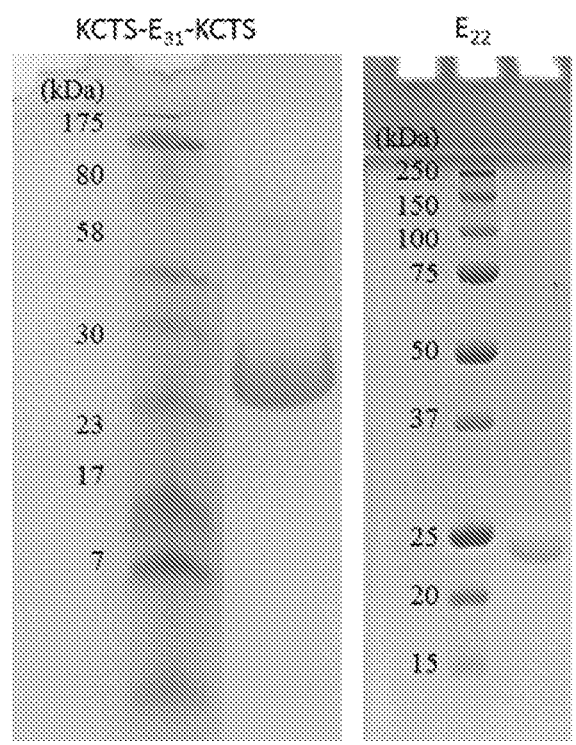
FIG. 7A shows protein gel of KCTS-$E_{31}$-KCTS (SEQ ID NO: 7) and $E_{22}$ proteins after purification.
Figure 7B:
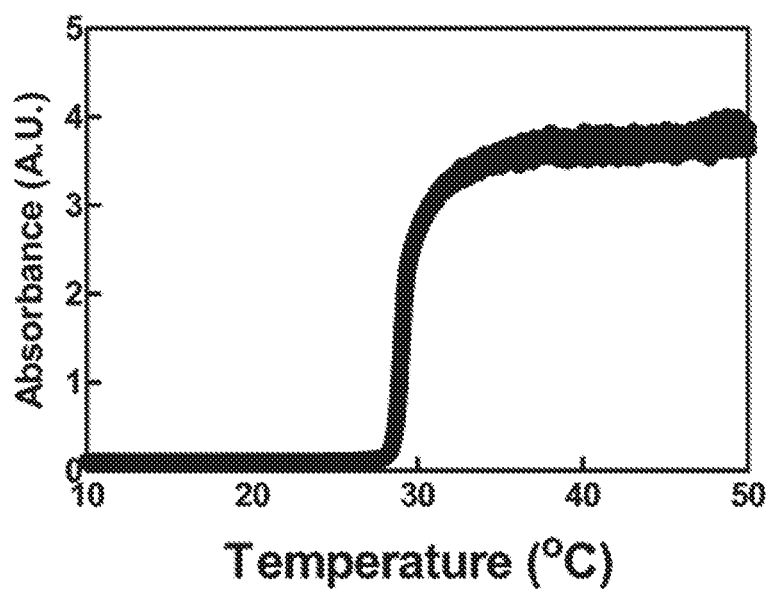
FIG. 7B is UV-Vis plot showing the transition temperature of a 1% (w/v) solution of ELP.

The expression of engineered ELPs in this study were performed by fermentation in *Escherichia coli* (*E. coli*) hosts, followed by lysis and purification by inverse transition cycling (Meyer D E, et al., *Nat Biotech* 17, 1112-1115 (1999)). Briefly, ELP solutions were alternatively equilibrated and centrifuged above (37° C.) and below (4° C.) their LCST (Tt=29° C.) in 1% (w/v) solution. Yields of pure ELP (purity>90%) were 1 g/L for 5 L fermentations (FIGS. 7A-7B). The ELP pentapeptide sequence is composed of the amino acids VPGVG (SEQ ID NO: 22) in which every fifth pentapeptide replaced the first valine with an isoleucine (i.e. [[VPGVG]$_4$IPGVG]$_n$ (SEQ ID NO: 2)). Two polypeptides were expressed: one with the residues Lys-Cys-Thr-Ser (KCTS) (SEQ ID NO: 6) flanking the ELP sequence (named KCTS-$E_{31}$-KCTS (SEQ ID NO: 7)) and the second without any flanking residues (named $E_{22}$) (FIG. 1A). Flanking sequences containing cysteine residues were chosen for their potential to promote chain extension and improve elasticity of the resulting hydrogel (Odian G. *Principles of Polymerization*, Fourth edn (2004)).

In an attempt to produce photocrosslinkable ELP hydrogels, the experiments described herein confirmed that only cysteine-containing ELPs, KCTS-$E_{31}$-KCTS (SEQ ID NO: 7), could be photocrosslinked and form elastic gels following exposure to UV light in the presence of a photoinitiator, Irgacure® 2959 (FIG. 1B). Stable gels were formed between 30 s and 3 min of irradiation depending on their volume, and gelation was confirmed using an inversion test (FIG. 1C). Thiols, present in KCTS-$E_{31}$-KCTS (SEQ ID NO: 7) ELP, are generally used in radical polymerizations as chain transfer agents (Chiou B-S, et al., *Macromolecules* 29, 5368-5374

(1996)). In polymerization, they serve to transfer radicals to initiate new chains (Dénès F, et al., *Chem Rev* 114, 2587-2693 (2014)). However, in the crosslinking of the KCTS-$E_{31}$-KCTS (SEQ ID NO: 7) ELP, it is hypothesized that thiols perform two functions: (a) producing disulfide bonds and (b) generating chain extension (Odian G. *Principles of Polymerization*, Fourth edn (2004)) of the ELP. Following irradiation of the photoinitiator, radicals react first with the S—H bonds, which have the lowest binding dissociation energy in the peptide system (Hawkins C L, Davies M J,. *Biochim Biophys Acta* 1504, 196-219 (2001)). Further crosslinking among residues or backbone groups of the ELP must also occur to produce a hydrogel network, as two thiols per ELP would only result in chain extension. Crosslinks among ELP residues are presumed to occur by transfer of radicals from the photoinitiator, leading to a stable hydrogel network.

To confirm these hypotheses of the crosslinking mechanism, ELPs containing cysteine residues (KCTS-$E_{31}$-KCTS (SEQ ID NO: 7)) and ELPs containing only the pentapeptide repeat ($E_{22}$) were irradiated under identical conditions. Gels were only formed in KCTS-$E_{31}$-KCTS (SEQ ID NO: 7) samples, indicating the inability of the residues in the $E_{22}$ sequence alone to form a photocrosslinked gel. To determine the nature of these crosslinks, photocrosslinked KCTS-$E_{31}$-KCTS (SEQ ID NO: 7) ELP gels were incubated in 30 mM tris (2-carboxyethyl) phosphine hydrochloride (TCEP) solution as an irreversible reducing agent to break disulfide bonds. This procedure resulted in almost complete dissolution of the gel (FIG. 1C), suggesting disulfide bond formation is a factor, but not the only source, of crosslinks in the system. Gel electrophoresis bands around double the molecular weight of KCTS-$E_{31}$-KCTS (SEQ ID NO: 7) and $E_{22}$ were observed after irradiation and complete reduction, indicative of chemically crosslinked ELP dimers (FIG. 1D). Their presence, even after reduction in an excess of reducing agent, indicates that some crosslinking, other than disulfide bonds, persisted in the reduced photocrosslinked ELPs. The nature of these crosslinks is unclear; however, while not wishing to be bound by theory, they may involve peroxyl formation in an oxygen rich environment and hydrogen abstraction from peptide or backbone residues (Davies M J., *Arch Biochem Biophys* 336, 163-172 (1996); Kim S J, et al., *React Funct Polym* 55, 53-59 (2003)). It is speculated that additional radicals, formed by hydrogen abstraction from ELP residues (Hawkins C L, Davies M J., *Biochim Biophys Acta* 1504, 196-219 (2001); Davies M J., *Arch Biochem Biophys* 336, 163-172 (1996)) were produced by radical transfer from the photoinitiator. There was a three-fold molar excess of photoinitiator in the system compared to thiol groups, providing sufficient radicals for rapid reaction of the thiol groups. It is hypothesized that additional crosslinks between moieties (from C—H, O—H, or N—H groups) in the ELP sequence occurred due to the radical transfer from the photoinitiator and those were not reduced when incubated in a reducing agent. However, without the more rapidly generated disulfide bonds, gels are not formed from $E_{22}$ within an acceptable photocrosslinking time. The combination of disulfide bond formation and the crosslinking of ELP residues resulted in a covalently crosslinked elastic hydrogel.

Physical Characterization of ELP hydrogels.

Figures 2A, 2B, 2C, 2D, 2E, 2F:
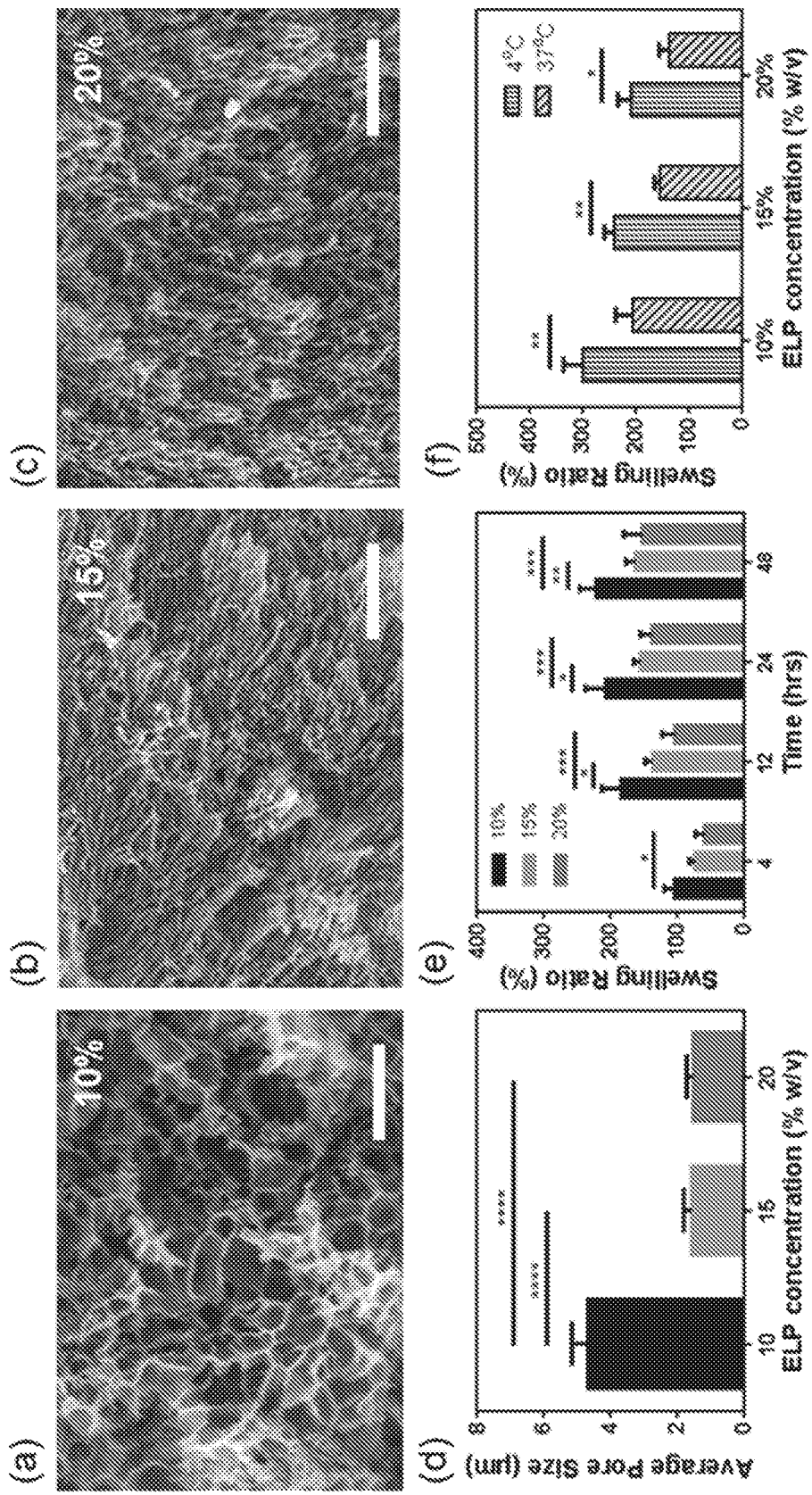
FIGS. 2A-2F show pore characteristics and swelling properties of photocrosslinked ELP hydrogels. Representative SEM images from the cross sections of ELP hydrogels produced by using (FIG. 2A) 10, (FIG. 2B) 15 and (FIG. 2C) 20% (w/v) ELP concentrations (scale bars: 10 μm). The structure of these hydrogels became more compact by increasing ELP concentration.

Photocrosslinked KCTS-$E_{31}$-KCTS (SEQ ID NO: 7) ELPs exhibited tunable physical properties including pore size (FIGS. 2A-2D), swelling ratio (FIGS. 2E, 2F), and mechanical properties (FIGS. 3A-3F) based on ELP prepolymer concentrations. For example, the apparent pore size and swelling ratios of the ELP hydrogels decreased as the ELP concentrations increased (FIGS. 2A-2F). The apparent pore size of the ELP hydrogels decreased from 4.70±0.48 μm to 1.58±0.24 μm and 1.53±0.20 μm as the ELP concentrations increased from 10% to 15% and 20% (w/v), respectively (FIGS. 2A-2D) (p<0.0001 between 10% and 15%, 10% and 20%). As shown in FIG. 2E, increased ELP concentrations decreased hydrogel swelling ratios. After 4 h incubation in PBS at 37° C., the mass swelling ratios were 104.8±15.3, 74.8±8.1, and 60.3±14.7% for ELP concentrations of 10, 15, and 20% (w/v), respectively (p<0.05 between 10% and 20%). In addition, swelling ratios (Okajima T, et al., *The Journal of Chemical Physics* 116, 9068-9077 (2002)) reached equilibrium after 24 h at 207.3±31.5, 155.9±10.1 and 138.3±18.7% for ELP concentrations of 10%, 15% and 20% (w/v), respectively (FIG. 2E). This suggests that constructs containing higher concentrations of thiols are likely able to form more crosslinks, producing a denser microstructure with smaller pore sizes and lower swelling ratios (Lim D W, et al., *Biomacromolecules* 9, 222-230 (2007)). Indeed, the ELP hydrogels had denser apparent microstructures compared to another chemically crosslinked ELP (Debelle L, Tamburro A M., *The International Journal of Biochemistry & Cell Biology* 31, 261-272 (1999)) and a UV crosslinked recombinant human tropoelastin (MeTro) hydrogel that were recently synthesized (Foo CTWP, et al., *Proc Natl Acad Sci* 106, 22067-22072 (2009)). In addition, the resulting ELP hydrogels continued swelling and deswelling in response to temperature fluctuations above and below the LCST (lower critical solution temperature), indicating the preservation of the ELP thermoresponsive nature after photocrosslinking. For example, there was a significant increase (p<0.01) in the swelling ratio, up to 1.5 times larger for 10% ELP hydrogels, when the swollen hydrogels were transferred from 37° C. to 4° C. (FIG. 2F). Maximum percent swelling of ~300% was measured at temperatures below the LCST of the ELP, which is in agreement with other reported ELP hydrogels (Chou C, et al., *Chemical Science* 2, 480-483 (2011)) and in contrast to other standard hydrogels lacking a LCST, which exhibit similar swelling at elevated temperatures (Okajima T, et al., *The Journal of Chemical Physics* 116, 9068-9077 (2002)). The hydrophobicity of the ELP sequence explains its lower swelling ratios in contrast to hydrogels composed of more hydrophilic polymers (Bertassoni L E, et al., *Lab on a Chip* 14, 2202-2211 (2014)).

Figures 3A, 3B, 3C, 3D, 3E, 3F, 3G:
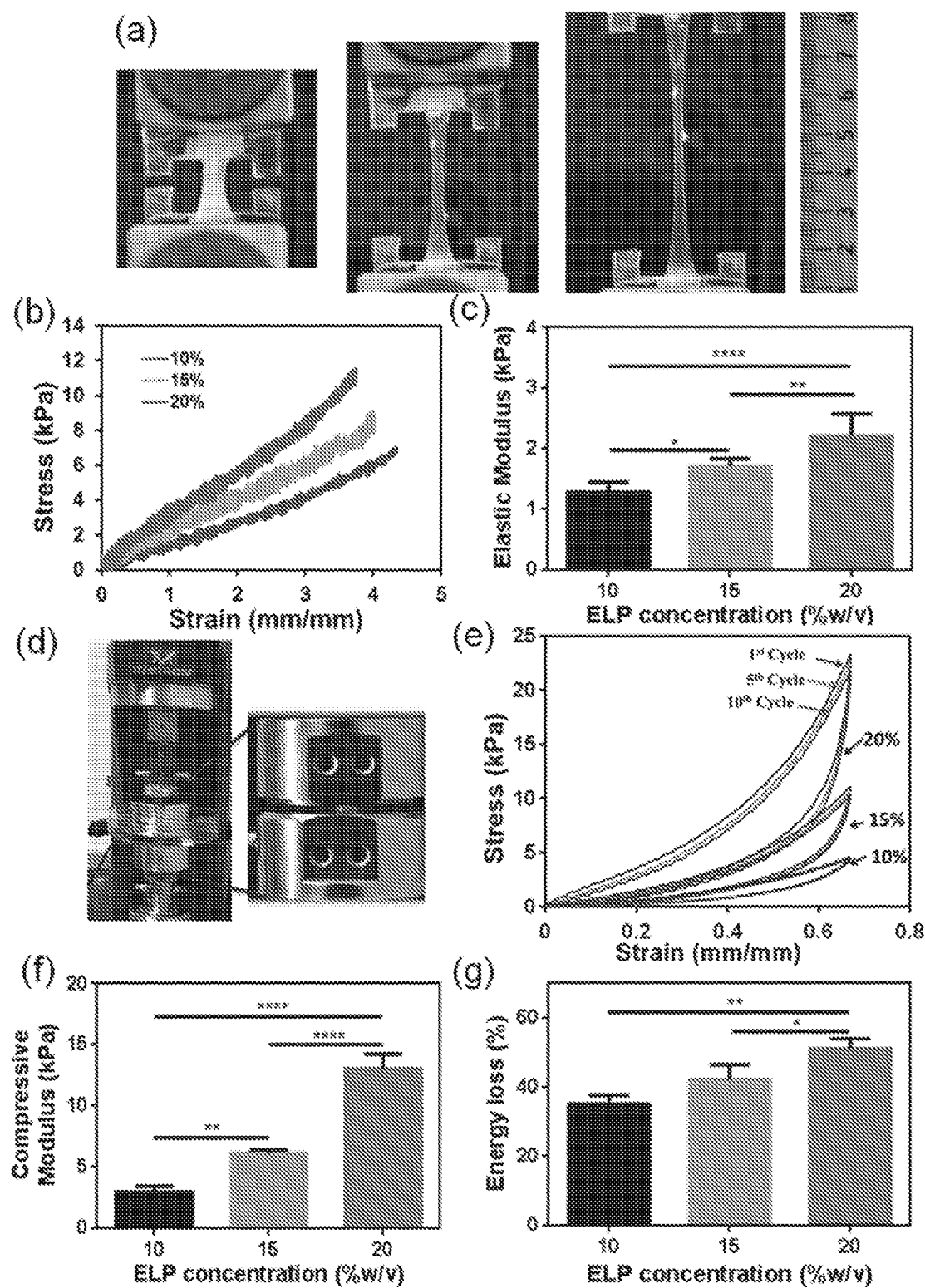
FIGS. 3A-3G show mechanical properties of ELP hydrogels.
Figures 4A, 4B, 4C, 4D:
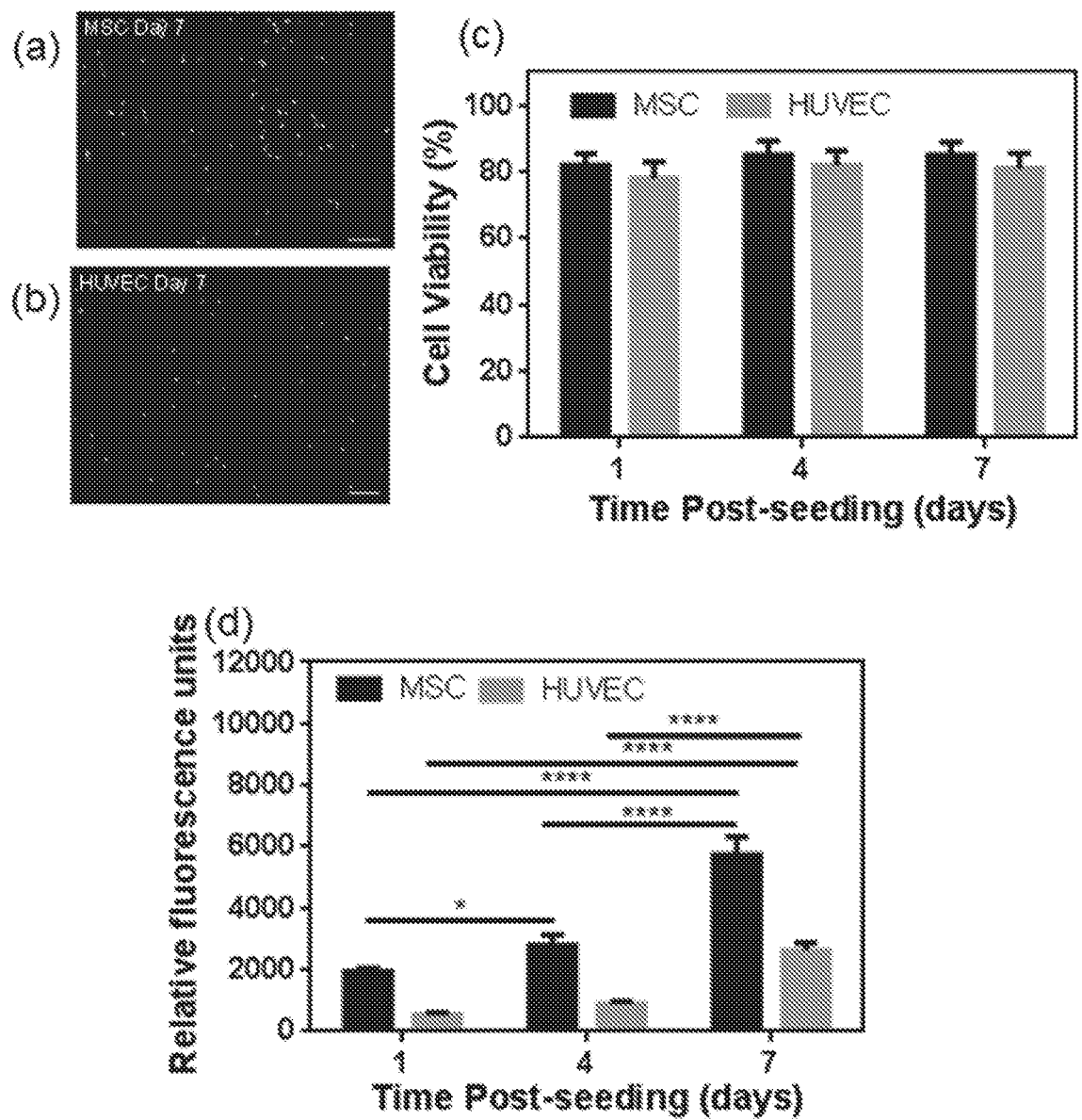
FIGS. 4A-4D show in vitro cell seeding on ELP hydrogels.

The mechanical properties of ELP hydrogels, including elastic modulus, maximum strain, stress at failure, and energy loss, based on tensile and compression tests are shown in FIGS. 3A-3G and also summarized in Table 1. All the engineered ELP hydrogels were highly elastic as confirmed by performing tensile testing (FIG. 3A). The fabricated hydrogels showed elastic modulus of 1.28±0.17 kPa, 1.72±0.11 kPa, and 2.21±0.36 kPa (p<0.05 between 10% and 15%, p<0.01 between 15% and 20%, and p<0.0001 between 10% and 20%) and ultimate tensile strengths of 6.46±0.35 kPa, 7.71±0.53 kPa, and 10.09±1.81 kPa for ELP gels produced by using 10%, 15%, and 20% (w/v) ELP prepolymer solutions (FIGS. 3B-3C, Table 1). In addition, the ELP hydrogels that were formed by using lower protein concentration (10% w/v) were capable of achieving larger ultimate strain (extensibility) at fracture compared to higher concentration gels (FIG. 3B). Lower ELP concentration decreases the number of crosslinks in the system, increasing the molecular weight between crosslinks, Mc, in the network. The larger molecular weight between crosslinks allows for large extensibility as the relaxed ELP coil is extended into an entropically unfavorable stretched state (Charati M B, et al., *Soft Matter* 5, 3412-3416 (2009)). After removal of the applied strain, the recoil is thermodynamically favorable and explains the high extensibility and low hysteresis observed in the system. The extensibilities of resulting ELP gels were much higher than previously fabricated ELP-collagen hydrogels (up to 80%) and other types of elastic polypeptides (ranging from 80-180%) (He D, et al., *PLoS ONE* 7, 1-12 (2012); Sun J-Y, et al., *Nature* 489, 133-136 (2012)), extending the applications of these materials into flexible and stretchable substrates for various biomedical applications (tissue engineering of elastic tissues, injectable elastic materials etc.) (Rogers J A, et al., *Science* 327, 1603-1607 (2010); Annabi N, et al., *Adv Mater* 26, 85-124 (2014)). This highlights the ability of thiols to improve extensibility through chain extension (Odian G. Principles Of Polymerization, Fourth edn (2004)). As a source of comparison, extensibility of a native pulmonary artery varies from 158±25% to 282±48% depending on the direction of tensile loading; thus photocrosslinked ELP hydrogels developed here are capable of withstanding extensions in excess of those achieved in arterial tissue (Foo CTWP, et al., *Proc Natl Acad Sci* 106, 22067-22072 (2009); Baranoski S., *Nursing* 38, 60-61 (2008)).

umbilical vein endothelial cells (HUVEC) as model cells, which confirms their biocompatibility. Cells were cultured on the surface of 10% photocrosslinked ELP hydrogels for 7 days (FIGS. 4A-4B). Cellular viability and metabolic activity were assessed for both MSCs and HUVECs. Cell viability was higher than 80% on ELP hydrogels 1, 4 and 7 days after cell seeding (FIG. 4C), suggesting that the engineered ELP gel had no toxicity on either MSCs or HUVECs. In addition, the metabolic activities of the cells were quantified by PrestoBlue™ as shown in FIG. 4D. The capacity of the ELP hydrogel to support cellular proliferation was supported by the significant increase in fluorescence intensity between days 1 and 7 ($p<0.0001$). Cell spreading was limited for both cell types, which can be due to the lack of cell recognition sites such as arginine-glycine-aspartic acid peptides (RGD) in the ELP sequence that can promote cell adhesion and spreading (Raphel J, et al., *J Mater Chem* 22, 19429-19437 (2012); Costa R R, et al., *Adv Funct Mater* 19, 3210-3218 (2009); Hrabchak C, et al., *Acta Biomater* 6, 2108-2115 (2010)). For tissue engineering applications of these ELP hydrogels, bioactive peptide modifications can be easily incorporated, as explained in previous studies (Baranoski S., *Nursing* 38, 60-61 (2008); Galler K M, et al., *J Am*

TABLE 1

Mechanical characterization of photocrosslinked ELP hydrogels.

| ELP concentration (% w/v) | Elastic modulus (kPa) | Stress at break (kPa) | Strain at break (%) | Compressive modulus (kPa) | Energy loss (%) |
|---|---|---|---|---|---|
| 10 | 1.28 ± 0.17 | 6.46 ± 0.35 | 419 ± 25 | 3.01 ± 0.44 | 35.13 ± 2.55 |
| 15 | 1.72 ± 0.11 | 7.71 ± 0.53 | 395 ± 10 | 6.15 ± 0.28 | 42.10 ± 4.37 |
| 20 | 2.21 ± 0.36 | 10.09 ± 1.81 | 388 ± 12 | 13.05 ± 1.20 | 51.15 ± 2.90 |

Cyclic compression of the ELPs showed complete recoverability of the gel after multiple cycles of compression (FIGS. 3D-3G). As shown in FIG. 3E, all the formulations of ELP hydrogels deformed reversibly following 10 cycles of loading and unloading, with compression strain up to ~70%. The compressive moduli were 3.01±0.44 kPa, 6.15±0.28 kPa and 13.05±1.2 kPa when the ELP concentration was increased from 10%, 15%, to 20% (w/v) (FIG. 3F, Table 1) ($p<0.01$ between 10% and 15%, $p<0.0001$ between 15% and 20%, 10% and 20%). These values are similar to chemically crosslinked ELP[KV7F-72] hydrogels developed by Lim et al. (4-11 kPa) (Debelle L, Tamburro A M., The International *Journal of Biochemistry & Cell Biology* 31, 261-272 (1999)). Energy loss based on cycle 8 was also found to be 35.13±2.55%, 42.10±4.37% and 51.15±2.90% for hydrogels with 10%, 15%, and 20% (w/v) of ELP (FIG. 3G. Table 1) ($p<0.01$ between 10% and 20%, $p<0.05$ between 15% and 20%). Previous studies showed that other hydrogels such as hybrid alginate/polyacrylamide gels exhibited high hysteresis and permanent deformation after cyclic loading with some weakening after the second cycle of compression (Omidian H, et al., *Macromol Biosci* 6, 703-710 (2006)). Despite high energy dissipation during loading/unloading (FIG. 3G), the minimal fatigue observed in photocrosslinked ELP hydrogels after compressive loading confirmed that the elastic nature of ELP gels is preserved through repeated deformations, necessary for implants such as those for cartilage or intervertebral discs (Nettles D L, et al., *Adv Drug Delivery Rev* 62, 1479-1485 (2010)).

In Vitro Biocompatibility of ELP Hydrogels.

Photocrosslinked ELP gels permitted the growth and proliferation of mesenchymal stem cells (MSCs) and human

*Chem Soc* 132, 3217-3223 (2010)), to improve cell viability (Urry D W, et al., *Journal of Bioactive and Compatible Polymers* 6, 263-282 (1991)).

In Vivo Biocompatibility of ELP Hydrogels.

Figures 5A, 5B, 5C, 5D:
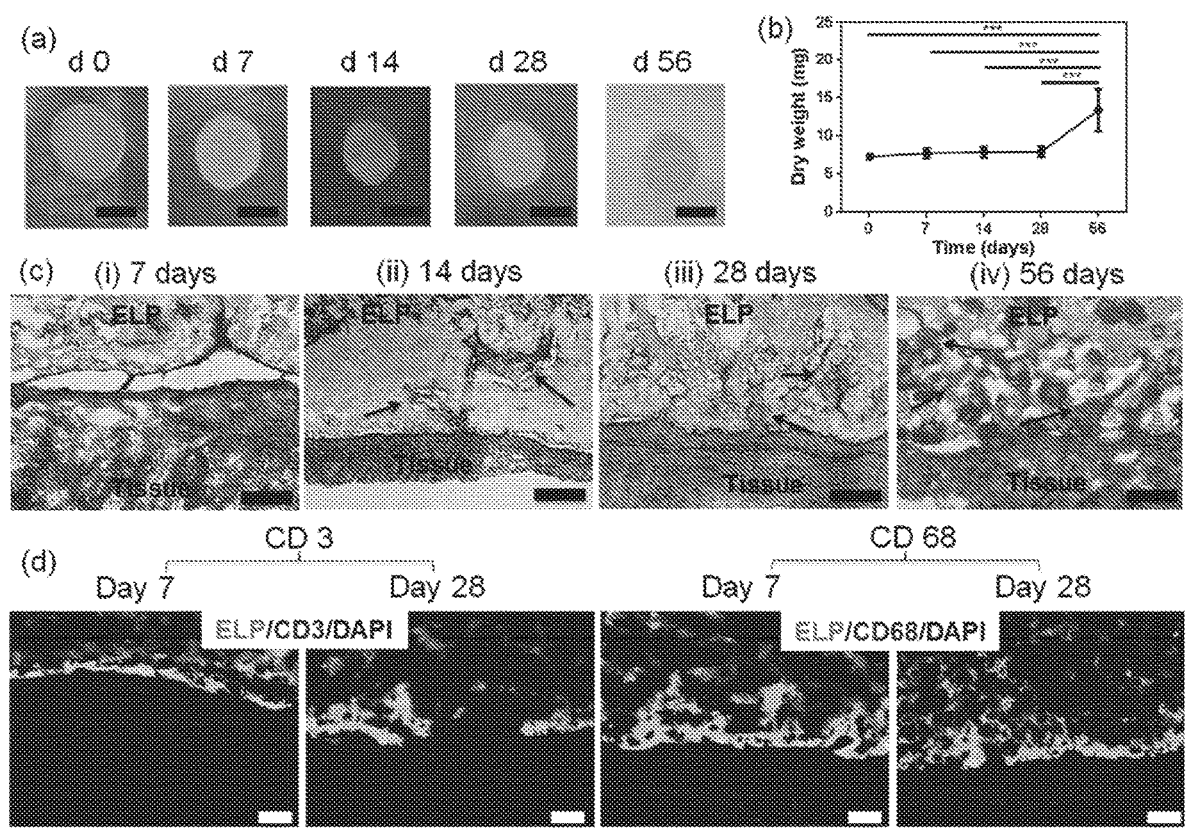
FIGS. 5A-5D show evaluation of degradation and biocompatibility of ELP hydrogels in vivo. ELP hydrogels were implanted into the dorsal subcutaneous space of rats.

ELP gels were subcutaneously implanted in rats to assess gel stability and local interaction of the implant with the animal tissue as well as the immune response of the host. Harvesting of ELP samples at days 7, 14, 28 and 56 revealed maintenance of the macroscopic shapes of the implants during the entire study period, suggesting no relevant degradation of the gels (FIG. 5A). The dry weight of the explanted samples was maintained constant during the first 4 weeks, while the weight was significantly ($p<0.001$) increased at 8 weeks (FIG. 5B). Constant weight is explained by a lack of degradation, whereas an increase in weight after 8 weeks was due to tissue growth onto the ELP construct. Indeed, hematoxylin and eosin staining of subcutaneous ELP implants showed early and progressive growth of predominantly non-inflammatory tissue from the recipient on the samples, implying biocompatibility and integration of the ELP hydrogels in vivo (FIG. 5C).

Thorough evaluation of the histology, samples did not reveal a relevant amount of mononuclear inflammatory cells, which would have been typical of strong local immune response by the host (FIG. 5C). Corroborating this observation, immunohistological staining against surface markers of inflammatory cells proved that there was no lymphocyte infiltration (CD3) in the samples or in the surrounding subcutaneous tissue. Additionally, mild macrophage invasion (CD68) into the interface zone between the sample and the host tissue was observed at day 7, but it completely disappeared by day 28 (FIG. 5D). These data together confirm the biocompatibility of the engineered ELP hydrogels as scaffolds for tissue engineering applications.

In Vitro and In Vivo Hemostatic Potential.

Figures 6A, 6B, 6C, 6D, 6E:
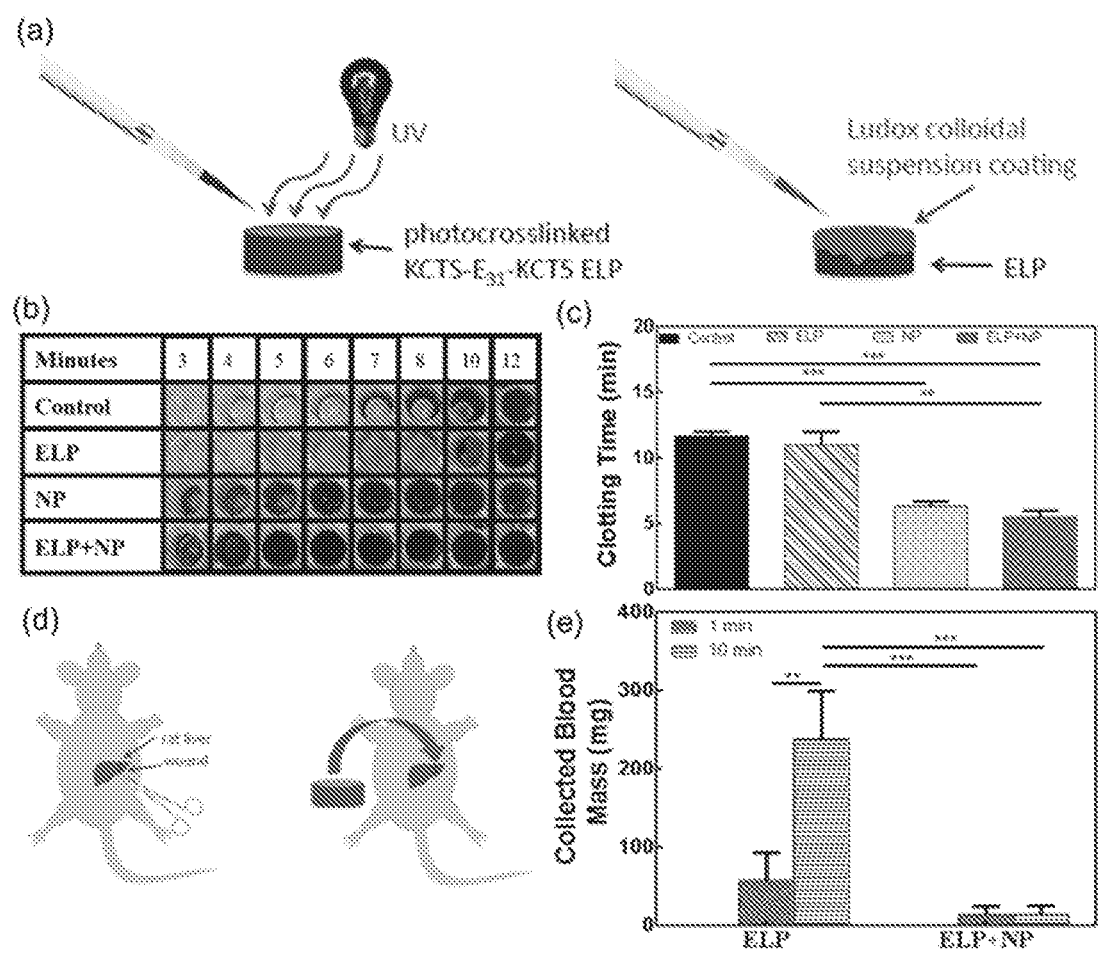
FIGS. 6A-6E show application of ELP hydrogels combined with silica nanoparticle as hemostats.

Given the stability and biocompatibility of the engineered ELPs, an investigation of their potential as an elastic hemostatic material was performed. Hemostatic materials are used in surgical, emergency, and combat situations to manage uncontrolled bleeding by multiple mechanisms (Gaharwar A K, et al., ACS Nano 8, 9833-9842 (2014)). Release of clotting factors, absorption of fluid, and sealing are all hemostatic mechanisms (Spotnitz W D, World journal of surgery 34, 632-634 (2010)). An advantage of absorbent, sealing, or adhesive hemostatic materials is their independence from the clotting cascade, which can be compromised in some patients. The physical barrier formed by the hemostatic materials can staunch blood loss while the body progresses through hemostasis (Spotnitz W D, ISRN Surgery 2014, 28 (2014); van Der Ham A C, et al., British Journal of Surgery 78, 49-53 (1991); Meddahi-Pellé A, et al., Angew Chem Int Ed 53, 6369-6373 (2014)). The use of colloidal solutions of silica nanoparticles as hemostatic agents and tissue adhesives has been recently demonstrated (Rose S, et al., Nature 505, 382-385 (2014); Behrens A M, et al., Acta Biomater 10, 701-708 (2014)). These solutions function to bind tissues together, in a process termed nanobridging, forming effective hemostatic seals in the presence of blood. Nanobridging occurs when nanoparticles in solution form connections that can adhere tissues together (Rose S, et al., Nature 505, 382-385 (2014)). However, as colloidal solutions, delivery to a wound would be suboptimum due to their ability to flow away from the injury site. Using a flexible substrate to deliver a coating of colloidal particles will 1) provide control over the concentration of colloidal solution delivered to a wound based on surface area, 2), maintain intimate contact between the colloidal particles and the wound site, and 3) provide an elastic substrate responsive to mechanical deformations of the wounded tissue. Here, the ELPs were combined with the colloidal solutions of nanoparticles and their hemostatic potential was tested (FIG. 6A).

The absorption of silica nanoparticles as a colloidal solution on the surface of photocrosslinked ELP resulted in decreased clotting times in vitro and in vivo. A schematic of silica nanoparticle (NP; Ludox® TM-50) solutions combined with the photocrosslinked ELP hydrogel is shown in FIG. 6A. To form ELP/NP hemostatic hydrogels, a drop of 50 wt % NP solution was absorbed on photocrosslinked ELP gels. The ability of engineered NP modified photocrosslinked ELP to promote clotting was then investigated in vitro. A clotting time assay was performed in which wells of a 96-well plate were used to monitor the progression of clot formation. After set times, washing wells containing combinations of activated blood, photocrosslinked ELP, and NPs with a saline solution caused only clotted blood to remain in the well (FIG. 6B). Volumes as small as 2 µL of NP in 100 µL blood were able to decrease clotting times compared to controls. Maximum decrease in clotting time was observed with 10 µL NP solution per 100 µL blood, with a 46% drop in clotting time compared to controls, comparable to commercial hemostats (Spotnitz W D, World journal of surgery 34, 632-634 (2010)). Photocrosslinked ELP with 10 µL NP pipetted onto the ELP surface prior to addition of blood was able to decrease clotting times by 53% compared to controls (FIG. 6C). The extended clotting time for the control sample compared to other observed whole blood clotting times (Spotnitz W D, World journal of surgery 34, 632-634 (2010)) is likely due to variability between donors. However, using this time as an internal control, the improvements in clotting time with ELP and NP treatments suggest a synergistic effect on clotting when both are used.

When applied in vivo, photocrosslinked ELP samples modified with NP solution promoted hemostasis in standardized liver wounds with acute hemorrhage that was otherwise lethal, as demonstrated in a recent study (Spotnitz W D, World journal of surgery 34, 632-634 (2010)). A schematic of liver wound creation and treatment with NP-coated ELP is shown in FIG. 6D. When NPs were coated on the surface of photocrosslinked ELP, improvements in clotting time and blood loss were greater than when photocrosslinked ELP was applied to the wound alone. Placement of the photocrosslinked ELP samples on liver wounds resulted in occlusive clotting within 10 min, while NP-modified ELP decreased the bleeding time to below 2 min. When ELP and NP were combined in treatment, blood mass loss was 76% and 94% lower after 1 and 10 min, respectively compared to treatment with ELP alone (FIG. 6E). Similar decreases in blood loss and hemostasis time have been observed with acrylamide-based particles in liver bleeding models (Coin I, et al., Peptides for Youth 611, 127-128 (2009)). Additionally, further blood loss was still observed after 10 min when only ELP was applied to liver bleeding while blood loss was only observed for an average of 1.5 min when NP was coated on the ELP surface. Removal of the hydrogel from the wound did not cause re-bleeding, indicating sufficient sealing of the wound. Improvement in clotting time upon the addition of nanoparticles highlights the ability to modify the photocrosslinked ELPs for treatment of hemorrhage. The ability of the nanoparticles to promote hemostasis when coated on photocrosslinked ELP creates a hemostat with improved extensibility and stability in vivo. Such systems can be utilized for vascular or soft tissue injuries which require a combination of clotting ability, elasticity, and flexibility to adjust to wounds with complex geometry or moving tissue (Gaharwar A K, et al., ACS Nano 8, 9833-9842 (2014); Spotnitz W D, ISRN Surgery 2014, 28 (2014)).

Discussion

Elastic hydrogels can serve as scaffolds for various biomedical applications. Combinations of physical and chemical crosslinks in this system produced recoverable (from physical bonds) and tough (from chemical bonds) gels, which can be used for tissue engineering applications. Other synthetic polymers like poly(glycerol-sebacate) (PGS) can form biodegradable scaffolds that combine hydrogen bonding between hydroxyl groups and covalent bonding to generate elastic biomaterials that are also biocompatible (Wang Y et al., Nat Biotech 20, 602-606 (2002)). Nanocomposite hydrogels can also achieve high elasticity with additional functionality, such as electrical conductivity (Li Y, Shimizu H., Macromolecules 42, 2587-2593 (2009)). These systems can be used to form biomaterials with high moduli and strain recovery but may require harsh processing conditions (e.g. high temperature) or the use of toxic solvents, which may limit their biological applications. Though some are biocompatible, most of the synthetic polymer-based elastic scaffolds lack bioactive sequences to promote cell adhesion or migration, which is important for their tissue engineering applications.

Bioactive sequences can be incorporated into synthetic elastomers to improve their biological properties (Zhu J, Marchant R E, Expert review of medical devices 8, 607-626 (2011)) but an even more direct approach is to utilize protein-based polymer to develop elastic scaffolds. Elastic hydrogels have been developed from ELPs using block copolymer designs that contain hydrophilic and hydrophobic domains, and crosslinkable blocks to generate chemically crosslinked gels (Debelle L, Tamburro A M, The International *Journal of Biochemistry & Cell Biology* 31, 261-272 (1999)). Other recombinant approaches have incorporated lysines within elastin-like blocks followed by conjugation of diazirine groups to facilitate photoreactive crosslinking of ELPs. However, these systems require the additional conjugation of the photoreactive group to ELP sequence and 1-2 h of UV exposure for the photocrosslinking of ELPs (Raphel J, et al., *J Mater Chem* 22, 19429-19437 (2012)). Non-canonical amino acids can also be incorporated into peptides by synthetic methods using solid phase synthesis but are limited to low molecular weight peptides (Chin J W, et al., *Proc Natl Acad Sci USA* 99, 11020-11024 (2002)). Genetic engineering has been also applied to design novel tRNA and incorporate photoreactive benzophenones (Carrico I S, et al., *J Am Chem Soc* 129, 4874-4875 (2007)) and para-azidophenylalanine (Lim D W, et al., *Biomacromolecules* 8, 1463-1470 (2007)) into ELPs expressed by *E. coli*. All these techniques require modified genetic machinery. In addition, providing non-canonical amino acids can in some instances complicate production of peptides for biomedical applications.

Here, recombinantly expressed ELP hydrogels have been developed that were shown to photocrosslink without additional modifications to the as-expressed protein sequence. The gels were extensible up to 420% strain and fatigue resistant in compression. The inclusion of thiol groups on expressed ELPs allowed for rapid photocrosslinking (Nettles D L, et al., *Tissue engineering Part A* 14, 1133-1140 (2008); Betre H, et al., *Biomaterials* 27, 91-99 (2006)) of hydrogels that maintained the elasticity and biocompatibility inherent in ELPs. The large extensibility (420% strain at fracture) of these KCTS-E$_{31}$-KCTS (SEQ ID NO: 7) ELPs is important for the engineering of elastic tissues (Foo CTWP, et al., *Proc Natl Acad Sci* 106, 22067-22072 (2009); Baranoski S., *Nursing* 38, 60-61 (2008)). The recombinant design of these KCTS-E$_{31}$-KCTS (SEQ ID NO: 7) gels allow for exceptional control over the presentation of bioactive peptide sequences, which can be used to improve cell viability, proliferation or promote specific cellular interactions in vitro or in vivo (Raphel J, et al., *J Mater Chem* 22, 19429-19437 (2012); Hrabchak C, et al., *Acta Biomater* 6, 2108-2115 (2010); Lee K Y, Mooney D J., *Chem Rev* 101, 1869-1880 (2001)).

In vivo examination revealed excellent biocompatibility and minimal degradation resulting in early and progressive growth of host tissue. Slowly degrading systems can provide a matrix within which tissue growth can be supported (Annabi N, et al., *Biomaterials* 30, 1-7 (2009)). The possibility for conjugation of bioactive sequences into recombinant proteins provides that such a photocrosslinkable ELP could be tailored for a wide range of tissue applications, including cartilage regeneration (Nettles D L, et al., *Tissue engineering Part A* 14, 1133-1140 (2008); McHale M K, et al., *Tissue Eng* 11, 1768-1779 (2005)), and vascular and ocular applications (Nettles D L, et al., *Adv Drug Delivery Rev* 62, 1479-1485 (2010)), among others. Since crosslinking can be localized, the ELP can likewise function as tissue fillers, conforming to the shape of defects and subsequently being crosslinked to stabilize the hydrogel. Furthermore, hemostatic functionalization with Ludox® TM-50 nanoparticles allowed for effective treatment of lethally bleeding liver wounds. The photocrosslinked ELP provided a platform onto which hemostatic materials could be added to localize their activity in an environment that would otherwise wash them away, as well as synergistically improved the hemostatic potential of the system. Compared to fibrin-based hemostats (Gaharwar A K, et al., *ACS Nano* 8, 9833-9842 (2014)), such ELP-based flexible hemostatic materials can be designed to control bleeding as well as promote wound healing on tissues and organs without confining natural tissue movement. Injectable ELP solutions containing hemostatic particles can be photocrosslinked at the site of bleeding, functioning as an effective hemostat material and a matrix for tissue regeneration. With these qualities, photocrosslinkable ELPs can be used in biomedical applications as a hemostatic material for soft and flexible tissues such as blood vessels, skin, lung, or cardiac tissue.

Polynucleotide and amino acid sequences for one embodiment of an ELP as described herein are set out below.

The complete nucleotide sequence of a completed ELP gene is as follows, with the cysteine containing sequence (KCTS) (SEQ ID NO: 6) italicized and the ELP gene sequence in normal type:

(SEQ ID NO: 27)
GGATCC*AAATGTACCAGC*GCTAGCGGTCTCGTTGGTGTACCTGGTGTTG

GCGTCCCGGGTGTAGGTATCCCAGGCGTTGGTGTACCGGGTGTAGGCGT

TCCAGGCGTTGGTGTACCTGGTGTTGGCGTCCCGGGTGTAGGTATCCCA

GGCGTTGGTGTACCGGGTGTAGGCGTTCCAGGCGTTGGTGTACCTGGTG

TTGGCGTCCCGGGTGTAGGTATCCCAGGCGTTGGTGTACCGGGTGTAGG

CGTTCCAGGCGTTGGTGTACCTGGTGTTGGCGTCCCGGGTGTAGGTATC

CCAGGCGTTGGTGTACCGGGTGTAGGCGTTCCAGGCGTTGGTGTACCTG

GTGTTGGCGTCCCGGGTGTAGGTATCCCAGGCGTTGGTGTACCGGGTGT

AGGCGTTCCAGGCGTTGGTGTACCTGGTGTTGGCGTCCCGGGTGTAGGT

ATCCCAGGCGTTGGTGTACCGGGTGTAGGCGTTCCAGGCGTTGGTGTAC

CTGGTGTTGGCGTCCCGGGTGTAGGTATCCCAGGCGTTGGTGTACCGGG

TGTAGGCGTTCCAGGCGTTGGTGTACCTGGTGTTGGCGTCCCGGGTGTA

GGTATCCCAGGCGTTGGTGTACCGGGTGTAGGCGTTCCAGGCGTTGGTG

TACCTGGTGTTGGCGTCCCGGGTGTAGGTATCCCAGGCGTTGGTGTACC

GGGTGTAGGCGTTCCAGGCGTTGGTGTACCTGGTGTTGGCGTCCCGGGT

GTAGGTATCCCAGGCGTTGGTGTACCGGGTGTAGGCGTTCCAGGCGTTG

GTGTACCTGGTGTTGGCGTCCCGGGTGTAGGTATCCCAGGCGTTGGTGT

ACCGGGTGTAGGCGTTCCAGGCGTTGGTGTACCTGGTGTTGGCGTCCCG

GGTGTAGGTATCCCAGGCGTTGGTGTACCGGGTGTAGGCGTTCCAGGCG

TTGGTGTACCTGGTGTTGGCGTCCCGGGTGTAGGTATCCCAGGCGTTGG

TGTACCGGGTGTAGGCGTTCCAGGCGTTGGTGTACCTGGTGTTGGCGTC

CCGGGTGTAGGTATCCCAGGCGTTGGTGTACCGGGTGTAGGCGTTCCAG

GCGTTGGTGAGACCACTAGTTAAATGAAT*AAATGCACGTCT*TAAAAGCT

T

The amino acid sequence of one embodiment of an ELP polypeptide as described herein is as follows:

(SEQ ID NO: 26)
MGWGSKCTSASGLVGVPGVGVPGVGIPGVGVPGVGVPGVGVPGVGVPGV
GIPGVGVPGVGVPGVGVPGVGVPGVGIPGVGVPGVGVPGVGVPGVGVPG
VGIPGVGVPGVGVPGVGVPGVGVPGVGIPGVGVPGVGVPGVGVPGVGVP

-continued

GVGIPGVGVPGVGVPGVGVPGVGVPGVGVPGVGIPGVGVPGVGVPGVGV
PGVGIPGVGVPGVGVPGVGVPGVGVPGVGVPGVGIPGVGVPGVGVPGVG
VPGVGIPGVGVPGVGVPGVGVPGVGVPGVGVPGVGIPGVGVPGVGVPGV
GVPGVGIPGVGVPGVGVPGVGVPGVGVPGVGIPGVGVPGVGVPGVGVPG
VGVPGVGIPGVGVPGVGVPGVGETTSKCTS*.

---

What is claimed is:

1. A composition comprising:
   a) a polypeptide comprising the amino acid sequence of $\{[VPGVG]_4IPGVG\}_n$, wherein n is an integer greater than 1 (SEQ ID NO: 2), and wherein the polypeptide comprises a first cysteine-containing peptide linked to a first side of the amino acid sequence of $\{[VPGVG]_4IPGVG\}_n$ (SEQ ID NO: 2); and
   b) 2-hydroxy-1-(4-(hydroxyethoxy) phenyl)-2-methyl-1-propanone.

2. The composition of claim 1, wherein n is in the range of 10-28.

3. The composition of claim 1, further comprising a second cysteine-containing peptide linked to a second side of the amino acid sequence of $\{[VPGVG]_4IPGVG\}_n$ (SEQ ID NO: 2).

4. The composition of claim 3, wherein the first cysteine-containing peptide or the second cysteine-containing peptide comprises an amino acid sequence of KCTS (SEQ ID NO: 6).

5. The composition of claim 1, further comprising an amino acid sequence of RGD.

6. A hydrogel comprising a photo-crosslinked composition of claim 1.

7. The hydrogel of claim 6, wherein the polypeptide is present at a concentration between 5% and 30% (w/v).

8. The hydrogel of claim 6, having extensibility up to 500%.

9. The hydrogel of claim 6, having an elastic modulus in the range of 0.5-10 kPa.

10. The hydrogel of claim 6, having a tensile strength in the range of 4 to 20 kPa.

11. The hydrogel of claim 6, having a compressive modulus of 1 to 20 kPa.

12. The hydrogel of claim 6, further comprising a hemostatic agent selected from the group consisting of silica nanoparticles, blood coagulation factors, prothrombin, thrombin, fibrinogen, fibrin, gelatin, collagen, polysaccharide, and cellulose.

13. The hydrogel of claim 6, further comprising an antibacterial agent selected from the group consisting of silver nanoparticles, copper oxide nanoparticles, nanoparticle-carried antibiotic drugs, penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, and sulfamethoxazole.

14. The hydrogel of claim 6, further comprising one or more biological cells.

15. The hydrogel of claim 6, produced by crosslinking the polypeptide in the presence of the photoinitiator under light irradiation.

16. A tissue scaffold comprising a hydrogel of claim 6 and at least one biological cell.

17. A method of treating bleeding or soft-tissue injury, the method comprising contacting a site of bleeding or soft-tissue injury with a hydrogel of claim 6 and a hemostatic agent.

* * * * *

UNITED STATES PATENT AND TRADEMARK OFFICE
CERTIFICATE OF CORRECTION

| | |
|---|---|
| PATENT NO. | : 10,723,783 B2 |
| APPLICATION NO. | : 15/559481 |
| DATED | : July 28, 2020 |
| INVENTOR(S) | : Annabi et al. |

It is certified that error appears in the above-identified patent and that said Letters Patent is hereby corrected as shown below:

In the Specification

At Column 1, Line 17:
Insert the following heading and paragraph:
-- GOVERNMENT SUPPORT
This invention was made with government support under AR063745 awarded by the National Institutes of Health. The government has certain rights in the invention. --

Signed and Sealed this
Second Day of May, 2023

Katherine Kelly Vidal
Director of the United States Patent and Trademark Office

SEQUENCE LISTING

<160> NUMBER OF SEQ ID NOS: 27

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid except Pro

<400> SEQUENCE: 1

Val Pro Gly Xaa Gly
1               5

<210> SEQ ID NO 2
<211> LENGTH: 1250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1250)
<223> OTHER INFORMATION: This sequence may encompass 2-50 "(VPGVG)4-
      IPGVG" repeating units, wherein some positions may be absent
<220> FEATURE:
<223> OTHER INFORMATION: See specification as filed for detailed
      description of substitutions and preferred embodiments

<400> SEQUENCE: 2

Val Pro Gly Val Gly Val Pro Gly Val Gly Val Pro Gly Val Gly Val
1               5                   10                  15

Pro Gly Val Gly Ile Pro Gly Val Gly Val Pro Gly Val Gly Val Pro
            20                  25                  30

Gly Val Gly Val Pro Gly Val Gly Val Pro Gly Val Gly Ile Pro Gly
        35                  40                  45

Val Gly Val Pro Gly Val Gly Val Pro Gly Val Gly Val Pro Gly Val
    50                  55                  60

Gly Val Pro Gly Val Gly Ile Pro Gly Val Gly Val Pro Gly Val Gly
65                  70                  75                  80

Val Pro Gly Val Gly Val Pro Gly Val Gly Val Pro Gly Val Gly Ile
                85                  90                  95

Pro Gly Val Gly Val Pro Gly Val Gly Val Pro Gly Val Gly Val Pro
            100                 105                 110

Gly Val Gly Val Pro Gly Val Gly Ile Pro Gly Val Gly Val Pro Gly
        115                 120                 125

Val Gly Val Pro Gly Val Gly Val Pro Gly Val Gly Val Pro Gly Val
    130                 135                 140

-continued

```
Gly Ile Pro Gly Val Gly Val Pro Gly Val Gly Val Pro Gly Val Gly
145                 150                 155                 160

Val Pro Gly Val Gly Val Pro Gly Val Gly Ile Pro Gly Val Gly Val
                165                 170                 175

Pro Gly Val Gly Val Pro Gly Val Gly Val Pro Gly Val Gly Val Pro
            180                 185                 190

Gly Val Gly Ile Pro Gly Val Gly Val Pro Gly Val Gly Val Pro Gly
        195                 200                 205

Val Gly Val Pro Gly Val Gly Val Pro Gly Val Gly Ile Pro Gly Val
    210                 215                 220

Gly Val Pro Gly Val Gly Val Pro Gly Val Gly Val Pro Gly Val Gly
225                 230                 235                 240

Val Pro Gly Val Gly Ile Pro Gly Val Gly Val Pro Gly Val Gly Val
                245                 250                 255

Pro Gly Val Gly Val Pro Gly Val Gly Val Pro Gly Val Gly Ile Pro
            260                 265                 270

Gly Val Gly Val Pro Gly Val Gly Val Pro Gly Val Gly Val Pro Gly
        275                 280                 285

Val Gly Val Pro Gly Val Gly Ile Pro Gly Val Gly Val Pro Gly Val
    290                 295                 300

Gly Val Pro Gly Val Gly Val Pro Gly Val Gly Val Pro Gly Val Gly
305                 310                 315                 320

Ile Pro Gly Val Gly Val Pro Gly Val Gly Val Pro Gly Val Gly Val
                325                 330                 335

Pro Gly Val Gly Val Pro Gly Val Gly Ile Pro Gly Val Gly Val Pro
            340                 345                 350

Gly Val Gly Val Pro Gly Val Gly Val Pro Gly Val Gly Val Pro Gly
        355                 360                 365

Val Gly Ile Pro Gly Val Gly Val Pro Gly Val Gly Val Pro Gly Val
    370                 375                 380

Gly Val Pro Gly Val Gly Val Pro Gly Val Gly Ile Pro Gly Val Gly
385                 390                 395                 400

Val Pro Gly Val Gly Val Pro Gly Val Gly Val Pro Gly Val Gly Val
                405                 410                 415

Pro Gly Val Gly Ile Pro Gly Val Gly Val Pro Gly Val Gly Val Pro
            420                 425                 430

Gly Val Gly Val Pro Gly Val Gly Val Pro Gly Val Gly Ile Pro Gly
        435                 440                 445

Val Gly Val Pro Gly Val Gly Val Pro Gly Val Gly Val Pro Gly Val
    450                 455                 460

Gly Val Pro Gly Val Gly Ile Pro Gly Val Gly Val Pro Gly Val Gly
465                 470                 475                 480

Val Pro Gly Val Gly Val Pro Gly Val Gly Val Pro Gly Val Gly Ile
                485                 490                 495

Pro Gly Val Gly Val Pro Gly Val Gly Val Pro Gly Val Gly Val Pro
            500                 505                 510

Gly Val Gly Val Pro Gly Val Gly Ile Pro Gly Val Gly Val Pro Gly
        515                 520                 525

Val Gly Val Pro Gly Val Gly Val Pro Gly Val Gly Val Pro Gly Val
    530                 535                 540

Gly Ile Pro Gly Val Gly Val Pro Gly Val Gly Val Pro Gly Val Gly
545                 550                 555                 560
```

Val Pro Gly Val Gly Val Pro Gly Val Gly Ile Pro Gly Val Gly Val
            565                 570                 575

Pro Gly Val Gly Val Pro Gly Val Gly Val Pro Gly Val Gly Val Pro
        580                 585                 590

Gly Val Gly Ile Pro Gly Val Gly Val Pro Gly Val Gly Val Pro Gly
    595                 600                 605

Val Gly Val Pro Gly Val Gly Val Pro Gly Val Gly Ile Pro Gly Val
        610                 615                 620

Gly Val Pro Gly Val Gly Val Pro Gly Val Gly Val Pro Gly Val Gly
625                 630                 635                 640

Val Pro Gly Val Gly Ile Pro Gly Val Gly Val Pro Gly Val Gly Val
            645                 650                 655

Pro Gly Val Gly Val Pro Gly Val Gly Val Pro Gly Val Gly Ile Pro
        660                 665                 670

Gly Val Gly Val Pro Gly Val Gly Val Pro Gly Val Gly Val Pro Gly
    675                 680                 685

Val Gly Val Pro Gly Val Gly Ile Pro Gly Val Gly Val Pro Gly Val
        690                 695                 700

Gly Val Pro Gly Val Gly Val Pro Gly Val Gly Val Pro Gly Val Gly
705                 710                 715                 720

Ile Pro Gly Val Gly Val Pro Gly Val Gly Val Pro Gly Val Gly Val
            725                 730                 735

Pro Gly Val Gly Val Pro Gly Val Gly Ile Pro Gly Val Gly Val Pro
        740                 745                 750

Gly Val Gly Val Pro Gly Val Gly Val Pro Gly Val Gly Val Pro Gly
    755                 760                 765

Val Gly Ile Pro Gly Val Gly Val Pro Gly Val Gly Val Pro Gly Val
        770                 775                 780

Gly Val Pro Gly Val Gly Val Pro Gly Val Gly Ile Pro Gly Val Gly
785                 790                 795                 800

Val Pro Gly Val Gly Val Pro Gly Val Gly Val Pro Gly Val Gly Val
            805                 810                 815

Pro Gly Val Gly Ile Pro Gly Val Gly Val Pro Gly Val Gly Val Pro
        820                 825                 830

Gly Val Gly Val Pro Gly Val Gly Val Pro Gly Val Gly Ile Pro Gly
    835                 840                 845

Val Gly Val Pro Gly Val Gly Val Pro Gly Val Gly Val Pro Gly Val
        850                 855                 860

Gly Val Pro Gly Val Gly Ile Pro Gly Val Gly Val Pro Gly Val Gly
865                 870                 875                 880

Val Pro Gly Val Gly Val Pro Gly Val Gly Val Pro Gly Val Gly Ile
            885                 890                 895

Pro Gly Val Gly Val Pro Gly Val Gly Val Pro Gly Val Gly Val Pro
        900                 905                 910

Gly Val Gly Val Pro Gly Val Gly Ile Pro Gly Val Gly Val Pro Gly
    915                 920                 925

Val Gly Val Pro Gly Val Gly Val Pro Gly Val Gly Val Pro Gly Val
        930                 935                 940

Gly Ile Pro Gly Val Gly Val Pro Gly Val Gly Val Pro Gly Val Gly
945                 950                 955                 960

Val Pro Gly Val Gly Val Pro Gly Val Gly Ile Pro Gly Val Gly Val
            965                 970                 975

Pro Gly Val Gly Val Pro Gly Val Gly Val Pro Gly Val Gly Val Pro

-continued

```
                980             985             990
Gly Val Gly Ile Pro Gly Val Gly  Val Pro Gly Val Gly  Val Pro Gly
        995             1000            1005
Val Gly Val Pro Gly Val Gly  Val Pro Gly Val Gly  Ile Pro Gly
        1010            1015            1020
Val Gly Val Pro Gly Val Gly  Val Pro Gly Val Gly  Val Pro Gly
        1025            1030            1035
Val Gly Val Pro Gly Val Gly  Ile Pro Gly Val Gly  Val Pro Gly
        1040            1045            1050
Val Gly Val Pro Gly Val Gly  Val Pro Gly Val Gly  Val Pro Gly
        1055            1060            1065
Val Gly Ile Pro Gly Val Gly  Val Pro Gly Val Gly  Val Pro Gly
        1070            1075            1080
Val Gly Val Pro Gly Val Gly  Val Pro Gly Val Gly  Ile Pro Gly
        1085            1090            1095
Val Gly Val Pro Gly Val Gly  Val Pro Gly Val Gly  Val Pro Gly
        1100            1105            1110
Val Gly Val Pro Gly Val Gly  Ile Pro Gly Val Gly  Val Pro Gly
        1115            1120            1125
Val Gly Val Pro Gly Val Gly  Val Pro Gly Val Gly  Val Pro Gly
        1130            1135            1140
Val Gly Ile Pro Gly Val Gly  Val Pro Gly Val Gly  Val Pro Gly
        1145            1150            1155
Val Gly Val Pro Gly Val Gly  Val Pro Gly Val Gly  Ile Pro Gly
        1160            1165            1170
Val Gly Val Pro Gly Val Gly  Val Pro Gly Val Gly  Val Pro Gly
        1175            1180            1185
Val Gly Val Pro Gly Val Gly  Ile Pro Gly Val Gly  Val Pro Gly
        1190            1195            1200
Val Gly Val Pro Gly Val Gly  Val Pro Gly Val Gly  Val Pro Gly
        1205            1210            1215
Val Gly Ile Pro Gly Val Gly  Val Pro Gly Val Gly  Val Pro Gly
        1220            1225            1230
Val Gly Val Pro Gly Val Gly  Val Pro Gly Val Gly  Ile Pro Gly
        1235            1240            1245
Val Gly
        1250

<210> SEQ ID NO 3
<211> LENGTH: 700
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(700)
<223> OTHER INFORMATION: This sequence may encompass 10-28 "(VPGVG)4-
      IPGVG" repeating units, wherein some positions may be absent
<220> FEATURE:
<223> OTHER INFORMATION: See specification as filed for detailed
      description of substitutions and preferred embodiments

<400> SEQUENCE: 3

Val Pro Gly Val Gly Val Pro Gly Val Gly Val Pro Gly Val Gly Val
1               5                   10                  15

Pro Gly Val Gly Ile Pro Gly Val Gly Val Pro Gly Val Gly Val Pro
```

```
            20                  25                  30
Gly Val Gly Val Pro Gly Val Gly Val Pro Gly Val Gly Ile Pro Gly
        35                  40                  45
Val Gly Val Pro Gly Val Gly Val Pro Gly Val Gly Val Pro Gly Val
        50                  55                  60
Gly Val Pro Gly Val Gly Ile Pro Gly Val Gly Val Pro Gly Val Gly
65                  70                  75                  80
Val Pro Gly Val Gly Val Pro Gly Val Gly Val Pro Gly Val Gly Ile
                85                  90                  95
Pro Gly Val Gly Val Pro Gly Val Gly Val Pro Gly Val Gly Val Pro
                100                 105                 110
Gly Val Gly Val Pro Gly Val Gly Ile Pro Gly Val Gly Val Pro Gly
                115                 120                 125
Val Gly Val Pro Gly Val Gly Val Pro Gly Val Gly Val Pro Gly Val
                130                 135                 140
Gly Ile Pro Gly Val Gly Val Pro Gly Val Gly Val Pro Gly Val Gly
145                 150                 155                 160
Val Pro Gly Val Gly Val Pro Gly Val Gly Ile Pro Gly Val Gly Val
                165                 170                 175
Pro Gly Val Gly Val Pro Gly Val Gly Val Pro Gly Val Gly Val Pro
                180                 185                 190
Gly Val Gly Ile Pro Gly Val Gly Val Pro Gly Val Gly Val Pro Gly
                195                 200                 205
Val Gly Val Pro Gly Val Gly Val Pro Gly Val Gly Ile Pro Gly Val
                210                 215                 220
Gly Val Pro Gly Val Gly Val Pro Gly Val Gly Val Pro Gly Val Gly
225                 230                 235                 240
Val Pro Gly Val Gly Ile Pro Gly Val Gly Val Pro Gly Val Gly Val
                245                 250                 255
Pro Gly Val Gly Val Pro Gly Val Gly Val Pro Gly Val Gly Ile Pro
                260                 265                 270
Gly Val Gly Val Pro Gly Val Gly Val Pro Gly Val Gly Val Pro Gly
                275                 280                 285
Val Gly Val Pro Gly Val Gly Ile Pro Gly Val Gly Val Pro Gly Val
                290                 295                 300
Gly Val Pro Gly Val Gly Val Pro Gly Val Gly Val Pro Gly Val Gly
305                 310                 315                 320
Ile Pro Gly Val Gly Val Pro Gly Val Gly Val Pro Gly Val Gly Val
                325                 330                 335
Pro Gly Val Gly Val Pro Gly Val Gly Ile Pro Gly Val Gly Val Pro
                340                 345                 350
Gly Val Gly Val Pro Gly Val Gly Val Pro Gly Val Gly Val Pro Gly
                355                 360                 365
Val Gly Ile Pro Gly Val Gly Val Pro Gly Val Gly Val Pro Gly Val
                370                 375                 380
Gly Val Pro Gly Val Gly Val Pro Gly Val Gly Ile Pro Gly Val Gly
385                 390                 395                 400
Val Pro Gly Val Gly Val Pro Gly Val Gly Val Pro Gly Val Gly Val
                405                 410                 415
Pro Gly Val Gly Ile Pro Gly Val Gly Val Pro Gly Val Gly Val Pro
                420                 425                 430
Gly Val Gly Val Pro Gly Val Gly Val Pro Gly Val Gly Ile Pro Gly
                435                 440                 445
```

-continued

Val Gly Val Pro Gly Val Gly Val Pro Gly Val Gly Val Pro Gly Val
    450                 455                 460

Gly Val Pro Gly Val Gly Ile Pro Gly Val Gly Val Pro Gly Val Gly
465                 470                 475                 480

Val Pro Gly Val Gly Val Pro Gly Val Gly Val Pro Gly Val Gly Ile
                485                 490                 495

Pro Gly Val Gly Val Pro Gly Val Gly Val Pro Gly Val Gly Val Pro
            500                 505                 510

Gly Val Gly Val Pro Gly Val Gly Ile Pro Gly Val Gly Val Pro Gly
        515                 520                 525

Val Gly Val Pro Gly Val Gly Val Pro Gly Val Gly Val Pro Gly Val
    530                 535                 540

Gly Ile Pro Gly Val Gly Val Pro Gly Val Gly Val Pro Gly Val Gly
545                 550                 555                 560

Val Pro Gly Val Gly Val Pro Gly Val Gly Ile Pro Gly Val Gly Val
                565                 570                 575

Pro Gly Val Gly Val Pro Gly Val Gly Val Pro Gly Val Gly Val Pro
            580                 585                 590

Gly Val Gly Ile Pro Gly Val Gly Val Pro Gly Val Gly Val Pro Gly
        595                 600                 605

Val Gly Val Pro Gly Val Gly Val Pro Gly Val Gly Ile Pro Gly Val
    610                 615                 620

Gly Val Pro Gly Val Gly Val Pro Gly Val Gly Val Pro Gly Val Gly
625                 630                 635                 640

Val Pro Gly Val Gly Ile Pro Gly Val Gly Val Pro Gly Val Gly Val
                645                 650                 655

Pro Gly Val Gly Val Pro Gly Val Gly Val Pro Gly Val Gly Ile Pro
            660                 665                 670

Gly Val Gly Val Pro Gly Val Gly Val Pro Gly Val Gly Val Pro Gly
        675                 680                 685

Val Gly Val Pro Gly Val Gly Ile Pro Gly Val Gly
    690                 695                 700

<210> SEQ ID NO 4
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(350)
<223> OTHER INFORMATION: This sequence may encompass 10-14 "(VPGVG)4-
      IPGVG" repeating units, wherein some positions may be absent
<220> FEATURE:
<223> OTHER INFORMATION: See specification as filed for detailed
      description of substitutions and preferred embodiments

<400> SEQUENCE: 4

Val Pro Gly Val Gly Val Pro Gly Val Gly Val Pro Gly Val Gly Val
1               5                   10                  15

Pro Gly Val Gly Ile Pro Gly Val Gly Val Pro Gly Val Gly Val Pro
            20                  25                  30

Gly Val Gly Val Pro Gly Val Gly Val Pro Gly Val Gly Ile Pro Gly
        35                  40                  45

Val Gly Val Pro Gly Val Gly Val Pro Gly Val Gly Val Pro Gly Val
    50                  55                  60

```
Gly Val Pro Gly Val Gly Ile Pro Gly Val Gly Val Pro Gly Val Gly
65                  70                  75                  80

Val Pro Gly Val Gly Val Pro Gly Val Gly Val Pro Gly Val Gly Ile
                85                  90                  95

Pro Gly Val Gly Val Pro Gly Val Gly Val Pro Gly Val Gly Val Pro
            100                 105                 110

Gly Val Gly Val Pro Gly Val Gly Ile Pro Gly Val Gly Val Pro Gly
        115                 120                 125

Val Gly Val Pro Gly Val Gly Val Pro Gly Val Gly Val Pro Gly Val
    130                 135                 140

Gly Ile Pro Gly Val Gly Val Pro Gly Val Gly Val Pro Gly Val Gly
145                 150                 155                 160

Val Pro Gly Val Gly Val Pro Gly Val Gly Ile Pro Gly Val Gly Val
                165                 170                 175

Pro Gly Val Gly Val Pro Gly Val Gly Val Pro Gly Val Gly Val Pro
            180                 185                 190

Gly Val Gly Ile Pro Gly Val Gly Val Pro Gly Val Gly Val Pro Gly
        195                 200                 205

Val Gly Val Pro Gly Val Gly Val Pro Gly Val Gly Ile Pro Gly Val
    210                 215                 220

Gly Val Pro Gly Val Gly Val Pro Gly Val Gly Val Pro Gly Val Gly
225                 230                 235                 240

Val Pro Gly Val Gly Ile Pro Gly Val Gly Val Pro Gly Val Gly Val
                245                 250                 255

Pro Gly Val Gly Val Pro Gly Val Gly Val Pro Gly Val Gly Ile Pro
            260                 265                 270

Gly Val Gly Val Pro Gly Val Gly Val Pro Gly Val Gly Val Pro Gly
        275                 280                 285

Val Gly Val Pro Gly Val Gly Ile Pro Gly Val Gly Val Pro Gly Val
    290                 295                 300

Gly Val Pro Gly Val Gly Val Pro Gly Val Gly Val Pro Gly Val Gly
305                 310                 315                 320

Ile Pro Gly Val Gly Val Pro Gly Val Gly Val Pro Gly Val Gly Val
                325                 330                 335

Pro Gly Val Gly Val Pro Gly Val Gly Ile Pro Gly Val Gly
            340                 345                 350

<210> SEQ ID NO 5
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Val Pro Gly Val Gly Val Pro Gly Val Gly Val Pro Gly Val Gly Val
1               5                   10                  15

Pro Gly Val Gly Ile Pro Gly Val Gly Val Pro Gly Val Gly Val Pro
            20                  25                  30

Gly Val Gly Val Pro Gly Val Gly Val Pro Gly Val Gly Ile Pro Gly
        35                  40                  45

Val Gly Val Pro Gly Val Gly Val Pro Gly Val Gly Val Pro Gly Val
    50                  55                  60

Gly Val Pro Gly Val Gly Ile Pro Gly Val Gly Val Pro Gly Val Gly
```

```
                 65                  70                  75                  80
Val Pro Gly Val Gly Val Pro Gly Val Gly Val Pro Gly Val Gly Ile
                 85                  90                  95
Pro Gly Val Gly Val Pro Gly Val Gly Val Pro Gly Val Gly Val Pro
                100                 105                 110
Gly Val Gly Val Pro Gly Val Gly Ile Pro Gly Val Gly Val Pro Gly
                115                 120                 125
Val Gly Val Pro Gly Val Gly Val Pro Gly Val Gly Val Pro Gly Val
                130                 135                 140
Gly Ile Pro Gly Val Gly Val Pro Gly Val Gly Val Pro Gly Val Gly
145                 150                 155                 160
Val Pro Gly Val Gly Val Pro Gly Val Gly Ile Pro Gly Val Gly Val
                165                 170                 175
Pro Gly Val Gly Val Pro Gly Val Gly Val Pro Gly Val Gly Val Pro
                180                 185                 190
Gly Val Gly Ile Pro Gly Val Gly Val Pro Gly Val Gly Val Pro Gly
                195                 200                 205
Val Gly Val Pro Gly Val Gly Val Pro Gly Val Gly Ile Pro Gly Val
                210                 215                 220
Gly Val Pro Gly Val Gly Val Pro Gly Val Gly Val Pro Gly Val Gly
225                 230                 235                 240
Val Pro Gly Val Gly Ile Pro Gly Val Gly Val Pro Gly Val Gly Val
                245                 250                 255
Pro Gly Val Gly Val Pro Gly Val Gly Val Pro Gly Val Gly Ile Pro
                260                 265                 270
Gly Val Gly Val Pro Gly Val Gly Val Pro Gly Val Gly Val Pro Gly
                275                 280                 285
Val Gly Val Pro Gly Val Gly Ile Pro Gly Val Gly Val Pro Gly Val
                290                 295                 300
Gly Val Pro Gly Val Gly Val Pro Gly Val Gly Val Pro Gly Val Gly
305                 310                 315                 320
Ile Pro Gly Val Gly Val Pro Gly Val Gly Val Pro Gly Val Gly Val
                325                 330                 335
Pro Gly Val Gly Val Pro Gly Val Gly Ile Pro Gly Val Gly
                340                 345                 350

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Cys Thr Ser
1

<210> SEQ ID NO 7
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Lys Cys Thr Ser Val Pro Gly Val Gly Val Pro Gly Val Gly Val Pro
```

```
1               5                   10                  15
Gly Val Gly Val Pro Gly Val Gly Ile Pro Gly Val Gly Val Pro Gly
            20                  25                  30
Val Gly Val Pro Gly Val Gly Val Pro Gly Val Gly Val Pro Gly Val
            35                  40                  45
Gly Ile Pro Gly Val Gly Val Pro Gly Val Gly Val Pro Gly Val Gly
            50                  55                  60
Val Pro Gly Val Gly Val Pro Gly Val Gly Ile Pro Gly Val Gly Val
65                  70                  75                  80
Pro Gly Val Gly Val Pro Gly Val Gly Val Pro Gly Val Gly Val Pro
            85                  90                  95
Gly Val Gly Ile Pro Gly Val Gly Val Pro Gly Val Gly Val Pro Gly
            100                 105                 110
Val Gly Val Pro Gly Val Gly Val Pro Gly Val Gly Ile Pro Gly Val
            115                 120                 125
Gly Val Pro Gly Val Gly Val Pro Gly Val Gly Val Pro Gly Val Gly
            130                 135                 140
Val Pro Gly Val Gly Ile Pro Gly Val Gly Val Pro Gly Val Gly Val
145                 150                 155                 160
Pro Gly Val Gly Val Pro Gly Val Gly Val Pro Gly Val Gly Ile Pro
            165                 170                 175
Gly Val Gly Val Pro Gly Val Gly Val Pro Gly Val Gly Val Pro Gly
            180                 185                 190
Val Gly Val Pro Gly Val Gly Ile Pro Gly Val Gly Val Pro Gly Val
            195                 200                 205
Gly Val Pro Gly Val Gly Val Pro Gly Val Gly Val Pro Gly Val Gly
            210                 215                 220
Ile Pro Gly Val Gly Val Pro Gly Val Gly Val Pro Gly Val Gly Val
225                 230                 235                 240
Pro Gly Val Gly Val Pro Gly Val Gly Ile Pro Gly Val Gly Val Pro
            245                 250                 255
Gly Val Gly Val Pro Gly Val Gly Val Pro Gly Val Gly Val Pro Gly
            260                 265                 270
Val Gly Ile Pro Gly Val Gly Val Pro Gly Val Gly Val Pro Gly Val
            275                 280                 285
Gly Val Pro Gly Val Gly Val Pro Gly Val Gly Ile Pro Gly Val Gly
            290                 295                 300
Val Pro Gly Val Gly Val Pro Gly Val Gly Val Pro Gly Val Gly Val
305                 310                 315                 320
Pro Gly Val Gly Ile Pro Gly Val Gly Val Pro Gly Val Gly Val Pro
            325                 330                 335
Gly Val Gly Val Pro Gly Val Gly Val Pro Gly Val Gly Ile Pro Gly
            340                 345                 350
Val Gly Lys Cys Thr Ser
            355

<210> SEQ ID NO 8
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
```

```
<223> OTHER INFORMATION: This region may encompass 1-10 "VPGVG"
     repeating units, wherein some positions may be absent
<220> FEATURE:
<223> OTHER INFORMATION: See specification as filed for detailed
     description of substitutions and preferred embodiments

<400> SEQUENCE: 8

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Ile Pro Gly Val Gly
    50                  55

<210> SEQ ID NO 9
<211> LENGTH: 2750
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MISC_FEATURE
<222> LOCATION: (1)..(50)
<223> OTHER INFORMATION: This region may encompass 1-10 "VPGVG"
     repeating units, wherein some positions may be absent
<220> FEATURE:
<221> NAME/KEY: MISC_FEATURE
<222> LOCATION: (56)..(105)
<223> OTHER INFORMATION: This region may encompass 1-10 "VPGVG"
     repeating units, wherein some positions may be absent
<220> FEATURE:
<221> NAME/KEY: MISC_FEATURE
<222> LOCATION: (111)..(160)
<223> OTHER INFORMATION: This region may encompass 1-10 "VPGVG"
     repeating units, wherein some positions may be absent
<220> FEATURE:
<221> NAME/KEY: MISC_FEATURE
<222> LOCATION: (166)..(215)
<223> OTHER INFORMATION: This region may encompass 1-10 "VPGVG"
     repeating units, wherein some positions may be absent
<220> FEATURE:
<221> NAME/KEY: MISC_FEATURE
<222> LOCATION: (221)..(270)
<223> OTHER INFORMATION: This region may encompass 1-10 "VPGVG"
     repeating units, wherein some positions may be absent
<220> FEATURE:
<221> NAME/KEY: MISC_FEATURE
<222> LOCATION: (276)..(325)
<223> OTHER INFORMATION: This region may encompass 1-10 "VPGVG"
     repeating units, wherein some positions may be absent
<220> FEATURE:
<221> NAME/KEY: MISC_FEATURE
<222> LOCATION: (331)..(380)
<223> OTHER INFORMATION: This region may encompass 1-10 "VPGVG"
     repeating units, wherein some positions may be absent
<220> FEATURE:
<221> NAME/KEY: MISC_FEATURE
<222> LOCATION: (386)..(435)
<223> OTHER INFORMATION: This region may encompass 1-10 "VPGVG"
     repeating units, wherein some positions may be absent
<220> FEATURE:
<221> NAME/KEY: MISC_FEATURE
<222> LOCATION: (441)..(490)
<223> OTHER INFORMATION: This region may encompass 1-10 "VPGVG"
     repeating units, wherein some positions may be absent
<220> FEATURE:
<221> NAME/KEY: MISC_FEATURE
<222> LOCATION: (496)..(545)
<223> OTHER INFORMATION: This region may encompass 1-10 "VPGVG"
     repeating units, wherein some positions may be absent
<220> FEATURE:
```

```
<221> NAME/KEY: MISC_FEATURE
<222> LOCATION: (551)..(600)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (606)..(655)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (661)..(710)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (716)..(765)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (771)..(820)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (826)..(875)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (881)..(930)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (936)..(985)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (991)..(1040)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1046)..(1095)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1101)..(1150)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1156)..(1205)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1211)..(1260)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1266)..(1315)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1321)..(1370)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1376)..(1425)
<223> OTHER INFORMATION: This region may encompass 1-10 "VPGVG"
      repeating units, wherein some positions may be absent
```

```
<220> FEATURE:
<221> NAME/KEY: MISC_FEATURE
<222> LOCATION: (1431)..(1480)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1486)..(1535)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1541)..(1590)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1596)..(1645)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1651)..(1700)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1706)..(1755)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1761)..(1810)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1816)..(1865)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1871)..(1920)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1926)..(1975)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1981)..(2030)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (2036)..(2085)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (2091)..(2140)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (2146)..(2195)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (2201)..(2250)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (2256)..(2305)
<223> OTHER INFORMATION: This region may encompass 1-10 "VPGVG"
```

```
      repeating units, wherein some positions may be absent
<220> FEATURE:
<221> NAME/KEY: MISC_FEATURE
<222> LOCATION: (2311)..(2360)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (2366)..(2415)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (2421)..(2470)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (2476)..(2525)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (2531)..(2580)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (2586)..(2635)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (2641)..(2690)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (2696)..(2745)
<223> OTHER INFORMATION: This region may encompass 1-10 "VPGVG"
      repeating units, wherein some positions may be absent
<220> FEATURE:
<221> NAME/KEY: MISC_FEATURE
<222> LOCATION: (1)..(2750)
<223> OTHER INFORMATION: This sequence may encompass 2-50 "(VPGVG)m-
      IPGVG" repeating units, wherein m is 1-10 and some positions may
      be absent
<220> FEATURE:
<223> OTHER INFORMATION: See specification as filed for detailed
      description of substitutions and preferred embodiments

<400> SEQUENCE: 9

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Ile Pro Gly Val Gly Val Pro Gly Val Gly Val Pro Gly Val
    50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
                85                  90                  95

Pro Gly Val Gly Val Pro Gly Val Gly Ile Pro Gly Val Gly Val Pro
            100                 105                 110

Gly Val Gly Val Pro Gly Val Gly Val Pro Gly Val Gly Val Pro Gly
        115                 120                 125

Val Gly Val Pro Gly Val Gly Val Pro Gly Val Gly Val Pro Gly Val
    130                 135                 140
```

```
Gly Val Pro Gly Val Gly Val Pro Gly Val Gly Val Pro Gly Val Gly
145                 150                 155                 160
Ile Pro Gly Val Gly Val Pro Gly Val Gly Val Pro Gly Val Gly Val
                165                 170                 175
Pro Gly Val Gly Val Pro Gly Val Gly Val Pro Gly Val Gly Val Pro
            180                 185                 190
Gly Val Gly Val Pro Gly Val Gly Val Pro Gly Val Gly Val Pro Gly
        195                 200                 205
Val Gly Val Pro Gly Val Gly Ile Pro Gly Val Gly Val Pro Gly Val
    210                 215                 220
Gly Val Pro Gly Val Gly Val Pro Gly Val Gly Val Pro Gly Val Gly
225                 230                 235                 240
Val Pro Gly Val Gly Val Pro Gly Val Gly Val Pro Gly Val Gly Val
                245                 250                 255
Pro Gly Val Gly Val Pro Gly Val Gly Val Pro Gly Val Gly Ile Pro
            260                 265                 270
Gly Val Gly Val Pro Gly Val Gly Val Pro Gly Val Gly Val Pro Gly
        275                 280                 285
Val Gly Val Pro Gly Val Gly Val Pro Gly Val Gly Val Pro Gly Val
    290                 295                 300
Gly Val Pro Gly Val Gly Val Pro Gly Val Gly Val Pro Gly Val Gly
305                 310                 315                 320
Val Pro Gly Val Gly Ile Pro Gly Val Gly Val Pro Gly Val Gly Val
                325                 330                 335
Pro Gly Val Gly Val Pro Gly Val Gly Val Pro Gly Val Gly Val Pro
            340                 345                 350
Gly Val Gly Val Pro Gly Val Gly Val Pro Gly Val Gly Val Pro Gly
        355                 360                 365
Val Gly Val Pro Gly Val Gly Val Pro Gly Val Gly Ile Pro Gly Val
    370                 375                 380
Gly Val Pro Gly Val Gly Val Pro Gly Val Gly Val Pro Gly Val Gly
385                 390                 395                 400
Val Pro Gly Val Gly Val Pro Gly Val Gly Val Pro Gly Val Gly Val
                405                 410                 415
Pro Gly Val Gly Val Pro Gly Val Gly Val Pro Gly Val Gly Val Pro
            420                 425                 430
Gly Val Gly Ile Pro Gly Val Gly Val Pro Gly Val Gly Val Pro Gly
        435                 440                 445
Val Gly Val Pro Gly Val Gly Val Pro Gly Val Gly Val Pro Gly Val
    450                 455                 460
Gly Val Pro Gly Val Gly Val Pro Gly Val Gly Val Pro Gly Val Gly
465                 470                 475                 480
Val Pro Gly Val Gly Val Pro Gly Val Gly Ile Pro Gly Val Gly Val
                485                 490                 495
Pro Gly Val Gly Val Pro Gly Val Gly Val Pro Gly Val Gly Val Pro
            500                 505                 510
Gly Val Gly Val Pro Gly Val Gly Val Pro Gly Val Gly Val Pro Gly
        515                 520                 525
Val Gly Val Pro Gly Val Gly Val Pro Gly Val Gly Val Pro Gly Val
    530                 535                 540
Gly Ile Pro Gly Val Gly Val Pro Gly Val Gly Val Pro Gly Val Gly
545                 550                 555                 560
```

Val Pro Gly Val Gly Val Pro Gly Val Gly Val Pro Gly Val
        565                 570                 575

Pro Gly Val Gly Val Pro Gly Val Gly Val Pro Gly Val Gly Val Pro
        580                 585                 590

Gly Val Gly Val Pro Gly Val Gly Ile Pro Gly Val Gly Val Pro Gly
        595                 600                 605

Val Gly Val Pro Gly Val Gly Val Pro Gly Val Gly Val Pro Gly Val
        610                 615                 620

Gly Val Pro Gly Val Gly Val Pro Gly Val Gly Val Pro Gly Val Gly
625                 630                 635                 640

Val Pro Gly Val Gly Val Pro Gly Val Gly Val Pro Gly Val Gly Ile
                645                 650                 655

Pro Gly Val Gly Val Pro Gly Val Gly Val Pro Gly Val Gly Val Pro
        660                 665                 670

Gly Val Gly Val Pro Gly Val Gly Val Pro Gly Val Gly Val Pro Gly
        675                 680                 685

Val Gly Val Pro Gly Val Gly Val Pro Gly Val Gly Val Pro Gly Val
        690                 695                 700

Gly Val Pro Gly Val Gly Ile Pro Gly Val Gly Val Pro Gly Val Gly
705                 710                 715                 720

Val Pro Gly Val Gly Val Pro Gly Val Gly Val Pro Gly Val Gly Val
                725                 730                 735

Pro Gly Val Gly Val Pro Gly Val Gly Val Pro Gly Val Gly Val Pro
        740                 745                 750

Gly Val Gly Val Pro Gly Val Gly Val Pro Gly Val Gly Ile Pro Gly
        755                 760                 765

Val Gly Val Pro Gly Val Gly Val Pro Gly Val Gly Val Pro Gly Val
        770                 775                 780

Gly Val Pro Gly Val Gly Val Pro Gly Val Gly Val Pro Gly Val Gly
785                 790                 795                 800

Val Pro Gly Val Gly Val Pro Gly Val Gly Val Pro Gly Val Gly Val
                805                 810                 815

Pro Gly Val Gly Ile Pro Gly Val Gly Val Pro Gly Val Gly Val Pro
        820                 825                 830

Gly Val Gly Val Pro Gly Val Gly Val Pro Gly Val Gly Val Pro Gly
        835                 840                 845

Val Gly Val Pro Gly Val Gly Val Pro Gly Val Gly Val Pro Gly Val
        850                 855                 860

Gly Val Pro Gly Val Gly Val Pro Gly Val Gly Ile Pro Gly Val Gly
865                 870                 875                 880

Val Pro Gly Val Gly Val Pro Gly Val Gly Val Pro Gly Val Gly Val
                885                 890                 895

Pro Gly Val Gly Val Pro Gly Val Gly Val Pro Gly Val Gly Val Pro
        900                 905                 910

Gly Val Gly Val Pro Gly Val Gly Val Pro Gly Val Gly Val Pro Gly
        915                 920                 925

Val Gly Ile Pro Gly Val Gly Val Pro Gly Val Gly Val Pro Gly Val
        930                 935                 940

Gly Val Pro Gly Val Gly Val Pro Gly Val Gly Val Pro Gly Val Gly
945                 950                 955                 960

Val Pro Gly Val Gly Val Pro Gly Val Gly Val Pro Gly Val Gly Val
                965                 970                 975

Pro Gly Val Gly Val Pro Gly Val Gly Ile Pro Gly Val Gly Val Pro

-continued

```
                980             985             990
Gly Val Gly Val Pro Gly Val Gly  Val Pro Gly Val Gly  Val Pro Gly
        995             1000            1005
Val Gly  Val Pro Gly Val Gly  Val Pro Gly Val Gly  Val Pro Gly
    1010            1015            1020

Val Gly  Val Pro Gly Val Gly  Val Pro Gly Val Gly  Val Pro Gly
    1025            1030            1035

Val Gly  Ile Pro Gly Val Gly  Val Pro Gly Val Gly  Val Pro Gly
    1040            1045            1050

Val Gly  Val Pro Gly Val Gly  Val Pro Gly Val Gly  Val Pro Gly
    1055            1060            1065

Val Gly  Val Pro Gly Val Gly  Val Pro Gly Val Gly  Val Pro Gly
    1070            1075            1080

Val Gly  Val Pro Gly Val Gly  Val Pro Gly Val Gly  Ile Pro Gly
    1085            1090            1095

Val Gly  Val Pro Gly Val Gly  Val Pro Gly Val Gly  Val Pro Gly
    1100            1105            1110

Val Gly  Val Pro Gly Val Gly  Val Pro Gly Val Gly  Val Pro Gly
    1115            1120            1125

Val Gly  Val Pro Gly Val Gly  Val Pro Gly Val Gly  Val Pro Gly
    1130            1135            1140

Val Gly  Val Pro Gly Val Gly  Ile Pro Gly Val Gly  Val Pro Gly
    1145            1150            1155

Val Gly  Val Pro Gly Val Gly  Val Pro Gly Val Gly  Val Pro Gly
    1160            1165            1170

Val Gly  Val Pro Gly Val Gly  Val Pro Gly Val Gly  Val Pro Gly
    1175            1180            1185

Val Gly  Val Pro Gly Val Gly  Val Pro Gly Val Gly  Val Pro Gly
    1190            1195            1200

Val Gly  Ile Pro Gly Val Gly  Val Pro Gly Val Gly  Val Pro Gly
    1205            1210            1215

Val Gly  Val Pro Gly Val Gly  Val Pro Gly Val Gly  Val Pro Gly
    1220            1225            1230

Val Gly  Val Pro Gly Val Gly  Val Pro Gly Val Gly  Val Pro Gly
    1235            1240            1245

Val Gly  Val Pro Gly Val Gly  Val Pro Gly Val Gly  Ile Pro Gly
    1250            1255            1260

Val Gly  Val Pro Gly Val Gly  Val Pro Gly Val Gly  Val Pro Gly
    1265            1270            1275

Val Gly  Val Pro Gly Val Gly  Val Pro Gly Val Gly  Val Pro Gly
    1280            1285            1290

Val Gly  Val Pro Gly Val Gly  Val Pro Gly Val Gly  Val Pro Gly
    1295            1300            1305

Val Gly  Val Pro Gly Val Gly  Ile Pro Gly Val Gly  Val Pro Gly
    1310            1315            1320

Val Gly  Val Pro Gly Val Gly  Val Pro Gly Val Gly  Val Pro Gly
    1325            1330            1335

Val Gly  Val Pro Gly Val Gly  Val Pro Gly Val Gly  Val Pro Gly
    1340            1345            1350

Val Gly  Val Pro Gly Val Gly  Val Pro Gly Val Gly  Val Pro Gly
    1355            1360            1365

Val Gly  Ile Pro Gly Val Gly  Val Pro Gly Val Gly  Val Pro Gly
    1370            1375            1380
```

-continued

Val Gly Val Pro Gly Val Gly Val Pro Gly Val Gly Val Pro Gly
    1385                1390                1395

Val Gly Val Pro Gly Val Gly Val Pro Gly Val Gly Val Pro Gly
    1400                1405                1410

Val Gly Val Pro Gly Val Gly Val Pro Gly Val Gly Ile Pro Gly
    1415                1420                1425

Val Gly Val Pro Gly Val Gly Val Pro Gly Val Gly Val Pro Gly
    1430                1435                1440

Val Gly Val Pro Gly Val Gly Val Pro Gly Val Gly Val Pro Gly
    1445                1450                1455

Val Gly Val Pro Gly Val Gly Val Pro Gly Val Gly Val Pro Gly
    1460                1465                1470

Val Gly Val Pro Gly Val Gly Ile Pro Gly Val Gly Val Pro Gly
    1475                1480                1485

Val Gly Val Pro Gly Val Gly Val Pro Gly Val Gly Val Pro Gly
    1490                1495                1500

Val Gly Val Pro Gly Val Gly Val Pro Gly Val Gly Val Pro Gly
    1505                1510                1515

Val Gly Val Pro Gly Val Gly Val Pro Gly Val Gly Val Pro Gly
    1520                1525                1530

Val Gly Ile Pro Gly Val Gly Val Pro Gly Val Gly Val Pro Gly
    1535                1540                1545

Val Gly Val Pro Gly Val Gly Val Pro Gly Val Gly Val Pro Gly
    1550                1555                1560

Val Gly Val Pro Gly Val Gly Val Pro Gly Val Gly Val Pro Gly
    1565                1570                1575

Val Gly Val Pro Gly Val Gly Val Pro Gly Val Gly Ile Pro Gly
    1580                1585                1590

Val Gly Val Pro Gly Val Gly Val Pro Gly Val Gly Val Pro Gly
    1595                1600                1605

Val Gly Val Pro Gly Val Gly Val Pro Gly Val Gly Val Pro Gly
    1610                1615                1620

Val Gly Val Pro Gly Val Gly Val Pro Gly Val Gly Val Pro Gly
    1625                1630                1635

Val Gly Val Pro Gly Val Gly Ile Pro Gly Val Gly Val Pro Gly
    1640                1645                1650

Val Gly Val Pro Gly Val Gly Val Pro Gly Val Gly Val Pro Gly
    1655                1660                1665

Val Gly Val Pro Gly Val Gly Val Pro Gly Val Gly Val Pro Gly
    1670                1675                1680

Val Gly Val Pro Gly Val Gly Val Pro Gly Val Gly Val Pro Gly
    1685                1690                1695

Val Gly Ile Pro Gly Val Gly Val Pro Gly Val Gly Val Pro Gly
    1700                1705                1710

Val Gly Val Pro Gly Val Gly Val Pro Gly Val Gly Val Pro Gly
    1715                1720                1725

Val Gly Val Pro Gly Val Gly Val Pro Gly Val Gly Val Pro Gly
    1730                1735                1740

Val Gly Val Pro Gly Val Gly Val Pro Gly Val Gly Ile Pro Gly
    1745                1750                1755

Val Gly Val Pro Gly Val Gly Val Pro Gly Val Gly Val Pro Gly
    1760                1765                1770

Val Gly Val Pro Gly Val Gly Val Pro Gly Val Gly Val Pro Gly
1775              1780              1785

Val Gly Val Pro Gly Val Gly Val Pro Gly Val Gly Val Pro Gly
1790              1795              1800

Val Gly Val Pro Gly Val Gly Ile Pro Gly Val Gly Val Pro Gly
1805              1810              1815

Val Gly Val Pro Gly Val Gly Val Pro Gly Val Gly Val Pro Gly
1820              1825              1830

Val Gly Val Pro Gly Val Gly Val Pro Gly Val Gly Val Pro Gly
1835              1840              1845

Val Gly Val Pro Gly Val Gly Val Pro Gly Val Gly Val Pro Gly
1850              1855              1860

Val Gly Ile Pro Gly Val Gly Val Pro Gly Val Gly Val Pro Gly
1865              1870              1875

Val Gly Val Pro Gly Val Gly Val Pro Gly Val Gly Val Pro Gly
1880              1885              1890

Val Gly Val Pro Gly Val Gly Val Pro Gly Val Gly Val Pro Gly
1895              1900              1905

Val Gly Val Pro Gly Val Gly Val Pro Gly Val Gly Ile Pro Gly
1910              1915              1920

Val Gly Val Pro Gly Val Gly Val Pro Gly Val Gly Val Pro Gly
1925              1930              1935

Val Gly Val Pro Gly Val Gly Val Pro Gly Val Gly Val Pro Gly
1940              1945              1950

Val Gly Val Pro Gly Val Gly Val Pro Gly Val Gly Val Pro Gly
1955              1960              1965

Val Gly Val Pro Gly Val Gly Ile Pro Gly Val Gly Val Pro Gly
1970              1975              1980

Val Gly Val Pro Gly Val Gly Val Pro Gly Val Gly Val Pro Gly
1985              1990              1995

Val Gly Val Pro Gly Val Gly Val Pro Gly Val Gly Val Pro Gly
2000              2005              2010

Val Gly Val Pro Gly Val Gly Val Pro Gly Val Gly Val Pro Gly
2015              2020              2025

Val Gly Ile Pro Gly Val Gly Val Pro Gly Val Gly Val Pro Gly
2030              2035              2040

Val Gly Val Pro Gly Val Gly Val Pro Gly Val Gly Val Pro Gly
2045              2050              2055

Val Gly Val Pro Gly Val Gly Val Pro Gly Val Gly Val Pro Gly
2060              2065              2070

Val Gly Val Pro Gly Val Gly Val Pro Gly Val Gly Ile Pro Gly
2075              2080              2085

Val Gly Val Pro Gly Val Gly Val Pro Gly Val Gly Val Pro Gly
2090              2095              2100

Val Gly Val Pro Gly Val Gly Val Pro Gly Val Gly Val Pro Gly
2105              2110              2115

Val Gly Val Pro Gly Val Gly Val Pro Gly Val Gly Val Pro Gly
2120              2125              2130

Val Gly Val Pro Gly Val Gly Ile Pro Gly Val Gly Val Pro Gly
2135              2140              2145

Val Gly Val Pro Gly Val Gly Val Pro Gly Val Gly Val Pro Gly
2150              2155              2160

Val Gly Val Pro Gly Val Gly Val Pro Gly Val Gly Val Pro Gly

```
            2165                2170                2175

Val Gly Val Pro Gly Val Gly Val Pro Gly Val Gly Val Pro Gly
    2180                2185                2190

Val Gly Ile Pro Gly Val Gly Val Pro Gly Val Gly Val Pro Gly
    2195                2200                2205

Val Gly Val Pro Gly Val Gly Val Pro Gly Val Gly Val Pro Gly
    2210                2215                2220

Val Gly Val Pro Gly Val Gly Val Pro Gly Val Gly Val Pro Gly
    2225                2230                2235

Val Gly Val Pro Gly Val Gly Val Pro Gly Val Gly Ile Pro Gly
    2240                2245                2250

Val Gly Val Pro Gly Val Gly Val Pro Gly Val Gly Val Pro Gly
    2255                2260                2265

Val Gly Val Pro Gly Val Gly Val Pro Gly Val Gly Val Pro Gly
    2270                2275                2280

Val Gly Val Pro Gly Val Gly Val Pro Gly Val Gly Val Pro Gly
    2285                2290                2295

Val Gly Val Pro Gly Val Gly Ile Pro Gly Val Gly Val Pro Gly
    2300                2305                2310

Val Gly Val Pro Gly Val Gly Val Pro Gly Val Gly Val Pro Gly
    2315                2320                2325

Val Gly Val Pro Gly Val Gly Val Pro Gly Val Gly Val Pro Gly
    2330                2335                2340

Val Gly Val Pro Gly Val Gly Val Pro Gly Val Gly Val Pro Gly
    2345                2350                2355

Val Gly Ile Pro Gly Val Gly Val Pro Gly Val Gly Val Pro Gly
    2360                2365                2370

Val Gly Val Pro Gly Val Gly Val Pro Gly Val Gly Val Pro Gly
    2375                2380                2385

Val Gly Val Pro Gly Val Gly Val Pro Gly Val Gly Val Pro Gly
    2390                2395                2400

Val Gly Val Pro Gly Val Gly Val Pro Gly Val Gly Ile Pro Gly
    2405                2410                2415

Val Gly Val Pro Gly Val Gly Val Pro Gly Val Gly Val Pro Gly
    2420                2425                2430

Val Gly Val Pro Gly Val Gly Val Pro Gly Val Gly Val Pro Gly
    2435                2440                2445

Val Gly Val Pro Gly Val Gly Val Pro Gly Val Gly Val Pro Gly
    2450                2455                2460

Val Gly Val Pro Gly Val Gly Ile Pro Gly Val Gly Val Pro Gly
    2465                2470                2475

Val Gly Val Pro Gly Val Gly Val Pro Gly Val Gly Val Pro Gly
    2480                2485                2490

Val Gly Val Pro Gly Val Gly Val Pro Gly Val Gly Val Pro Gly
    2495                2500                2505

Val Gly Val Pro Gly Val Gly Val Pro Gly Val Gly Val Pro Gly
    2510                2515                2520

Val Gly Ile Pro Gly Val Gly Val Pro Gly Val Gly Val Pro Gly
    2525                2530                2535

Val Gly Val Pro Gly Val Gly Val Pro Gly Val Gly Val Pro Gly
    2540                2545                2550

Val Gly Val Pro Gly Val Gly Val Pro Gly Val Gly Val Pro Gly
    2555                2560                2565
```

```
Val Gly Val Pro Gly Val Gly Val Pro Gly Val Gly  Ile Pro Gly
    2570            2575            2580

Val Gly Val Pro Gly Val Gly Val Pro Gly Val Gly  Val Pro Gly
    2585            2590            2595

Val Gly Val Pro Gly Val Gly Val Pro Gly Val Gly  Val Pro Gly
    2600            2605            2610

Val Gly Val Pro Gly Val Gly Val Pro Gly Val Gly  Val Pro Gly
    2615            2620            2625

Val Gly Val Pro Gly Val Gly Ile Pro Gly Val Gly  Val Pro Gly
    2630            2635            2640

Val Gly Val Pro Gly Val Gly Val Pro Gly Val Gly  Val Pro Gly
    2645            2650            2655

Val Gly Val Pro Gly Val Gly Val Pro Gly Val Gly  Val Pro Gly
    2660            2665            2670

Val Gly Val Pro Gly Val Gly Val Pro Gly Val Gly  Val Pro Gly
    2675            2680            2685

Val Gly Ile Pro Gly Val Gly Val Pro Gly Val Gly  Val Pro Gly
    2690            2695            2700

Val Gly Val Pro Gly Val Gly Val Pro Gly Val Gly  Val Pro Gly
    2705            2710            2715

Val Gly Val Pro Gly Val Gly Val Pro Gly Val Gly  Val Pro Gly
    2720            2725            2730

Val Gly Val Pro Gly Val Gly Val Pro Gly Val Gly  Ile Pro Gly
    2735            2740            2745

Val Gly
    2750

<210> SEQ ID NO 10
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Thr Cys Lys Val Pro Gly Val Gly Val Pro Gly Val Gly Val Pro
1               5                   10                  15

Gly Val Gly Val Pro Gly Val Gly Ile Pro Gly Val Gly Val Pro Gly
            20                  25                  30

Val Gly Val Pro Gly Val Gly Val Pro Gly Val Gly Val Pro Gly Val
        35                  40                  45

Gly Ile Pro Gly Val Gly Val Pro Gly Val Gly Val Pro Gly Val Gly
    50                  55                  60

Val Pro Gly Val Gly Val Pro Gly Val Gly Ile Pro Gly Val Gly Val
65                  70                  75                  80

Pro Gly Val Gly Val Pro Gly Val Gly Val Pro Gly Val Gly Val Pro
                85                  90                  95

Gly Val Gly Ile Pro Gly Val Gly Val Pro Gly Val Gly Val Pro Gly
            100                 105                 110

Val Gly Val Pro Gly Val Gly Val Pro Gly Val Gly Ile Pro Gly Val
        115                 120                 125

Gly Val Pro Gly Val Gly Val Pro Gly Val Gly Val Pro Gly Val Gly
    130                 135                 140

Val Pro Gly Val Gly Ile Pro Gly Val Gly Val Pro Gly Val Gly Val
```

```
                       145                 150                 155                 160
        Pro Gly Val Gly Val Pro Gly Val Gly Val Pro Gly Val Gly Ile Pro
                        165                 170                 175
        Gly Val Gly Val Pro Gly Val Gly Val Pro Gly Val Gly Val Pro Gly
                        180                 185                 190
        Val Gly Val Pro Gly Val Gly Ile Pro Gly Val Gly Val Pro Gly Val
                        195                 200                 205
        Gly Val Pro Gly Val Gly Val Pro Gly Val Gly Val Pro Gly Val Gly
                        210                 215                 220
        Ile Pro Gly Val Gly Val Pro Gly Val Gly Val Pro Gly Val Gly Val
        225                 230                 235                 240
        Pro Gly Val Gly Val Pro Gly Val Gly Ile Pro Gly Val Gly Val Pro
                        245                 250                 255
        Gly Val Gly Val Pro Gly Val Gly Val Pro Gly Val Gly Val Pro Gly
                        260                 265                 270
        Val Gly Ile Pro Gly Val Gly Val Pro Gly Val Gly Val Pro Gly Val
                        275                 280                 285
        Gly Val Pro Gly Val Gly Val Pro Gly Val Gly Ile Pro Gly Val Gly
                        290                 295                 300
        Val Pro Gly Val Gly Val Pro Gly Val Gly Val Pro Gly Val Gly Val
        305                 310                 315                 320
        Pro Gly Val Gly Ile Pro Gly Val Gly Val Pro Gly Val Gly Val Pro
                        325                 330                 335
        Gly Val Gly Val Pro Gly Val Gly Val Pro Gly Val Gly Ile Pro Gly
                        340                 345                 350
        Val Gly Lys Cys Thr Ser
                        355

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Gly Gly Asn Gly Glu Pro Arg Gly Asp Thr Tyr Arg Ala Tyr
1               5                   10                  15

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Gln Ala Gly Asp Val
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)..(3)
<223> OTHER INFORMATION: Asp or Lys

<400> SEQUENCE: 13

Arg Leu Xaa Arg Leu Asp Gly Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Tyr Gly Asp Leu Arg
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Tyr Phe Asp Leu Arg
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Arg Arg Glu Thr Ala Trp Ala Cys
1               5

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Cys Asp Cys Arg Gly Asp Cys Phe Cys Gly
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Gly Tyr Tyr Gly Asp Ala Leu Arg
1               5
```

```
<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 19

His His His His His His
1               5

<210> SEQ ID NO 20
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gatccaaatg taccagcgct agcagtgtct aacgactagt aaatgcacgt cttaaa         56

<210> SEQ ID NO 21
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtttacatgg tcgcgatcgt cacagattgc tgatcattta cgtgcagaat tttcga         56

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Pro Gly Val Gly
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Val Val Val Val Val Val Val Phe
1               5

<210> SEQ ID NO 24
<211> LENGTH: 373
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gly Trp Gly Ser Lys Cys Thr Ser Ala Ser Gly Leu Val Gly Val
```

```
                1               5                   10                  15
            Pro Gly Val Gly Val Pro Gly Val Gly Val Pro Gly Val Gly Val Pro
                            20                  25                  30
            Gly Val Gly Ile Pro Gly Val Gly Val Pro Gly Val Gly Val Pro Gly
                            35                  40                  45
            Val Gly Val Pro Gly Val Gly Val Pro Gly Val Gly Ile Pro Gly Val
                            50                  55                  60
            Gly Val Pro Gly Val Gly Val Pro Gly Val Gly Val Pro Gly Val Gly
            65                  70                  75                  80
            Val Pro Gly Val Gly Ile Pro Gly Val Gly Val Pro Gly Val Gly Val
                            85                  90                  95
            Pro Gly Val Gly Val Pro Gly Val Gly Val Pro Gly Val Gly Ile Pro
                            100                 105                 110
            Gly Val Gly Val Pro Gly Val Gly Val Pro Gly Val Gly Val Pro Gly
                            115                 120                 125
            Val Gly Val Pro Gly Val Gly Ile Pro Gly Val Gly Val Pro Gly Val
                            130                 135                 140
            Gly Val Pro Gly Val Gly Val Pro Gly Val Gly Val Pro Gly Val Gly
            145                 150                 155                 160
            Ile Pro Gly Val Gly Val Pro Gly Val Gly Val Pro Gly Val Gly Val
                            165                 170                 175
            Pro Gly Val Gly Val Pro Gly Val Gly Ile Pro Gly Val Gly Val Pro
                            180                 185                 190
            Gly Val Gly Val Pro Gly Val Gly Val Pro Gly Val Gly Val Pro Gly
                            195                 200                 205
            Val Gly Ile Pro Gly Val Gly Val Pro Gly Val Gly Val Pro Gly Val
                            210                 215                 220
            Gly Val Pro Gly Val Gly Val Pro Gly Val Gly Ile Pro Gly Val Gly
            225                 230                 235                 240
            Val Pro Gly Val Gly Val Pro Gly Val Gly Val Pro Gly Val Gly Val
                            245                 250                 255
            Pro Gly Val Gly Ile Pro Gly Val Gly Val Pro Gly Val Gly Val Pro
                            260                 265                 270
            Gly Val Gly Val Pro Gly Val Gly Val Pro Gly Val Gly Ile Pro Gly
                            275                 280                 285
            Val Gly Val Pro Gly Val Gly Val Pro Gly Val Gly Val Pro Gly Val
                            290                 295                 300
            Gly Val Pro Gly Val Gly Ile Pro Gly Val Gly Val Pro Gly Val Gly
            305                 310                 315                 320
            Val Pro Gly Val Gly Val Pro Gly Val Gly Val Pro Gly Val Gly Ile
                            325                 330                 335
            Pro Gly Val Gly Val Pro Gly Val Gly Val Pro Gly Val Gly Val Pro
                            340                 345                 350
            Gly Val Gly Val Pro Gly Val Gly Ile Pro Gly Val Gly Glu Thr Thr
                            355                 360                 365
            Ser Lys Cys Thr Ser
                    370

<210> SEQ ID NO 25
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 25

```
Met Gly Trp Gly Ser Ala Ser Gly Leu Val Gly Val Pro Gly Val Gly
1               5                   10                  15

Val Pro Gly Val Gly Val Pro Gly Val Gly Val Pro Gly Val Gly Ile
            20                  25                  30

Pro Gly Val Gly Val Pro Gly Val Gly Val Pro Gly Val Gly Val Pro
        35                  40                  45

Gly Val Gly Val Pro Gly Val Gly Ile Pro Gly Val Gly Val Pro Gly
    50                  55                  60

Val Gly Val Pro Gly Val Gly Val Pro Gly Val Gly Val Pro Gly Val
65                  70                  75                  80

Gly Ile Pro Gly Val Gly Val Pro Gly Val Gly Val Pro Gly Val Gly
                85                  90                  95

Val Pro Gly Val Gly Val Pro Gly Val Gly Ile Pro Gly Val Gly Val
            100                 105                 110

Pro Gly Val Gly Val Pro Gly Val Gly Val Pro Gly Val Gly Val Pro
        115                 120                 125

Gly Val Gly Ile Pro Gly Val Gly Val Pro Gly Val Gly Val Pro Gly
    130                 135                 140

Val Gly Val Pro Gly Val Gly Val Pro Gly Val Gly Ile Pro Gly Val
145                 150                 155                 160

Gly Val Pro Gly Val Gly Val Pro Gly Val Gly Val Pro Gly Val Gly
                165                 170                 175

Val Pro Gly Val Gly Ile Pro Gly Val Gly Val Pro Gly Val Gly Val
            180                 185                 190

Pro Gly Val Gly Val Pro Gly Val Gly Val Pro Gly Val Gly Ile Pro
        195                 200                 205

Gly Val Gly Val Pro Gly Val Gly Val Pro Gly Val Gly Val Pro Gly
    210                 215                 220

Val Gly Val Pro Gly Val Gly Ile Pro Gly Val Gly Val Pro Gly Val
225                 230                 235                 240

Gly Val Pro Gly Val Gly Val Pro Gly Val Gly Val Pro Gly Val Gly
                245                 250                 255

Ile Pro Gly Val Gly Glu Thr Thr Ser
            260                 265
```

<210> SEQ ID NO 26
<211> LENGTH: 373
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Met Gly Trp Gly Ser Lys Cys Thr Ser Ala Ser Gly Leu Val Gly Val
1               5                   10                  15

Pro Gly Val Gly Val Pro Gly Val Gly Ile Pro Gly Val Gly Val Pro
            20                  25                  30

Gly Val Gly Val Pro Gly Val Gly Val Pro Gly Val Gly Val Pro Gly
        35                  40                  45

Val Gly Ile Pro Gly Val Gly Val Pro Gly Val Gly Val Pro Gly Val
    50                  55                  60

Gly Val Pro Gly Val Gly Val Pro Gly Val Gly Ile Pro Gly Val Gly
65                  70                  75                  80
```

Val Pro Gly Val Gly Val Pro Gly Val Gly Val
            85                  90                  95

Pro Gly Val Gly Ile Pro Gly Val Gly Val Pro Gly Val Gly Val Pro
            100                 105                 110

Gly Val Gly Val Pro Gly Val Gly Val Pro Gly Val Gly Ile Pro Gly
            115                 120                 125

Val Gly Val Pro Gly Val Gly Val Pro Gly Val Gly Val Pro Gly Val
            130                 135                 140

Gly Val Pro Gly Val Gly Ile Pro Gly Val Gly Val Pro Gly Val Gly
145                 150                 155                 160

Val Pro Gly Val Gly Val Pro Gly Val Gly Val Pro Gly Val Gly Ile
            165                 170                 175

Pro Gly Val Gly Val Pro Gly Val Gly Val Pro Gly Val Gly Val Pro
            180                 185                 190

Gly Val Gly Val Pro Gly Val Gly Ile Pro Gly Val Gly Val Pro Gly
            195                 200                 205

Val Gly Val Pro Gly Val Gly Val Pro Gly Val Gly Val Pro Gly Val
            210                 215                 220

Gly Ile Pro Gly Val Gly Val Pro Gly Val Gly Val Pro Gly Val Gly
225                 230                 235                 240

Val Pro Gly Val Gly Val Pro Gly Val Gly Ile Pro Gly Val Gly Val
            245                 250                 255

Pro Gly Val Gly Val Pro Gly Val Gly Val Pro Gly Val Gly Val Pro
            260                 265                 270

Gly Val Gly Ile Pro Gly Val Gly Val Pro Gly Val Gly Val Pro Gly
            275                 280                 285

Val Gly Val Pro Gly Val Gly Val Pro Gly Val Gly Ile Pro Gly Val
            290                 295                 300

Gly Val Pro Gly Val Gly Val Pro Gly Val Gly Val Pro Gly Val Gly
305                 310                 315                 320

Val Pro Gly Val Gly Ile Pro Gly Val Gly Val Pro Gly Val Gly Val
            325                 330                 335

Pro Gly Val Gly Val Pro Gly Val Gly Val Pro Gly Val Gly Ile Pro
            340                 345                 350

Gly Val Gly Val Pro Gly Val Gly Val Pro Gly Val Gly Glu Thr Thr
            355                 360                 365

Ser Lys Cys Thr Ser
370

<210> SEQ ID NO 27
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
ggatccaaat gtaccagcgc tagcggtctc gttggtgtac ctggtgttgg cgtcccgggt    60
gtaggtatcc caggcgttgg tgtaccgggt gtaggcgttc caggcgttgg tgtacctggt   120
gttggcgtcc cgggtgtagg tatcccaggc gttggtgtac cgggtgtagg cgttccaggc   180
gttggtgtac ctggtgttgg cgtcccgggt gtaggtatcc caggcgttgg tgtaccgggt   240
gtaggcgttc caggcgttgg tgtacctggt gttggcgtcc cgggtgtagg tatcccaggc   300

```
gttggtgtac cgggtgtagg cgttccaggc gttggtgtac ctggtgttgg cgtcccgggt      360
gtaggtatcc caggcgttgg tgtaccgggt gtaggcgttc caggcgttgg tgtacctggt      420
gttggcgtcc cgggtgtagg tatcccaggc gttggtgtac cgggtgtagg cgttccaggc      480
gttggtgtac ctggtgttgg cgtcccgggt gtaggtatcc caggcgttgg tgtaccgggt      540
gtaggcgttc caggcgttgg tgtacctggt gttggcgtcc cgggtgtagg tatcccaggc      600
gttggtgtac cgggtgtagg cgttccaggc gttggtgtac ctggtgttgg cgtcccgggt      660
gtaggtatcc caggcgttgg tgtaccgggt gtaggcgttc caggcgttgg tgtacctggt      720
gttggcgtcc cgggtgtagg tatcccaggc gttggtgtac cgggtgtagg cgttccaggc      780
gttggtgtac ctggtgttgg cgtcccgggt gtaggtatcc caggcgttgg tgtaccgggt      840
gtaggcgttc caggcgttgg tgtacctggt gttggcgtcc cgggtgtagg tatcccaggc      900
gttggtgtac cgggtgtagg cgttccaggc gttggtgtac ctggtgttgg cgtcccgggt      960
gtaggtatcc caggcgttgg tgtaccgggt gtaggcgttc caggcgttgg tgtacctggt     1020
gttggcgtcc cgggtgtagg tatcccaggc gttggtgtac cgggtgtagg cgttccaggc     1080
gttggtgaga ccactagtta aatgaataaa tgcacgtctt aaaagctt                  1128
```